(12) United States Patent
Cizeron et al.

(10) Patent No.: US 11,370,724 B2
(45) Date of Patent: Jun. 28, 2022

(54) CATALYTIC FORMS AND FORMULATIONS

(71) Applicant: Lummus Technology LLC, Houston, TX (US)

(72) Inventors: Joel M. Cizeron, Redwood City, CA (US); Fabio R. Zurcher, Brisbane, CA (US); Jarod McCormick, San Carlos, CA (US); Joel Gamoras, Vallejo, CA (US); Roger Vogel, Fairfield, CA (US); Joel David Vincent, Berkeley, CA (US); Greg Nyce, Pleasanton, CA (US); Wayne P. Schammel, Brisbane, CA (US); Erik C. Scher, San Francisco, CA (US); Daniel Rosenberg, San Francisco, CA (US); Erik-Jan Ras, Amsterdam (NL); Erik Freer, Mountain View, CA (US)

(73) Assignee: Lummus Technology LLC, Houston, TX (US)

( * ) Notice: Subject to any disclaimer, the term of this patent is extended or adjusted under 35 U.S.C. 154(b) by 246 days.

(21) Appl. No.: 16/366,149

(22) Filed: Mar. 27, 2019

(65) Prior Publication Data

US 2020/0024214 A1 Jan. 23, 2020

Related U.S. Application Data

(63) Continuation of application No. 13/901,319, filed on May 23, 2013, now abandoned.
(Continued)

(51) Int. Cl.
*C07C 2/82* (2006.01)
*B01J 23/10* (2006.01)
(Continued)

(52) U.S. Cl.
CPC .............. *C07C 2/82* (2013.01); *B01J 23/10* (2013.01); *B01J 23/34* (2013.01); *B01J 29/06* (2013.01);
(Continued)

(58) Field of Classification Search
None
See application file for complete search history.

(56) References Cited

U.S. PATENT DOCUMENTS 3,413,817 A 12/1968 Kniel
3,596,473 A 8/1971 Streich
(Continued)

FOREIGN PATENT DOCUMENTS

CN 86104014 A 12/1986
CN 1073891 A 7/1993
(Continued)

OTHER PUBLICATIONS

Norby et al., "Protons in Ca-doped $La_2O_3$, $Nd:O_3$ and $LaNdO_3$," *Solid State Ionics* 53-56:446-452, 1992.
(Continued)

*Primary Examiner* — Colin W. Slifka
(74) *Attorney, Agent, or Firm* — Seed IP Law Group LLP

(57) ABSTRACT

Catalytic forms and formulations are provided. The catalytic forms and formulations are useful in a variety of catalytic reactions, for example, the oxidative coupling of methane. Related methods for use and manufacture of the same are also disclosed.

31 Claims, 6 Drawing Sheets

Related U.S. Application Data

(60) Provisional application No. 61/780,686, filed on Mar. 13, 2013, provisional application No. 61/651,396, filed on May 24, 2012.

(51) Int. Cl.
| | |
|---|---|
| *B01J 23/34* | (2006.01) |
| *C07C 2/06* | (2006.01) |
| *C07C 2/84* | (2006.01) |
| *B01J 35/06* | (2006.01) |
| *B01J 35/10* | (2006.01) |
| *B01J 35/04* | (2006.01) |
| *B01J 29/06* | (2006.01) |
| *B01J 35/02* | (2006.01) |
| *B01J 37/02* | (2006.01) |
| *B01J 35/00* | (2006.01) |
| *B82Y 30/00* | (2011.01) |

(52) U.S. Cl.
CPC ......... *B01J 35/0013* (2013.01); *B01J 35/026* (2013.01); *B01J 35/04* (2013.01); *B01J 35/06* (2013.01); *B01J 35/1009* (2013.01); *B01J 35/1014* (2013.01); *B01J 37/0211* (2013.01); *B01J 37/0215* (2013.01); *B01J 37/0234* (2013.01); *C07C 2/06* (2013.01); *C07C 2/84* (2013.01); *B82Y 30/00* (2013.01); *C07C 2523/02* (2013.01); *C07C 2523/10* (2013.01); *C07C 2523/30* (2013.01); *C07C 2523/34* (2013.01); *C07C 2527/224* (2013.01); *Y02P 20/52* (2015.11)

(56) References Cited

U.S. PATENT DOCUMENTS

| | | | |
|---|---|---|---|
| 4,105,641 | A | 8/1978 | Buysch et al. |
| 4,126,580 | A | 11/1978 | Lauder |
| 4,140,504 | A | 2/1979 | Campbell et al. |
| 4,375,566 | A | 3/1983 | Kawamata et al. |
| 4,554,395 | A | 11/1985 | Jones et al. |
| 4,629,718 | A | 12/1986 | Jones et al. |
| 4,636,378 | A | 1/1987 | Pastor et al. |
| 4,695,668 | A | 9/1987 | Velenyi |
| 4,751,336 | A | 6/1988 | Jezl et al. |
| 4,754,091 | A | 6/1988 | Jezl et al. |
| 4,754,093 | A | 6/1988 | Jezl et al. |
| 4,777,313 | A | 10/1988 | Sofranko et al. |
| 4,780,449 | A | 10/1988 | Hicks |
| 4,814,539 | A | 3/1989 | Jezl et al. |
| 4,826,796 | A | 5/1989 | Erekson et al. |
| 4,844,803 | A | 7/1989 | Urech et al. |
| 4,849,571 | A | 7/1989 | Gaffney |
| 4,895,823 | A | 1/1990 | Kolts et al. |
| 4,900,347 | A | 2/1990 | McCue et al. |
| 4,939,311 | A | 7/1990 | Washecheck et al. |
| 4,939,312 | A | 7/1990 | Baerns et al. |
| 4,962,252 | A | 10/1990 | Wade |
| 5,012,028 | A | 4/1991 | Gupta et al. |
| 5,024,984 | A | 6/1991 | Kaminsky et al. |
| 5,041,405 | A | 8/1991 | Lunsford et al. |
| 5,057,478 | A | 10/1991 | Abe et al. |
| 5,073,662 | A | 12/1991 | Olbrich |
| 5,080,872 | A | 1/1992 | Jezl et al. |
| 5,118,898 | A | 6/1992 | Tyler et al. |
| 5,132,472 | A | 7/1992 | Durante et al. |
| 5,134,103 | A | 7/1992 | Lowery |
| 5,137,862 | A | 8/1992 | Mackrodt et al. |
| 5,149,516 | A | 9/1992 | Han et al. |
| 5,179,056 | A | 1/1993 | Bartley |
| 5,196,634 | A | 3/1993 | Washecheck et al. |
| 5,198,596 | A | 3/1993 | Kaminsky et al. |
| 5,263,998 | A | 11/1993 | Mackrodt et al. |
| 5,276,237 | A | 1/1994 | Mieville |
| 5,306,854 | A | 4/1994 | Choudhary et al. |
| 5,312,795 | A | 5/1994 | Kaminsky et al. |
| 5,316,995 | A | 5/1994 | Kaminsky et al. |
| 5,328,883 | A | 7/1994 | Washecheck et al. |
| 5,336,825 | A | 8/1994 | Choudhary et al. |
| 5,336,826 | A | 8/1994 | Brophy et al. |
| 5,371,306 | A | 12/1994 | Woo et al. |
| 5,414,157 | A | 5/1995 | Durante et al. |
| 5,500,149 | A | 3/1996 | Green et al. |
| 5,523,493 | A | 6/1996 | Cameron et al. |
| 5,599,510 | A | 2/1997 | Kaminsky et al. |
| 5,659,090 | A | 8/1997 | Cameron et al. |
| 5,670,442 | A | 9/1997 | Fornasari et al. |
| RE35,632 | E | 10/1997 | Leyshon |
| RE35,633 | E | 10/1997 | Leyshon |
| 5,712,217 | A | 1/1998 | Choudhary et al. |
| 5,714,657 | A | 2/1998 | deVries |
| 5,736,107 | A | 4/1998 | Inomata et al. |
| 5,744,015 | A | 4/1998 | Mazanec et al. |
| 5,749,937 | A | 5/1998 | Detering et al. |
| 5,750,821 | A | 5/1998 | Inomata et al. |
| 5,763,722 | A | 6/1998 | Vic et al. |
| 5,789,339 | A | 8/1998 | Ziebarth et al. |
| 5,817,904 | A | 10/1998 | Vic et al. |
| 5,830,822 | A | 11/1998 | Euzen |
| 5,849,973 | A | 12/1998 | Van Der Vaart |
| 5,866,737 | A | 2/1999 | Hagemeyer et al. |
| 5,897,945 | A | 4/1999 | Lieber et al. |
| 5,917,136 | A | 6/1999 | Gaffney et al. |
| 5,935,293 | A | 8/1999 | Detering et al. |
| 5,935,897 | A | 8/1999 | Trubenbach et al. |
| 5,935,898 | A | 8/1999 | Trubenbach et al. |
| 5,936,135 | A | 8/1999 | Choudhary et al. |
| 5,959,170 | A | 9/1999 | Withers |
| 5,968,866 | A | 10/1999 | Wu |
| 6,020,533 | A | 2/2000 | Lewis et al. |
| 6,037,298 | A | 3/2000 | Hagen et al. |
| 6,087,545 | A | 7/2000 | Choudhary et al. |
| 6,096,934 | A | 8/2000 | Rekoske |
| 6,110,979 | A | 8/2000 | Nataraj et al. |
| 6,114,400 | A | 9/2000 | Nataraj et al. |
| 6,143,203 | A | 11/2000 | Zeng et al. |
| 6,146,549 | A | 11/2000 | Mackay et al. |
| 6,153,149 | A | 11/2000 | Rabitz et al. |
| 6,262,325 | B1 | 7/2001 | Narbeshuber et al. |
| 6,316,377 | B1 | 11/2001 | Fulton et al. |
| 6,355,093 | B1 | 3/2002 | Schwartz et al. |
| 6,403,523 | B1 | 6/2002 | Cantrell et al. |
| RE37,853 | E | 9/2002 | Detering et al. |
| 6,447,745 | B1 | 9/2002 | Feeley et al. |
| 6,518,218 | B1 | 2/2003 | Sun et al. |
| 6,518,476 | B1 | 2/2003 | Culp et al. |
| 6,521,806 | B1 | 2/2003 | Tamura et al. |
| 6,521,808 | B1 | 2/2003 | Ozkan et al. |
| 6,576,200 | B1 | 6/2003 | Yamamoto et al. |
| 6,576,803 | B2 | 6/2003 | Cantrell et al. |
| 6,596,912 | B1 | 7/2003 | Lunsford et al. |
| 6,610,124 | B1 | 8/2003 | Dolan et al. |
| 6,696,388 | B2 | 2/2004 | Kourtakis et al. |
| 6,726,850 | B1 | 4/2004 | Reyes et al. |
| 6,730,808 | B2 | 5/2004 | Bitterlich et al. |
| 6,747,066 | B2 | 6/2004 | Wang et al. |
| 6,761,838 | B2 | 7/2004 | Zeng et al. |
| 6,764,602 | B2 | 7/2004 | Shutt et al. |
| 6,800,702 | B2 | 10/2004 | Wass |
| 6,821,500 | B2 | 11/2004 | Fincke et al. |
| 6,821,656 | B2 | 11/2004 | Dietrich et al. |
| 7,116,546 | B2 | 10/2006 | Chow et al. |
| 7,166,267 | B2 | 1/2007 | Villa |
| 7,176,342 | B2 | 2/2007 | Bellussi et al. |
| 7,183,451 | B2 | 2/2007 | Gattis et al. |
| 7,199,273 | B2 | 4/2007 | Molinier et al. |
| 7,208,647 | B2 | 4/2007 | Peterson et al. |
| 7,250,543 | B2 | 7/2007 | Bagherzadeh et al. |
| 7,291,321 | B2 | 11/2007 | Bagherzadeh et al. |
| 7,332,108 | B2 | 2/2008 | Chartier et al. |
| 7,361,622 | B2 | 4/2008 | Benderly et al. |
| 7,396,798 | B2 | 7/2008 | Ma et al. |
| 7,414,006 | B2 | 8/2008 | McConville et al. |

(56) References Cited

U.S. PATENT DOCUMENTS

| | | |
|---|---|---|
| 7,438,887 B2 | 10/2008 | Suib et al. |
| 7,452,844 B2 | 11/2008 | Hu et al. |
| 7,473,814 B2 | 1/2009 | Basset et al. |
| 7,566,440 B2 | 7/2009 | Lim et al. |
| 7,576,030 B2 | 8/2009 | Benderly |
| 7,576,296 B2 | 8/2009 | Fincke et al. |
| 7,585,812 B2 | 9/2009 | Hu et al. |
| 7,589,246 B2 | 9/2009 | Iaccino et al. |
| 7,619,290 B2 | 11/2009 | Lieber et al. |
| 7,659,437 B2 | 2/2010 | Iaccino et al. |
| 7,667,085 B2 | 2/2010 | Gattis et al. |
| 7,683,227 B2 | 3/2010 | Iaccino et al. |
| 7,687,041 B2 | 3/2010 | Singh |
| 7,700,816 B2 | 4/2010 | Xu |
| 7,728,186 B2 | 6/2010 | Iaccino et al. |
| 7,781,636 B2 | 8/2010 | Iaccino et al. |
| 7,795,490 B2 | 9/2010 | Iaccino et al. |
| 7,829,749 B2 | 11/2010 | Gao et al. |
| 7,867,938 B2 | 1/2011 | De et al. |
| 7,868,243 B2 | 1/2011 | Plissonnier et al. |
| 7,879,119 B2 | 2/2011 | Abughazaleh et al. |
| 7,902,113 B2 | 3/2011 | Zarrinpashne et al. |
| 7,902,639 B2 | 3/2011 | Garrou et al. |
| 7,910,670 B2 | 3/2011 | Knudsen et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,932,311 B2 | 4/2011 | Aymonier et al. |
| 7,943,106 B2 | 5/2011 | Robinson |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 8,039,681 B2 | 10/2011 | Krusic et al. |
| 8,071,498 B2 | 12/2011 | Aono et al. |
| 8,071,836 B2 | 12/2011 | Butler |
| 8,129,305 B2 | 3/2012 | Bagherzadeh et al. |
| 8,277,525 B2 | 10/2012 | Dalton |
| 8,293,805 B2 | 10/2012 | Khan et al. |
| 8,361,925 B2 | 1/2013 | Matsueda et al. |
| 8,399,527 B1 | 3/2013 | Brown et al. |
| 8,399,726 B2 | 3/2013 | Chinga et al. |
| 8,414,798 B2 | 4/2013 | Costello et al. |
| 8,435,920 B2 | 5/2013 | White et al. |
| 8,450,546 B2 | 5/2013 | Chinta et al. |
| 8,552,236 B2 | 10/2013 | Iaccino |
| 8,647,999 B2 | 2/2014 | Hayashi et al. |
| 8,669,171 B2 | 3/2014 | Perraud et al. |
| 8,710,286 B2 | 4/2014 | Butler |
| 8,729,328 B2 | 5/2014 | Chinta et al. |
| 8,759,598 B2 | 6/2014 | Hayashi et al. |
| 8,796,497 B2 | 8/2014 | Chinta et al. |
| 8,865,347 B2 | 10/2014 | Hu et al. |
| 8,911,834 B2 | 12/2014 | Aktas et al. |
| 8,912,381 B2 | 12/2014 | Chinta et al. |
| 8,921,256 B2 | 12/2014 | Cizeron et al. |
| 8,932,781 B2 | 1/2015 | Yang et al. |
| 8,962,517 B2 | 2/2015 | Zurcher et al. |
| 9,040,762 B2 | 5/2015 | Cizeron et al. |
| 9,101,890 B2 | 8/2015 | Tonkovich et al. |
| 9,133,079 B2 | 9/2015 | Weinberger et al. |
| 9,446,387 B2 | 9/2016 | Cizeron et al. |
| 9,446,397 B2 | 9/2016 | Gamoras et al. |
| 9,469,577 B2 | 10/2016 | Schammel et al. |
| 9,527,784 B2 | 12/2016 | Weinberger et al. |
| 9,556,086 B2 | 1/2017 | Schammel et al. |
| 9,598,328 B2 | 3/2017 | Nyce et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,956,544 B2 | 5/2018 | Schammel et al. |
| 9,963,402 B2 | 5/2018 | Cizeron et al. |
| 10,183,900 B2 | 1/2019 | Nyce et al. |
| 10,195,603 B2 | 2/2019 | Scher et al. |
| 10,300,465 B2 | 5/2019 | Freer et al. |
| 10,308,565 B2 | 6/2019 | Schammel et al. |
| 10,654,769 B2 | 5/2020 | Cizeron et al. |
| 10,780,420 B2 | 9/2020 | Schammel et al. |
| 10,865,166 B2 | 12/2020 | Schammel et al. |
| 11,000,835 B2 | 5/2021 | Freer et al. |
| 11,078,132 B2 | 8/2021 | Zurcher et al. |
| 2001/0044520 A1 | 11/2001 | Suzuki et al. |
| 2002/0150522 A1 | 10/2002 | Heim et al. |
| 2003/0135971 A1 | 7/2003 | Liberman et al. |
| 2003/0189202 A1 | 10/2003 | Li et al. |
| 2003/0207984 A1 | 11/2003 | Ding et al. |
| 2003/0233019 A1 | 12/2003 | Sherwood |
| 2004/0005723 A1 | 1/2004 | Empedocles et al. |
| 2004/0098914 A1 | 5/2004 | Balachandran et al. |
| 2004/0187963 A1 | 9/2004 | Tayu et al. |
| 2004/0220053 A1 | 11/2004 | Bagherzadeh et al. |
| 2005/0009686 A1 | 1/2005 | Julsrud et al. |
| 2005/0065391 A1 | 3/2005 | Gattis et al. |
| 2005/0199559 A1 | 9/2005 | Duby |
| 2005/0221083 A1 | 10/2005 | Belcher et al. |
| 2005/0255993 A1 | 11/2005 | Tanaka et al. |
| 2006/0018821 A1 | 1/2006 | Suzuki et al. |
| 2006/0083970 A1 | 4/2006 | Shibutani et al. |
| 2006/0125025 A1 | 6/2006 | Kawashima et al. |
| 2006/0135838 A1 | 6/2006 | Bagherzadeh et al. |
| 2006/0141268 A1 | 6/2006 | Kalkan et al. |
| 2006/0155157 A1 | 7/2006 | Zarrinpashne et al. |
| 2006/0177629 A1 | 8/2006 | Kunieda |
| 2006/0283780 A1 | 12/2006 | Spivey et al. |
| 2006/0284162 A1 | 12/2006 | Kurt et al. |
| 2007/0027030 A1 | 2/2007 | Cheung et al. |
| 2007/0043181 A1 | 2/2007 | Knudsen et al. |
| 2007/0073083 A1 | 3/2007 | Sunley |
| 2007/0083073 A1 | 4/2007 | Bagherzadeh et al. |
| 2007/0095445 A1 | 5/2007 | Gangopadhyay et al. |
| 2007/0106089 A1 | 5/2007 | Benderly et al. |
| 2007/0138082 A1 | 6/2007 | Conners, Jr. et al. |
| 2007/0138459 A1 | 6/2007 | Wong |
| 2007/0158611 A1 | 7/2007 | Oldenburg |
| 2008/0051279 A1 | 2/2008 | Klett et al. |
| 2008/0141713 A1 | 6/2008 | Verma |
| 2008/0262114 A1 | 10/2008 | Reynhout |
| 2008/0267852 A1 | 10/2008 | Schumacher et al. |
| 2008/0275143 A1 | 11/2008 | Malhotra et al. |
| 2008/0279744 A1 | 11/2008 | Robinson |
| 2008/0281136 A1 | 11/2008 | Bagherzadeh et al. |
| 2008/0293980 A1 | 11/2008 | Kiesslich et al. |
| 2008/0318044 A1 | 12/2008 | Tian et al. |
| 2009/0043141 A1 | 2/2009 | Mazanec et al. |
| 2009/0087496 A1 | 4/2009 | Katusic et al. |
| 2009/0202427 A1 | 8/2009 | Katusic et al. |
| 2009/0259076 A1 | 10/2009 | Simmons et al. |
| 2009/0267852 A1 | 10/2009 | Tahmisian et al. |
| 2009/0324470 A1 | 12/2009 | Alamdari et al. |
| 2010/0000153 A1 | 1/2010 | Kurkjian et al. |
| 2010/0003179 A1 | 1/2010 | Katusic et al. |
| 2010/0173070 A1 | 7/2010 | Niu |
| 2010/0183937 A1 | 7/2010 | Halloran et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0200501 A1 | 8/2010 | Hoag et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0049132 A1 | 3/2011 | Lee |
| 2011/0070139 A1 | 3/2011 | Kim et al. |
| 2011/0104588 A1 | 5/2011 | Kwon et al. |
| 2011/0124488 A1 | 5/2011 | Neltner et al. |
| 2011/0160508 A1 | 6/2011 | Ma et al. |
| 2011/0171629 A1 | 7/2011 | Swager et al. |
| 2011/0189559 A1 | 8/2011 | De Miranda et al. |
| 2011/0217544 A1 | 9/2011 | Young et al. |
| 2011/0240926 A1 | 10/2011 | Schellen et al. |

(56) References Cited

U.S. PATENT DOCUMENTS

| | | |
|---|---|---|
| 2011/0257453 A1 | 10/2011 | Chinta et al. |
| 2011/0275011 A1 | 11/2011 | Zhu et al. |
| 2012/0029218 A1 | 2/2012 | Kim et al. |
| 2012/0041246 A1 | 2/2012 | Scher et al. |
| 2012/0065412 A1 | 3/2012 | Abdallah et al. |
| 2012/0116094 A1 | 5/2012 | Swager et al. |
| 2012/0129690 A1 | 5/2012 | Larcher et al. |
| 2012/0136164 A1 | 5/2012 | Ying et al. |
| 2012/0153860 A1 | 6/2012 | Wang |
| 2012/0164470 A1 | 6/2012 | Leschkies et al. |
| 2012/0172648 A1 | 7/2012 | Seebauer |
| 2012/0183770 A1 | 7/2012 | Bosnyak et al. |
| 2012/0198769 A1 | 8/2012 | Schirrmeister et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0264598 A1 | 10/2012 | Carpenter et al. |
| 2013/0023709 A1 | 1/2013 | Cizeron et al. |
| 2013/0025201 A1 | 1/2013 | Dalton |
| 2013/0039806 A1 | 2/2013 | Blinn et al. |
| 2013/0040806 A1 | 2/2013 | Dismukes et al. |
| 2013/0089739 A1 | 4/2013 | Polshettiwar et al. |
| 2013/0105305 A1 | 5/2013 | Yang et al. |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0178680 A1 | 7/2013 | Ha et al. |
| 2013/0225884 A1 | 8/2013 | Weinberger et al. |
| 2013/0252808 A1 | 9/2013 | Yamazaki et al. |
| 2013/0253248 A1 | 9/2013 | Gamoras et al. |
| 2013/0266809 A1 | 10/2013 | Nueraji et al. |
| 2013/0270180 A1 | 10/2013 | Zhang et al. |
| 2014/0050629 A1 | 2/2014 | Masuda et al. |
| 2014/0054516 A1 | 2/2014 | Moon et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0171707 A1 | 6/2014 | Nyce et al. |
| 2014/0178788 A1 | 6/2014 | Ha et al. |
| 2014/0194663 A1 | 7/2014 | Butler |
| 2014/0249339 A1 | 9/2014 | Simanzhenkov et al. |
| 2014/0274671 A1 | 9/2014 | Schammel et al. |
| 2014/0332733 A1 | 11/2014 | Joo et al. |
| 2014/0378728 A1 | 12/2014 | Davis et al. |
| 2015/0010467 A1 | 1/2015 | Ito et al. |
| 2015/0073192 A1 | 3/2015 | Cizeron et al. |
| 2015/0087875 A1 | 3/2015 | Zurcher et al. |
| 2015/0125383 A1 | 5/2015 | Yamazaki et al. |
| 2015/0224482 A1 | 8/2015 | Cizeron et al. |
| 2015/0314267 A1 | 11/2015 | Schammel et al. |
| 2015/0321974 A1 | 11/2015 | Schammel et al. |
| 2016/0074844 A1 | 3/2016 | Freer et al. |
| 2016/0107143 A1 | 4/2016 | Schammel et al. |
| 2016/0122261 A1 | 5/2016 | Schammel et al. |
| 2016/0340272 A1 | 11/2016 | Cizeron et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0341997 A1 | 11/2017 | Nyce et al. |
| 2018/0093931 A1 | 4/2018 | Schammel et al. |
| 2018/0117570 A1 | 5/2018 | Freer et al. |
| 2018/0117579 A1 | 5/2018 | Scher et al. |
| 2018/0118637 A1 | 5/2018 | Zurcher et al. |
| 2018/0311658 A1 | 11/2018 | Liang et al. |
| 2019/0010096 A1 | 1/2019 | Schammel et al. |
| 2019/0022626 A1 | 1/2019 | Schammel et al. |
| 2019/0077728 A1 | 3/2019 | Cizeron et al. |
| 2020/0016580 A1 | 1/2020 | Freer et al. |
| 2020/0017423 A1 | 1/2020 | Tanur et al. |
| 2020/0070136 A1 | 3/2020 | Scher et al. |
| 2020/0109094 A1 | 4/2020 | Nyce et al. |
| 2020/0238256 A1 | 7/2020 | Zurcher et al. |
| 2020/0368725 A1 | 11/2020 | Schammel et al. |
| 2020/0377429 A1 | 12/2020 | Cizeron et al. |
| 2021/0130260 A1 | 5/2021 | Schammel et al. |

FOREIGN PATENT DOCUMENTS

| | | |
|---|---|---|
| CN | 1087291 A | 6/1994 |
| CN | 1100669 A | 3/1995 |
| CN | 1321728 A | 11/2001 |
| CN | 1389293 A | 1/2003 |
| CN | 1403375 A | 3/2003 |
| CN | 1930333 A | 3/2007 |
| CN | 101 224 432 A | 7/2008 |
| CN | 101 387 019 A | 3/2009 |
| CN | 101495429 A | 7/2009 |
| CN | 102 125 825 A | 7/2011 |
| CN | 103118777 A | 5/2013 |
| DE | 3406751 A1 | 8/1985 |
| EP | 0 189 079 A1 | 7/1986 |
| EP | 0 253 522 A2 | 1/1988 |
| EP | 0 595 425 A1 | 5/1994 |
| EP | 0 761 307 B1 | 2/2003 |
| EP | 0 764 467 B1 | 2/2003 |
| EP | 1 632 467 A1 | 3/2006 |
| EP | 1 749 807 A1 | 2/2007 |
| EP | 2 287 142 A1 | 2/2011 |
| EP | 2 374 526 A1 | 10/2011 |
| EP | 2 853 521 A1 | 1/2015 |
| FR | 649 429 A | 12/1928 |
| GB | 2 191 212 A | 12/1987 |
| GB | 2485461 A | 5/2012 |
| JP | 63-63626 A | 3/1988 |
| JP | 2-218623 A | 8/1990 |
| JP | 3-262535 A | 11/1991 |
| JP | 5-238961 A | 9/1993 |
| JP | 2005 161225 A | 6/2005 |
| JP | 2011-32257 A | 2/2011 |
| RU | 2 134 675 C1 | 8/1999 |
| WO | 86/007351 A1 | 12/1986 |
| WO | 98/14322 A1 | 4/1998 |
| WO | 00/016901 A1 | 3/2000 |
| WO | 02/080280 A1 | 10/2002 |
| WO | 2004/033488 A2 | 4/2004 |
| WO | 2005/067683 A2 | 7/2005 |
| WO | 2007/130515 A2 | 11/2007 |
| WO | 2008/005055 A2 | 1/2008 |
| WO | 2008/014841 A1 | 2/2008 |
| WO | 2008/022147 A1 | 2/2008 |
| WO | 2008/073143 A2 | 6/2008 |
| WO | 2009/071463 A2 | 6/2009 |
| WO | 2009/115805 A1 | 9/2009 |
| WO | 2010/005453 A2 | 1/2010 |
| WO | 2011/050359 A1 | 4/2011 |
| WO | 2011/149996 A2 | 12/2011 |
| WO | 2012/162526 A2 | 11/2012 |
| WO | WO-2012162526 A2 * 11/2012 ............ B01J 37/035 |
| WO | 2013/082318 A2 | 6/2013 |
| WO | 2013/177433 A2 | 11/2013 |
| WO | 2013/186789 A1 | 12/2013 |
| WO | 2014/043603 A1 | 3/2014 |
| WO | 2014/049445 A2 | 4/2014 |

OTHER PUBLICATIONS

U.S. Appl. No. 16/986,065, filed Aug. 5, 2020.
U.S. Appl. No. 17/098,027, filed Nov. 13, 2020.
Choudhary et al., "Oxidative coupling of methane over alkaline earth oxides deposited on commercial support precoated with rare earth oxides," *Fuel* 78:427-437, 1999.
Yun et al., "Current Status and Some Perspectives of Rare Earth Catalytic Materials," *Journal of The Chinese Rare Earth Society* 25(1): 1-15, 2007, (w/ English Abstract).
Ekstrom et al., "Effect of Pressure on the Oxidative Coupling Reaction of Methane," *Applied Catalysis* 62:253-269, 1990.
Noon et al., "Oxidative coupling of methane with $La_2O_3$-$CeO_2$ nanofiber fabrics: A reaction engineering study," *Journal of Natural Gas Science and Engineering* 18:406-411, 2014.

(56) References Cited

OTHER PUBLICATIONS

U.S. Appl. No. 16/777,352, filed Jan. 30, 2020.
U.S. Appl. No. 16/834,972, filed Mar. 30, 2020.
"Autothermal Partial Oxidative Coupling of Methane," An IP.com Prior Art Database Technical Disclosure, IP.com No. IPCOM000173290D, Jul. 29, 2008.
Agapie, "Selective ethylene oligomerization: recent advances in chromium catalysis and mechanistic investigations" Coord Chem Rev 255:861-880, 2011.
Au et al., "A Comparison of $BaF_2/La_2O_3$ and $Bar_2/La_2O_3$ Catalysts for the Oxidative Coupling of Methane," Journal of Catalysis 159:280-287, 1996.
Bergh et al. "Combinatorial heterogeneous catalysis: oxidative dehydrogenation of ethane to ethylene, selective oxidation of ethane to acetic acid, and selective ammoxidation of propane to acrylonitrile" Topics in Catalysis 23:65-79, 2003.
Carter et al. "High activity ethylene trimerisation catalysts based on diphosphine ligands." Chem Commun., pp. 858-859, 2002.
Cavani et al., "Oxidative dehydrogenation of ethane and propane: How far from commercial implementation?" Catalysis Today 127:113-131, 2007.
Choudhary et al., "Oxidative Coupling of Methane and Oxidative Dehydrogenation of Ethane over Strontium-Promoted Rare Earth Oxide Catalysts," J. Chem. Technol. Biotechnol. 77:167-172, 1998.
Choudhary et al., "Oxidative Coupling of Methane over SrO Deposited on Different Commercial Supports Precoated with $La_2O_3$," Ind Eng Chem Res 37:2142-2141, 1998.
Choudhary et al., "Oxidative conversion of methane/natural gas into higher hydrocarbons," Catalysis Surveys from Asia 8:15-25, 2004.
Choudhary et al., "Surface Basicity and Acidity of Alkaline Earth-Promoted $La_2O_3$ Catalysts and Their Performance in Oxidative Coupling of Methane," J. Chem. Technol. Biotechnol. 72:125-130, 1998.
Choudhary, et al., "Aromatization of dilute ethylene over Ga-modified ZSM-5 type zeolite catalysts," Microporous and Mesoporous Materials 47:253-267, 2001.
Christopher et al., "Engineering Selectivity in Heterogeneous Catalysis: Ag Nanowires as Selective Ethylene Epoxidation Catalysts," J Am. Chem. Soc. 130:11264-11265, 2008.
Cizeron et al., "Catalysts for Petrochemical Catalysis," filed May 24, 2011, U.S. Appl. No. 61/489,651, 86 pages.
Cizeron et al., "Catalysts for Petrochemical Catalysis," filed Nov. 29, 2011, for U.S. Appl. No. 61/564,832, 178 pgs.
Cizeron et al., "Catalytic Forms and Formulations," filed May 23, 2013, for U.S. Appl. No. 13/901,319, 132 pages.
Cizeron et al., "Catalysts for Petrochemical Catalysis," U.S. Appl. No. 14/692,495, filed Apr. 21, 2015, 211 pages.
Dai, "Study on low temperature catalytic activation of methane," Thesis of graduate student for Master's Degree in Physical Chemistry, East China Normal University, May 2005, 8 pages.
Débart et al., "α-$MnO_2$ Nanowires: A Catalyst for the $O_2$ Electrode in Rechargeable Lithium Batteries," Angew. Chem. Int. Ed. 47:4521-4524, 2008.
Dedov et al., "Oxidative coupling of methane catalyzed by rare earth oxides Unexpected synergistic effect of the oxide mixtures," Applied Catalysis 245:209-220, 2003,.
Devi et al., "College Inorganic Chemistry," Devi, K.V.S. Laxmi, Patel, N.C., and Venkatachalam, A.. College Inorganic Chemistry. Mumbai, IND: Himalaya Publishing House, 2010. Jan. 1, 2010 , XP055242276, Retrieved fron the Internet: URL:http://site.ebrary.com/lib/epo/reader.action?docID=10415159 [retried on Jan. 18, 2016] the whole document.
Dixon et al. "Advances in selective ethylene trimerisation—a critical overview" J. Organometallic Chem. 659:3641-3668, 2004.
Dulai et al. "N,N'-Bisdiaminophenylphosphine Ligands for Chromium-Catalyzed Selective Ethylene Oligomerization Reactions" Organometallics 30:935-941, 2011.
Enger et al., "A review of catalytic partial oxidation of methane to synthesis gas with emphasis on reaction mechanisms over transition metal catalysts," Applied Catalysis A: General 346:1-27, 2008.

Eskendirov et al., "Methane oxidative coupling on the $Au/La_2O_3/CaO$ catalyst in the presence of hydrogen peroxide," Catalysis Letters 35:33-31, 1995.
Fallah et al., "A New Nano-($2Li_2O/MgO$) Catalyst/Porous Alpha-Alumina Composite for the Oxidative Coupling of Methane Reaction" AIChE Journal 56:717-128, 2010.
Ferreira et al., "Effect of Mg, Ca and Sr on $CeO_2$ Based Catalysts for the Oxidative Coupling of Methane: Investigation on the Oxygen Species Responsible for Catalytic Performance," Industrial & Engineering Chemistry Research 51:10535-10541, 2012.
Freer et al., "Catalysts for Natural Gas Processes" U.S. Appl. No. 14/856,177, filed Sep. 16, 2015, 183 pages.
Galadima et al. "Revisiting the oxidative coupling of methane to ethylene in the golden period of shale gas: A review" J Ind Eng Chem . http://dx.doi.org/10.1016/j.jiec.2016.03.027.
Gao et al., "A study on methanol steam reforming to $CO_2$ and $H_2$ over the $La_2CuO_4$ nanofiber catalyst," Journal of Solid State Chemistry 181:1-13, 2008.
Gao et al., "The direct decomposition of NO over the $La_2CuO_4$ nanofiber catalyst," Journal of Solid State Chemistry 181:2804-2807, 2008.
Gong et al., "Preparation of Carbon Nanotubes—Cordierite Monoliths of Catalytic Chemical Vapor Deposition as Catalyst Supports for Ammonia Synthesis," Catalysis Letters 122:287-294, 2008.
Guo et al., "Direct, Nonoxidative Conversion of Methane to Ethylene, Aromatics, and Hydrogen" Science 344:616-619, 2014.
Hess et al., "Kirk-Othmer encyclopedia of chemical technology." New York, John Wiley & Sons Ltd., 1998, p. 171.
Hinson et al., "The Oxidative Coupling of Methane On Chlorinated Lithium-Doped Magnesium Oxide" J Chem Soc, Chem Comm 20:1430-1432, 1991.
Huang et al., "Exploiting Shape Effects of $La_2O_3$ Nanocatalysts for Oxidative Coupling of Methane Reaction," The Royal Society of Chemistry, 2013. (5 pages).
Huang et al., "Exploiting Shape Effects of La2O3 Nanocatalysts for Oxidative Coupling of Methane Reaction," The Royal Society of Chemistry, 2013, (7 pages).
Istadi et al., "Synergistic effect of catalyst basicity and reducibility on performance of ternary CeO2-based catalyst for CO2 OCM to C2 hydrocarbons," Journal of Molecular Catalysis A:Chemical 259:61-66, 2006.
Jaramillo et al., "Comparative Analysis of the Production Costs and Life-Cycle GHG Emissions of FT Liquid Fuels from Coal and Natural Gas" Env. Sci. Tech 42:1559-1565, 2008.
Jiangrong et al., "Preparation and Characterization of $La_2O_2CO_3$ Nanowires with High Surface Areas," Journal of The Chinese Rare Earth Society 23:33-36, 2005.
Kaminsky et al. "Deactivation of Li-Based Catalysts for Methane Oxidative Coupling" Symposium on Natural Gas Upgrading II, Presented before The Division of Petroleum Chemistry, Inc., The American Chemical Society, San Francisco, CA, Apr. 5-10, 1992,.
Kaminsky et al., "Oxygen X-Ray Absorption Near-Edge Structure Characterization of the Ba-Doped Yttria Oxidative Coupling Catalyst" J Catalysis 136:16-23, 1992.
Keller et al., "Synthesis of Ethylene via Oxidative Coupling of Methane," Journal of Catalysis 73:9-19, 1982.
Krishnadas et al., "Pristine and Hybrid Nickel Nanowires: Template-, Magnetic Field-, and Surfactant-Free Wet Chemical Synthesis and Raman Studies," The Journal of Physical Chemistry 115:4483-4490, 2011.
Kuang et al., "Grafting of PEG onto lanthanum hydroxide nanowires," Materials Letters 62:4018-4080, 2008.
Labinger, "Oxidative Coupling of Methane: An Inherent Limit to Selectivity?" Catalysis Letters 1:371-376, 1988.
Li et al., "Color control and white light generation of upconversion luminescence by operating dopant concentrations and pump densities in $YB^{3+}$, $Er^{3+}$ and Tm3+ tri-doped $Lu_2O_3$ nanocrystals," J. Mater. Chem. 21:2895-2900, 2011.
Ling et al., "Preparation of $Ag_{core}Au_{shell}$ Nanowires and Their Surface Enhanced Raman Spectroscopic Studies," Acta Chimica Sinica 65:779-784, 2007.

(56) References Cited

OTHER PUBLICATIONS

Liu et al., "A novel $Na_2WO_4$-Mn/SiC monolithic foam catalyst with improved thermal properties for the oxidative coupling of methane," Catalysis Communications 9:1302-1306, 2007.
Lunsford, "The Catalytic Oxidative Coupling of Methane," Angew. Chem. Int. Ed. Engl. 34:910-980, 1995.
Ma et al., "Processing and properties of carbon nanotubes-nano-SiC ceramic," Journal of Materials Science 33:5243-5246, 1998.
Matskevich et al., "Synthesis and thermochemistry of new phase $BaCe_{0.7}Nd_{0.2}In_{0.1}O_{2.85}$," Journal of Alloys and Compounds 577:148-151, 2013.
Miller et al., "Oxidation reactions of ethane over Ba-Ce-O based perovskites," Applied Catalysis A 201:45-54, 2000.
Mleczko et al., "Catalytic oxidative coupling of methane—reaction engineering aspects and process schemes," Fuel Processing Technology 42:217-248, 1995.
Nagamoto et al., "Methane Oxidation over Perovskite-type Oxide Containing Alkaline-earth Metal," Chemistry Letters, 237-240, 1988.
Nam et al., "Virus-Enabled Synthesis and Assembly of Nanowires for Lithium Ion Battery Electrodes," Science 312:885-888, 2006.
Natural Gas Spec Sheet, prepared by Florida Power and Light Company, 2003.
Neltner et al., "Production of Hydrogen Using Nanocrystalline Protein-Templated Catalysts on M13 Phage," ACSNano 4:3227-3235, 2010.
Neltner, "Hybrid Bio-templated Catalysts," Doctoral Thesis, Massachusetts Institute of Technology, Jun. 2010, 156 pages.
Nyce et al., "Polymer Templated Nanowire Catalysts," filed Nov. 29, 2011 for U.S. Appl. No. 61/564,836, 317 pgs.
Nyce et al., "Integrated Processes and Systems for Conversion of Methane To Multiple Higher Hydrocarbon Products," U.S. Appl. No. 14/099,614, filed Dec. 6, 2013, 67 pages.
O'Connor et al. "Alkene Oligomerization" Catalysis Today 6:329-349, 1990.
Pak et al., "Elementary Reactions in the Oxidative Coupling of Methane over $Mn/Na_2WO_4/SiO_2$ and $Mn/Na_2WO_4/MgO$ Catalysts," Journal of Catalysis 179:222-230, 1998.
Park et al., "Fabrication of metallic nanowires and nanoribbions using laser interference lithography and shadow lithography," Nanotechnology 21:1-6, 2010.
Peitz et al., "An Alternative Mechanistic Concept for Homogeneous Selective Ethylene Oligomerization of Chromium-Based Catalysts: Binuclear Metallacycles as a Reason for 1-Octene Selectivity?" Chemistry—A European Journal 16.7670-7676, 2010.
Qiu et al., "Steady-state conversion of methane to aromatics in high yields using an integrated recycle reaction system," Catalysis Letters 48:11-15, 1997.
Ren et al., "Basic petrochemicals from natural gas, coal and biomass: Energy use and $CO_2$ emissions" Res Conserv Recycl 53:513-528, 2009.
Ryu et al., "Preparation of Porous $LaFeO_3$ Nanowires using AAO Template and Their Catalytic Properties," Bull. Korean Chem Soc. 32:2457-2460, 2011.
Schaarschmidt et al., "Ferrocenyl phosphane nickel carbonyls: Synthesis, solid state structure, and their use as catalysts in the oligomerization of ethylene" J. Organometallic Chem. 695:1541-1549, 2010.
Schammel et al., "Catalysts for Petrochemical Catalysis," U.S. Appl. No. 14/777,333, filed Sep. 15, 2015, 259 pages.
Schammel et al., "Heterogeneous Catalysts," U.S. Appl. No. 14/701,963, filed May 1, 2015, 335 pages.
Schammel et al., "Catalysts for Petrochemical Catalysis," U.S. Appl. No. 61/794,486, filed Mar. 15, 2013, 217 pages.
Schammel et al., "Oxidative Coupling of Methane Systems and Methods," U.S. Appl. No. 13/900,898, filed May 23, 2013, 201 pages.
Schweer et al., "OCM in a fixed-bed reactor: limits and perspectives," Catalysis Today 21:357-369, 1994.
Somorjai et al., "High technology catalysts towards 100% selectivity Fabrication, characterization and reaction studies," Catalysis Today 100:201-215, 2005.
Song et al., "Synthesis, characterization and ethylene oligomerization behaviour of 8-quinaldinylnickel dihalides" Catal. Sci. Technol. 1:69-75, 2011.
Spinicci et al., "Oxidative coupling of methane on $LaAlO_3$ perovskites partially substituted with alkali or alkali-earth ions," Journal of Molecular Catalysis A; Chemical 176:253-265, 2001.
Takanabe et al., "Mechanistic Aspects and eaction Pathways for Oxidative Coupling of Methane on $Mn/Na_2WO_4/SiO_2$ Catalysts," J. Phys. Chem. C 113:10131-10145, 2009.
Takanabe et al., "Rate and Selectivity Enhancements Mediated by OH Radicals in the Oxidative Coupling of Methane Catalyzed by $Mn/Na_2WO_4/SiO_2$," Angew. Chem. Int. Ed. 47:7689-7693, 2008.
Tana et al., "Morphology-dependent redox and catalytic properties of $CeO_2$ nanostructures: Nanowires, nanorods and nanoparticles," Catalysis Today 148:179-183, 2009.
Tanaka et al., "Oxidative Coupling of Methane over Ba-incorporated $LaInO_3$ Perovskite Catalyst," Journal of the Japan Petroleum Institute 55:71-72, 2012.
Taylor et al., "Lanthanum Catalysts for $CH_4$ Oxidative Coupling: A Comparison of the Reactivity of Phases," Ind. Eng. Chem. Res. 30:1016-1023, 1991.
Teymouri et al., "Reactivity of perovskites on oxidative coupling of methane," Journal of Materials Science 30:3005-3009, 1995.
Theuerkauf et al., "Analysis of particle porosity distribution in fixed beds using the discrete element method," Powder Technology 165:92-99, 2006.
Tian et al., "Catalytic reduction of $Nos_x$ with $NH_3$ over different-shaped $MnO_2$ at low temperature," Journal of Hazardous Materials 188:105-109, 2011.
Tomishige et al., "Reactivity and characterization of absorbed oxygen on $SrTi_{1-x}Mg_xO_{3-\delta}$ catalysts for oxidative coupling of methane," Phys. Chem. Chem. Phys. 1:3039-3045, 1999.
Tong et al., "Development Strategy Research of Downstream Products of Ethene in Tianjin," Tianjin Economy, pp. 37-40, 1996.
Trautmann et al., "Cyrogenic Technology for Nitrogen Rejection from Variable Content Natural Gas," XIV Convencion Internacional de Gas, Caracas, Venezuela May 10-12, 2000.
Tullo, "Ethylene from Methane," Chemical and Engineering News 89:20-21, 2011.
Valenzuela et al., "Nanostructured ceria-based catalysts for oxydehydrogenation of ethane with $CO_2$, " Topics in Catalysis 15:181-188, 2001.
Van Santen et al., "An Introduction To Molecular Heterogeneous Catalysis" New Trends in Material Chemistry, pp. 345-362, 1997.
Wang et al., "Autothermal oxidative coupling of methane on the SrCO3/Sm2O3 catalysts," Catalysis Communications 10:807-810, 2009.
Wang et al., "Low-temperature selective oxidation of methane to ethane and ethylene over BaCO3/La2O3 catalysts prepared by urea combustion method," Catalysis Communications 7:59-63, 2006.
Wang et al., "Nanostructured Sheets of Ti-O Nanobelts for Gas Sensing and Antibacterial Applications, " Advanced Functional Materials 18:1131-1137, 2008.
Wang et al., "Synthesis and Characterization of Lanthanide Hydroxide Single-Crystal Nanowires" Angew Chem Int Ed 41:4790-4793, 2002.
Wang et al., "Comparative study on oxidation of methane to ethane and ethylene over $Na_2WO_4$-$Mn/SiO_2$ catalysts prepared by different methods," Journal of Molecular Catalysis A: Chemical 245:272-277, 2006.
Wong et al., "Oxidative Coupling of Methane Over Alkali Metal Oxide Promoted $LA_2O_3/BACO_3$ Catalysts," Journal of Chemical Technology and Biotechnology 65:351-354, 1996.
Yang et al., "Anisotropic syntheses of boat-shaped core-shell Au-Ag nanocrystals and nanowires," Nanotechnology 17:2304-2310, 2006.
Yu et al., "Oxidative Coupling of Methane over Acceptor-doped $SrTiO_3$: Correlation between p-type Conductivity and $C_2$ Yield," Journal of Catalysis 13:338-344, 1992.

(56) References Cited

OTHER PUBLICATIONS

Yun et al., "Current Status and Some Perspectives of Rare Earth Catalytic Materials," *Journal of The Chinese Rare Earth Society* 25:1-15, 2007.
Zhang et al., "Relationship between packing structure and porosity in fixed beds of equilateral cylindrical particles," *Chemical Engineering Science* 61:8060-8074, 2006.
Zhang et al., "Single-Walled Carbon Nanotube-Based Coaxial Nanowires: Synthesis, Characterization, and Electrical properties," *J Phys Chem* 109(3) 1101-1107, 2005.
Zhang et al., "Recent Progress in Direct Partial Oxidation of Methane to Methanol," *Journal of Natural Gas Chemistry* 12:81-89, 2003.
Zhao, "Technologies and Catalysts for Catalytic Preparation of Ethene," *Industrial Catalysis* 12:285-289, 2004.
Zhou et al., "Functionalization of lanthanum hydroxide nanowires by atom transfer radical polymerization," *Nanotechnology* 18:405704, 2007.
Zhu et al. "Recent Research Progress in Preparation of Ethylene Oligomers with Chromium-Based Catalytic Systems" *Designed Monomers & Polymers* 14:1-23, 2011.
Zimmermann et al., "Ethylene," *Ullmann's Encyclopedia of Industrial Chemistry*, Wiley-VCH Verlag GmbH & Co. KGaA, Weinheim, Germany, 2009, (66 pages).
Zurcher et al., "Nanowire Catalysts," filed May 24, 2012, for U.S. Appl. No. 61/651,399, 406 pages.
Zurcher et al., "Nanowire Catalysts," filed Nov. 29, 2011, for U.S. Appl. No. 61/564,834, 367 pages.
U.S. Appl. No. 11/000,835, filed May 11, 2021.
U.S. Appl. No. 11/078,132, filed Aug. 3, 2021.

\* cited by examiner

CATALYTIC FORMS AND FORMULATIONS

BACKGROUND

Technical Field

This invention is generally related to catalytic forms and formulations and, more specifically, to catalytic forms and formulations useful in a variety of catalytic reactions, such as the oxidative coupling of methane.

Description of the Related Art

Catalysis is the process in which the rate of a chemical reaction is either increased or decreased by means of a catalyst. Positive catalysts increase the speed of a chemical reaction, while negative catalysts slow it down. Substances that increase the activity of a catalyst are referred to as promoters or activators, and substances that deactivate a catalyst are referred to as catalytic poisons or deactivators. Unlike other reagents, a catalyst is not consumed by the chemical reaction, but instead participates in multiple chemical transformations. In the case of positive catalysts, the catalytic reaction generally has a lower rate-limiting free energy change to the transition state than the corresponding uncatalyzed reaction, resulting in an increased reaction rate at the same temperature. Thus, at a given temperature, a positive catalyst tends to increase the yield of desired product while decreasing the yield of undesired side products. Although catalysts are not consumed by the reaction itself, they may be inhibited, deactivated or destroyed by secondary processes, resulting in loss of catalytic activity.

Catalysts are generally characterized as either heterogeneous or homogeneous. Heterogeneous catalysts exist in a different phase than the reactants (e.g., a solid metal catalyst and gas phase reactants), and the catalytic reaction generally occurs on the surface of the heterogeneous catalyst. Thus, for the catalytic reaction to occur, the reactants must diffuse to and/or adsorb onto the catalyst surface. This transport and adsorption of reactants is often the rate limiting step in a heterogeneous catalysis reaction. Heterogeneous catalysts are also generally easily separable from the reaction mixture by common techniques such as filtration or distillation.

One heterogeneous catalytic reaction with commercial potential is the oxidative coupling of methane ("OCM") to ethylene: $2CH_4+O_2 \rightarrow C_2H_4+2H_2O$. See, e.g., Zhang, Q., *Journal of Natural Gas Chem.*, 12:81, 2003; Olah, G. "Hydrocarbon Chemistry", Ed. 2, John Wiley & Sons (2003). This reaction is exothermic ($\Delta H=-67$ kcals/mole) and has typically been shown to occur at very high temperatures (>700° C.). Although the detailed reaction mechanism is not fully characterized, experimental evidence suggests that free radical chemistry is involved. (Lunsford, *J. Chem. Soc., Chem. Comm.*, 1991; H. Lunsford, *Angew. Chem., Int. Ed. Engl.*, 34:970, 1995). In the reaction, methane ($CH_4$) is activated on the catalyst surface, forming methyl radicals which then couple in the gas phase to form ethane ($C_2H_6$), followed by dehydrogenation to ethylene ($C_2H_4$). To date, the OCM reaction has not been commercialized, due in large part to the lack of effective catalysts and catalytic forms.

The use of heterogeneous catalysts, for example in the OCM reaction, presents a number of challenges, especially on a commercial scale. Commercial catalytic processes must be able to achieve a high conversion of the reactant (e.g., hydrocarbon) feedstock at high gas hourly space velocities. However, when a fixed bed of heterogeneous catalyst is used, the pressure drop across the catalytic bed prevents operation under the high gas space velocities demanded of a commercial operation. In addition, many commercially important catalytic reactions, such as OCM, are exothermic and controlling the exotherm (i.e., hotspots) within the catalytic bed can be difficult. Finally, many commercially important heterogeneous catalysts contain expensive and/or rare metals, so methods to reduce the amount of catalyst used for a given process are generally desirable.

To address these challenges, many heterogeneous catalysts are employed in combination with a binder, carrier, diluent and/or support material. The use of these materials provides certain advantages. For example, supports provide a surface on which the catalyst is spread to increase the effective surface area of the catalyst and reduce the catalyst load required. The support or diluent may also interact synergistically with the catalyst to enhance the catalytic properties of the catalyst. Further, catalytic supports may be tailored to specific reactions and/or reactor types in order to optimize the flow (e.g., reduce back pressure) of gaseous reactants.

While some catalytic binders, carriers, supports and diluents are known, there remains a need in the art for improved catalyst forms and formulations and, more specifically, a need for novel approaches to design of catalytic materials for optimizing catalyzed reactions. In particular there is a need for improved catalytic materials capable of controlling exotherms, improving yield and selectivity and controlling back pressure in a catalytic reaction, for example the oxidative coupling of methane. The present invention fulfills these needs and provides further related advantages.

BRIEF SUMMARY

In brief, catalytic forms and formulations and related methods are disclosed. In one embodiment, the disclosure provides a catalytic material comprising a plurality of catalysts in combination with a diluent or support, for example in some embodiments the catalysts are catalytic nanowires. The catalytic materials find utility in various catalytic reactions. In one particular embodiment, the catalytic materials are useful for petrochemical catalysis, such as the oxidative coupling of methane.

In other embodiments, the invention is directed to a catalytic material comprising a plurality of catalytic nanowires in combination with a diluent, wherein the diluent comprises an alkaline earth metal compound, silicon carbide, cordierite, $B_2O_3$, $In_2O_3$, $SrAl_2O_4$, $B_4SrO_7$ or combinations thereof. In certain embodiments, the alkaline earth metal compound is not MgO, CaO, $MgAl_2O_4$ or calcium aluminate. For example in some aspects the alkaline earth metal compound is $MgCO_3$, $MgSO_4$, $Mg_3(PO_4)_2$, $CaCO_3$, $CaSO_4$, $Ca_3(PO_4)_2$, $CaAl_2O_4$, SrO, $SrCO_3$, $SrSO_4$, $Sr_3(PO_4)_2$, $SrAl_2O_4$, BaO, $BaCO_3$, $BaSO_4$, $Ba_3(PO_4)_2$, $BaAl_2O_4$ or combinations thereof. In some other aspects the alkaline earth metal compound is SrO, $MgCO_3$, $CaCO_3$, $SrCO_3$ or combinations thereof.

In other embodiments of the foregoing, the catalytic material is in the form of a formed aggregate comprising a catalyst and optional diluent, and may be provided in any of a variety of shapes and forms. The formed aggregates include monoliths and aggregates formed by any number of methods known in the art, such as extrudates and pressed, cast or molded articles. For example, the catalytic material may comprise a form in a shape selected from a cylinder or rod, that may optionally include ribbing, honeycomb or a star shaped cross section, a trilobe cross section, or any of a variety of other cross sectional shapes, or it may include a segmented portion of such aggregate forms, e.g., as disks, stars, trilobes, and the like. Alternatively or additionally, the formed aggregate may be or may comprise a portion that is hollow, such as a tube, donut, or ring-shaped form. In still other aspects, the formed aggregate may comprise a formed shape, such as a cup or bowl shape, a round or oval tablet, a spherical shape, or irregular shape. In still other embodiments, the catalytic material is disposed on, impregnated in, or combinations thereof, a monolith, a foam, foil, gauze or honeycomb structure.

In yet other embodiments, the catalytic material comprises a surface area ranging from 0.1 to 200 $m^2/g$, or from about 1 to 50 $m^2/g$, but may also have much lower surface area, e.g., between about 0.0001 $m^2/g$ and 0.1 $m^2/g$, or higher, between about 200 $m^2/g$ and 2000 $m^2/g$ and in other embodiments the catalytic material comprises a pore volume fraction (i.e., the fraction of the total volume residing in pores) ranging from 5% to 90% or from about 20 to 90%. In other examples, the weight ratio of catalyst (e.g., catalytic nanowire) to total diluent and support ranges from 95:5 to 5:95.

In still other examples of the foregoing, the diluent comprises a dopant which promotes catalytic activity of the catalytic nanowires. For example, in some embodiments the dopant promotes catalytic activity of the catalytic nanowires in the OCM reaction.

In other aspects, the invention is directed to a catalytic material comprising a plurality of catalytic nanowires and a sacrificial binder.

In still other embodiments, the present disclosure provides a catalytic material in the form of a formed aggregate, wherein the catalytic material comprises a plurality of catalytic nanowires and substantially no binder material. In certain other embodiments, the catalytic material comprises a combined total of less than 1% w/w of binder and diluent. In even other embodiments, the catalytic material comprises no binder and no diluent.

In other embodiments, a catalytic material comprising an active catalyst and a nanowire binder is provided. In some further embodiments, the active catalyst is a bulk catalyst, and in other embodiments the active catalyst is a catalytic nanowire. In yet other embodiments, the active catalyst is a zeolite catalyst.

Other exemplary catalytic materials include a catalytic material in the form of formed aggregate, wherein the catalytic material comprises a plurality of catalytic nanowires and a diluent. For example, the formed aggregate may be in the form of an extrudate, a pressed particle, a cast particle or a monolith. In some embodiments, the catalytic material comprises pores greater than 20 nm in diameter.

In other embodiments the catalytic material is in the form of n formed aggregate having a shape selected from a cylinder, rod, star, ribbed, trilobe, hollow, donut, ring-shaped, pellet, tube, spherical, honeycomb and an irregular shape. In other embodiments, the formed aggregate comprises an inner core and an outer layer, and in some embodiments greater than 95% of the catalytic nanowires reside in the inner core. In still other embodiments, the outer layer is oxygen permeable. In other embodiments, greater than 95% of the catalytic nanowires reside in the outer layer. In any of the foregoing embodiments, the formed aggregate is an extrudate.

In still other embodiments of the foregoing catalytic material in the form of a formed aggregate the diluent comprises $Al_2O_3$, $SiO_2$, $TiO_2$, MgO, CaO, SrO, BaO, $ZrO_2$, ZnO, $LiAlO_2$, $MgAl_2O_4$, MnO, $MnO_2$, $Mn_3O_4$, $La_2O_3$, $AlPO_4$, $SiO_2/Al_2O_3$, $B_2O_3$, $Ga_2O_3$, $In_2O_3$, $SrAl_2O_4$, $B_4SrO_7$, $CaCO_3$, $SrCO_3$, activated carbon, silica gel, zeolites, activated clay, activated $Al_2O_3$, SiC, diatomaceous earth, aluminosilicates, calcium aluminate, barium aluminate, $CeO_2$, sulfates, support nanowires, carbides, boron-carbide, silicon carbide, a nitride, a carbonates, ammonium carbonate, a silicates, aluminates or combinations thereof. In some embodiments, the catalytic material comprises a surface area ranging from 1 to 50 $m^2/g$, and in other embodiments the catalytic material comprises a pore volume fraction ranging from 20 to 90%.

In more embodiments of the foregoing catalytic material in the form of a formed aggregate, the weight ratio of catalytic nanowire to total diluent and support ranges from 95:5 to 5:95. In other embodiments, the diluent comprises a dopant which promotes catalytic activity of the catalytic nanowires. For example, in certain embodiments the dopant promotes catalytic activity of the catalytic nanowires in the OCM reaction.

Still other aspects of the present invention are directed to a catalytic material comprising a plurality of catalytic nanowires supported on or in a structured support. In some embodiments, the structured support comprises a foam, foil, gauze or honeycomb structure. In other embodiments, the structured support comprises silicon carbide or alumina, and in other examples the structured support comprises a metal foam, ceramic foam, silicon carbide foam, alumina foam, corrugated metal foil or extruded ceramic honeycomb.

In other embodiments of the catalytic material comprising a plurality of catalytic nanowires supported on or in a structured support, the catalytic nanowires are disposed on the structured support. For example, in some embodiments the catalytic nanowires form a layer on an outer surface of the structured support, the layer having a thickness ranging from 1 to 10 microns. In other embodiments, the catalytic nanowires are impregnated in the structured support.

In still other embodiments of the catalytic material comprising a plurality of catalytic nanowires supported on or in a structured support, the structured support is a monolith. For example, in some embodiments the monolith comprises gas permeable walls. In other embodiments, the gas permeable walls are oxygen permeable. In other embodiments, the monolith comprises a plurality of flow channels, for example the monolith may comprise active flow channels and inactive flow channels, wherein the active flow channels comprise catalytic nanowires and the inactive flow channels comprise substantially no catalytic nanowires. In still other examples, from 5-75% of the flow channels are inactive flow channels, and in other embodiments the flow channels are configured to direct a gas flow through alternating active and inactive flow channels.

In yet other embodiments of the catalytic material comprising a plurality of catalytic nanowires supported on or in a structured support, the structured support comprises a dopant which promotes catalytic activity of the catalytic nanowires. For example, in some embodiments the dopant promotes catalytic activity of the catalytic nanowires in the OCM reaction.

In other embodiments of the present invention, a catalytic material comprising a first and second catalyst, wherein the first and second catalysts have a different catalytic activity in the same reaction under the same conditions is provided. For example, in some embodiments the first catalyst is a nanowire catalyst, and in other embodiments the second catalyst is a bulk catalyst. In other various embodiments, each of the first and second catalysts are nanowire catalysts, and in other embodiments each of the first and second catalysts are bulk catalysts.

In other embodiments of the foregoing catalytic material comprising a first and second catalyst, the second catalyst has a lower catalytic activity than the first catalyst under the same conditions. In other embodiments, the catalytic activity of the second catalyst increases with increasing temperature. In still other embodiments, the reaction is OCM.

In other aspects, the present invention is directed to a catalytic material having a single pass methane conversion of greater than 10%, greater than 15%, greater than 20% or even greater than 25% when the catalytic material is employed as a catalytic material in the oxidative coupling of methane at inlet reactor temperatures of 750° C. or less, for example temperatures of less than 650° C. or even temperatures of less than 600° C.

In other exemplary embodiments, the invention provides a catalytic material comprising a catalytic nanowire, wherein the catalytic material is in contact with a reactor. In some embodiments, the reactor is used for performing OCM. In other aspects, the catalytic material comprises silicon carbide. In still other embodiments, the reactor is a fixed bed reactor, and in some embodiments, the reactor comprises an inner diameter of at least 1 inch.

In other embodiments, the invention is directed to a catalytic material comprising at least one $O_2$-OCM catalyst and at least one $CO_2$-OCM catalyst. For example, in some embodiments at least one of the $O_2$-OCM catalyst or the $CO_2$-OCM catalyst is a catalytic nanowire.

In other embodiments, the present disclosure provides a catalytic material comprising at least one $O_2$-OCM catalyst and at least one $CO_2$-ODH catalyst. In some embodiments, at least one of the $O_2$-OCM catalyst or the $CO_2$-ODH catalyst is a catalytic nanowire.

In other aspects of any of the foregoing catalytic materials, the catalytic material comprises a void fraction volume of about 35% to about 70%, for example in some embodiments the void fraction volume ranges about 45% to about 65%. In other embodiments of the foregoing, the catalytic material comprises catalyst particles having a cross sectional dimension in at least one dimension ranges from about 1 mm to about 20 mm, for example from about 2 mm to about 10 mm.

In still other embodiments of any of the foregoing, the catalytic material comprises catalyst particles having a surface area to volume ratio ranging from about 0.1 $mm^{-1}$ to about 10 $mm^{-1}$, for example from about 0.1 $mm^{-1}$ to about 5 $mm^{-1}$. In related aspects of any of the foregoing, the catalytic material comprises a crush strength greater than about 1 $N/mm^2$, such as about 10 $N/mm^2$.

In more embodiments of any of the foregoing catalytic materials, the catalytic material comprises a porosity of between about 10% and about 80% or between about 40% and about 60%.

In other embodiments of any of the foregoing catalytic materials, the ratio of the surface area of the catalytic form envelope to the volume of the catalytic form envelope ranges from about 0.5 $mm^{-1}$ to about 4 $mm^{-1}$. In certain other embodiments, the catalytic material comprises a homogenously dispersed active catalyst. In more embodiments of any of the foregoing, the catalytic material comprises a surface area ranging from about 1 $m^2/g$ to about 50 $m^2/g$.

In still other embodiments, the present invention includes a reactor comprising a catalytic bed, the catalytic bed comprising an inlet end, an outlet end, and a catalytic material comprising an active catalyst and a diluents disposed within the catalytic bed, wherein the catalytic bed comprises a concentration gradient of the active catalyst, wherein the concentration of active catalyst is greater at the inlet end than the outlet end. In some embodiments, the active catalyst is an OCM active catalyst. In other embodiments, the concentration gradient of active catalyst is selected such that a temperature change from the inlet end to the outlet end is not greater than 450° C. when the reactor is employed for the oxidative coupling of methane. In other embodiments, the concentration gradient of active catalyst is selected such that a temperature change from the inlet end to the outlet end is not greater than 200° C. when the reactor is employed for the oxidative coupling of methane.

In still other embodiments, the invention is directed to any of the catalytic materials or reactors described herein, wherein the catalytic material comprises an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof.

In other embodiments, the invention is directed to any of the catalytic materials or reactors described herein, wherein the catalytic material comprises an inorganic catalytic nanowire having a ratio of effective length to actual length of one and an aspect ratio of greater than ten as measured by TEM in bright field mode at 5 keV In other embodiments, the invention provides a method for preparing a catalytic material, the method comprising admixing a plurality of catalytic nanowires with a sacrificial binder and removing the sacrificial binder to obtain a catalytic material comprising substantially no binder material and having an increased microporosity compared a to catalytic material prepared without the sacrificial binder.

In some other embodiments, the present disclosure provides a method for the oxidative coupling of methane, the method comprising converting methane to one or more C2 hydrocarbons in the presence of a catalytic material, wherein the catalytic material comprises at least one $O_2$-OCM catalyst and at least one $CO_2$-OCM catalyst. In some embodiments, at least one of the $O_2$-OCM catalyst or the $CO_2$-OCM catalyst is a catalytic nanowire. In other embodiments, the catalytic material comprises a bed of alternating layers of $O_2$-OCM catalysts and $CO_2$-OCM catalysts. In yet other embodiments, the catalytic material comprises a homogeneous mixture of $O_2$-OCM catalysts and $CO_2$-OCM catalysts.

In still other embodiments, a method for the preparation of ethylene is provided, the method comprises converting methane to ethylene in the presence of a catalytic material, wherein the catalytic material comprises at least one $O_2$-OCM catalyst and at least one $CO_2$-ODH catalyst. In some embodiments, at least one of the $O_2$-OCM catalyst or the $CO_2$-OCM catalyst is a catalytic nanowire.

In yet other embodiments, the invention includes a method for the oxidative coupling of methane, the method comprising contacting any of the catalytic materials described herein with a mixture comprising methane and oxygen.

In yet other embodiments, the present disclosure provides a method for the preparation of ethane or ethylene, the method comprising contacting any of the catalytic materials reactors described herein with a mixture comprising methane and oxygen.

In still other embodiments, the invention is directed to a method for the preparation of a downstream product of ethylene, the method comprising oligomerizing ethylene, wherein the ethylene had been prepared by a method comprising contacting any of the catalytic materials or reactors described herein with a mixture comprising methane and oxygen.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE SEVERAL VIEWS OF THE DRAWINGS

In the drawings, the sizes and relative positions of elements in the drawings are not necessarily drawn to scale. For example, the various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

DETAILED DESCRIPTION OF THE INVENTION

Figure 1C:
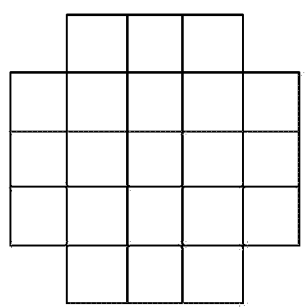
FIGS. 1A-1E depict a monolith containing void and active channels.
Figure 1B:
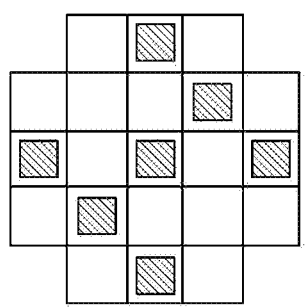
Figure 1E:
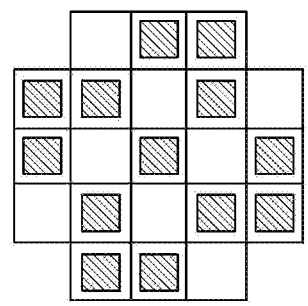

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Definitions

As used herein, and unless the context dictates otherwise, the following terms have the meanings as specified below.

"Catalyst" means a substance that alters the rate of a chemical reaction. A catalyst may either increase the chemical reaction rate (i.e., a "positive catalyst") or decrease the reaction rate (i.e., a "negative catalyst"). Catalysts participate in a reaction in a cyclic fashion such that the catalyst is cyclically regenerated. "Catalytic" means having the properties of a catalyst.

"Catalytic material" refers to a plurality of catalyst particles, which may optionally be combined with a support, diluent and/or binder.

"Catalyst form" or "catalytic form" refers to the physical shape of a catalytic material. For example, catalyst forms include catalysts in the shape of extrudates or pellets or disposed on various support structures, including honeycomb structures, grids, monoliths, and the like, as discussed in more detail below.

"Catalyst formulation" or "catalytic formulation" refers to the chemical composition of a catalytic material. For example, a catalyst formulation may include a catalyst and one or more support, diluent and/or binder materials.

An "extrudate" refers to a material (e.g., catalytic material) prepared by forcing a semisolid material comprising a catalyst through a die or opening of appropriate shape. Extrudates can be prepared in a variety of shapes and structures by common means known in the art.

A "formed aggregate" refers to an aggregation of catalyst material particles, either alone, or in conjunction with one or more other materials, e.g., catalyst materials, dopants, diluents, support materials, binders, etc. formed into a single particle. Formed aggregates include without limitation, extruded particles, termed "extrudates", pressed or cast particles, e.g., pellets such as tablets, ovals, spherical particles, etc., coated particles, e.g., spray, immersion or pan coated particles, impregnated particles, e.g., monoliths, foils, foams, honeycombs, or the like. Formed aggregates may range in size from particles having individual cross sections in the micron range to cross sections in the millimeter range, to even larger particles such as monolithic formed aggregates, that may be on the order of centimeters or even meters in cross section.

A "pellet" or "pressed pellet" refers to a material (e.g., catalytic material) prepared by applying pressure to (i.e., compressing) a material comprising a catalyst into a desired shape. Pellets having various dimensions and shapes can be prepared according to common techniques in the art.

"Monolith" or "monolith support" is generally a structure formed from a single structural unit preferably having passages disposed through it in either an irregular or regular pattern with porous or non-porous walls separating adjacent passages. Examples of such monolithic supports include, e.g., ceramic or metal foam-like or porous structures. The single structural unit may be used in place of or in addition to conventional particulate or granular catalysts (e.g., pellets or extrudates). Examples of such irregular patterned monolith substrates include filters used for molten metals. Monoliths generally have a porous fraction ranging from about 60% to 90% and a flow resistance substantially less than the flow resistance of a packed bed of similar volume (e.g., about 10% to 30% of the flow resistance of a packed bed of similar volume). Examples of regular patterned substrates include monolith honeycomb supports used for purifying exhausts from motor vehicles and used in various chemical processes and ceramic foam structures having irregular passages. Many types of monolith support structures made from conventional refractory or ceramic materials such as alumina, zirconia, yttria, silicon carbide, and mixtures thereof, are well known and commercially available from, among others, Corning, Iac.; Vesuvius Hi-Tech Ceramics, Inc.; and Porvair Advanced Materials, Inc. and SiCAT (Sicatalyst.com). Monoliths include foams, honeycombs, foils, mesh, gauze and the like.

"Nanowire" means a nanowire structure having at least one diameter on the order of nanometers (e.g. between about 1 and 100 nanometers) and an aspect ratio greater than 10:1. The "aspect ratio" of a nanowire is the ratio of the actual length (L) of the nanowire to the diameter (D) of the nanowire. Aspect ratio is expressed as L:D. Exemplary nanowires are known in the art and described in more detail in co-pending U.S. application Ser. No. 13/115,082 (U.S. Pub. No. 2012/0041246); U.S. Provisional Application Nos. 61/564,834 and 61/564,836; and U.S. Provisional Application entitled "Nanowire Catalysts", filed May 24, 2012, the full disclosures of which are hereby incorporated by reference in their entirety for all purposes.

"Polycrystalline nanowire" means a nanowire having multiple crystal domains. Polycrystalline nanowires generally have different morphologies (e.g. bent vs. straight) as compared to the corresponding "single-crystalline" nanowires.

"Effective length" of a nanowire means the shortest distance between the two distal ends of a nanowire as measured by transmission electron microscopy (TEM) in bright field mode at 5 keV. "Average effective length" refers to the average of the effective lengths of individual nanowires within a plurality of nanowires.

"Actual length" of a nanowire means the distance between the two distal ends of a nanowire as traced through the backbone of the nanowire as measured by TEM in bright field mode at 5 keV. "Average actual length" refers to the average of the actual lengths of individual nanowires within a plurality of nanowires.

The "diameter" of a nanowire is measured in an axis perpendicular to the axis of the nanowire's actual length (i.e. perpendicular to the nanowires backbone). The diameter of a nanowire will vary from narrow to wide as measured at different points along the nanowire backbone. As used herein, the diameter of a nanowire is the most prevalent (i.e. the mode) diameter.

The "ratio of effective length to actual length" is determined by dividing the effective length by the actual length. A nanowire having a "bent morphology" will have a ratio of effective length to actual length of less than one as described in more detail herein. A straight nanowire will have a ratio of effective length to actual length equal to one as described in more detail herein.

"Inorganic" means a substance comprising a metal or semi-metal element. In certain embodiments, inorganic refers to a substance comprising a metal element. An inorganic compound can contain one or more metals in their elemental state, or more typically, a compound formed by a metal ion ($M^{n+}$, wherein n 1, 2, 3, 4, 5, 6 or 7) and an anion ($X^{m-}$, m is 1, 2, 3 or 4), which balance and neutralize the positive charges of the metal ion through electrostatic interactions. Non-limiting examples of inorganic compounds include oxides, hydroxides, halides, nitrates, sulfates, carbonates, phosphates, acetates, oxalates, and combinations thereof, of metal elements. Other non-limiting examples of inorganic compounds include $Li_2CO_3$, $Li_2PO_4$, $LiOH$, $Li_2O$, $LiCl$, $LiBr$, $LiI$, $Li_2C_2O_4$, $Li_2SO_4$, $Na_2CO_3$, $Na_2PO_4$, $NaOH$, $Na_2O$, $NaCl$, $NaBr$, $NaI$, $Na_2C_2O_4$, $Na_2SO_4$, $K_2CO_3$, $K_2PO_4$, $KOH$, $K_2O$, $KCl$, $KBr$, $KI$, $K_2C_2O_4$, $K_2SO_4$, $Cs_2CO_3$, $CsPO_4$, $CsOH$, $Cs_2O$, $CsCl$, $CsBr$, $CsI$, $CsC_2O_4$, $CsSO_4$, $Be(OH)_2$, $BeCO_3$, $BePO_4$, $BeO$, $BeCl_2$, $BeBr_2$, $BeI_2$, $BeC_2O_4$. $BeSO_4$, $Mg(OH)_2$, $MgCO_3$, $MgPO_4$, $MgO$, $MgCl_2$, $MgBr_2$, $MgI_2$, $MgC_2O_4$. $MgSO_4$, $Ca(OH)_2$, $CaO$, $CaCO_3$, $CaPO_4$, $CaCl_2$, $CaBr_2$, $CaI_2$, $Ca(OH)_2$, $CaC_2O_4$, $CaSO_4$, $Y_2O_3$, $Y_2(CO_3)_3$, $Y_2(PO_4)_3$, $Y(OH)_3$, $YCl_3$, $YBr_3$, $YI_3$, $Y_2(C_2O_4)_3$, $Y_2(SO_4)_3$, $Zr(OH)_4$, $Zr(CO_3)_2$, $Zr(PO_4)_2$, $ZrO(OH)_2$, $ZrO_2$, $ZrCl_4$, $ZrBr_4$, $ZrI_4$, $Zr(C_2O_4)_2$, $Zr(SO_4)_2$, $Ti(OH)_4$, $TiO(OH)_2$, $Ti(CO_3)_2$, $Ti(PO_4)_2$, $TiO_2$, $TiCl_4$, $TiBr_4$, $TiI_4$, $Ti(C_2O_4)_2$, $Ti(SO_4)_2$, $BaO$, $Ba(OH)_2$, $BaCO_3$, $BaPO_4$, $BaCl_2$, $BaBr_2$, $BaI_2$, $BaC_2O_4$, $BaSO_4$, $La(OH)_3$, $La_2(CO_3)_3$, $La_2(PO_4)_3$, $La_2O_3$, $LaCl_3$, $LaBr_3$, $LaI_3$, $La_2(C_2O_4)_3$, $La_2(SO_4)_3$, $Ce(OH)_4$, $Ce(CO_3)_2$, $Ce(PO_4)_2$, $CeO_2$, $Ce_2O_3$, $CeCl_4$, $CeBr_4$, $CeI_4$, $Ce(C_2O_4)_2$, $Ce(SO_4)_2$, $ThO_2$, $Th(CO_3)_2$, $Th(PO_4)_2$, $ThCl_4$, $ThBr_4$, $ThI_4$, $Th(OH)_4$, $Th(C_2O_4)_2$, $Th(SO_4)_2$, $Sr(OH)_2$, $SrCO_3$, $SrPO_4$, $SrO$, $SrCl_2$, $SrBr_2$, $SrI_2$, $SrC_2O_4$, $SrSO_4$, $Sm_2O_3$, $Sm_2(CO_3)_3$, $Sm_2(PO_4)_3$, $SmCl_3$, $SmBr_3$, $SmI_3$, $Sm(OH)_3$, $Sm_2(CO_3)_3$, $Sm_2(C_2O_3)_3$, $Sm_2(SO_4)_3$, $LiCa_2Bi_3O_4Cl_6$, $Na_2WO_4$, K/Sr-$CoO_3$, K/Na/$SrCoO_3$, Li/$SrCoO_3$, $SrCoO_3$, molybdenum oxides, molybdenum hydroxides, molybdenum carbonates, molybdenum phosphates, molybdenum chlorides, molybdenum bromides, molybdenum iodides, molybdenum oxalates, molybdenum sulfates, manganese oxides, manganese chlorides, manganese bromides, manganese iodides, manganese hydroxides, manganese oxalates, manganese sulfates, manganese tungstates, vanadium oxides, vanadium carbonates, vanadium phosphates, vanadium chlorides, vanadium bromides, vanadium iodides, vanadium hydroxides, vanadium oxalates, vanadium sulfates, tungsten oxides, tungsten carbonates, tungsten phosphates, tungsten chlorides, tungsten bromides, tungsten iodides, tungsten hydroxides, tungsten oxalates, tungsten sulfates, neodymium oxides, neodymium carbonates, neodymium phosphates, neodymium chlorides, neodymium bromides, neodymium iodides, neodymium hydroxides, neodymium oxalates, neodymium sulfates, europium oxides, europium carbonates, europium phosphates, europium chlorides, europium bromides, europium iodides, europium hydroxides, europium oxalates, europium sulfates rhenium oxides, rhenium carbonates, rhenium phosphates, rhenium chlorides, rhenium bromides, rhenium iodides, rhenium hydroxides, rhenium oxalates, rhenium sulfates, chromium oxides, chromium carbonates, chromium phosphates, chromium chlorides, chromium bromides, chromium iodides, chromium hydroxides, chromium oxalates, chromium sulfates, potassium molybdenum oxides and the like.

"Oxide" refers to a metal compound comprising oxygen. Examples of oxides include, but are not limited to, metal oxides ($M_xO_y$), metal oxyhalides ($M_xO_yX_z$), metal oxynitrates ($M_xO_y(NO_3)_z$), metal phosphates ($M_x(PO_4)_y$), metal oxycarbonates ($M_xO_y(CO_3)_z$), metal carbonates, metal oxyhydroxides ($M_xO_y(OH)_z$) and the like, wherein X is independently, at each occurrence, fluoro, chloro, bromo or iodo, and x, y and z are numbers from 1 to 100.

"Crystal domain" means a continuous region over which a substance is crystalline.

"Single-crystalline nanowires" means a nanowire having a single crystal domain.

"Turnover number" is a measure of the number of reactant molecules a catalyst can convert to product molecules per unit time.

"Active" or "catalytically active" refers to a catalyst which has substantial activity in the reaction of interest. For example, in some embodiments a catalyst which is OCM active (i.e., has activity in the OCM reaction) has a C2 selectivity of 5% or more and/or a methane conversion of 5% or more when the catalyst is employed as a heterogeneous catalyst in the oxidative coupling of methane at a temperature of 750° C. or less.

"Inactive" or "catalytically inactive" refers to a catalyst which does not have substantial activity in the reaction of interest. For example, in some embodiments a catalyst which is OCM inactive has a C2 selectivity of less than 5% and/or a methane conversion of less than 5% when the catalyst is employed as a heterogeneous catalyst in the oxidative coupling of methane at a temperature of 750° C. or less.

"Activation temperature" refers to the temperature at which a catalyst becomes catalytically active.

"Light off temperature" is the temperature at which a catalyst or catalytic material has sufficient catalytic activity to initiate the desired reaction. In certain embodiments, e.g., for exothermic reactions like OCM, the light off temperature is at a sufficient level to not only allow initiation of the catalyzed reaction, but to do so at a rate that is thermally self sufficient, e.g., generating enough thermal energy to maintain the reaction temperature at or above the initiation temperature.

"OCM activity" refers to the ability of a catalyst to catalyze the OCM reaction.

A catalyst having "high OCM activity" refers to a catalyst having a C2 selectivity of 50% or more and/or a methane conversion of 10% or more when the catalyst is employed as a heterogeneous catalyst in the oxidative coupling of methane at a specific temperature, for example 750° C. or less.

A catalyst having "moderate OCM activity" refers to a catalyst having a C2 selectivity of about 20-50% and/or a methane conversion of about 5-10% or more when the catalyst is employed as a heterogeneous catalyst in the oxidative coupling of methane at a temperature of 750° C. or less.

A catalyst having "low OCM activity" refers to a catalyst having a C2 selectivity of about 5-20% and/or a methane conversion of about 1-5% or more when the catalyst is employed as a heterogeneous catalyst in the oxidative coupling of methane at a temperature of 750° C. or less.

"Dopant" or "doping agent" is an impurity added to or incorporated within a catalyst to optimize catalytic performance (e.g. increase or decrease catalytic activity). As compared to the undoped catalyst, a doped catalyst may increase or decrease the selectivity, conversion, and/or yield of a reaction catalyzed by the catalyst.

"Atomic percent" (at % or at/at) or "atomic ratio" when used in the context of nanowire dopants refers to the ratio of the total number of dopant atoms to the total number of metal atoms in the nanowire. For example, the atomic percent of dopant in a lithium doped $Mg_6MnO_8$ nanowire is determined by calculating the total number of lithium atoms and dividing by the sum of the total number of magnesium and manganese atoms and multiplying by 100 (i.e., atomic percent of dopant=[Li atoms/(Mg atoms+Mn atoms)]×100).

"Weight percent" (wt/wt) "when used in the context of nanowire dopants refers to the ratio of the total weight of dopant to the total combined weight of the dopant and the nanowire. For example, the weight percent of dopant in a lithium doped $Mg_6MnO_8$ nanowire is determined by calculating the total weight of lithium and dividing by the sum of the total combined weight of lithium and $Mg_6MnO_8$ and multiplying by 100 (i.e., weight percent of dopant=[Li weight/(Li weight+$Mg_6MnO_8$ weight)]×100).

"Group 1" elements include lithium (Li), sodium (Na), potassium (K), rubidium (Rb), cesium (Cs), and francium (Fr).

"Group 2" elements include beryllium (Be), magnesium (Mg), calcium (Ca), strontium (Sr), barium (Ba), and radium (Ra).

"Group 3" elements include scandium (Sc) and yttrium (Y).

"Group 4" elements include titanium (Ti), zirconium (Zr), halfnium (Hf), and rutherfordium (Rf).

"Group 5" elements include vanadium (V), niobium (Nb), tantalum (Ta), and dubnium (Db).

"Group 6" elements include chromium (Cr), molybdenum (Mo), tungsten (W), and seaborgium (Sg).

"Group 7" elements include manganese (Mn), technetium (Tc), rhenium (Re), and bohrium (Bh).

"Group 8" elements include iron (Fe), ruthenium (Ru), osmium (Os), and hassium (Hs).

"Group 9" elements include cobalt (Co), rhodium (Rh), iridium (Ir), and meitnerium (Mt).

"Group 10" elements include nickel (Ni), palladium (Pd), platinum (Pt) and darmistadium (Ds).

"Group 11" elements include copper (Cu), silver (Ag), gold (Au), and roentgenium (Rg).

"Group 12" elements include zinc (Zn), cadmium (Cd), mercury (Hg), and copernicium (Cn).

"Lanthanides" include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), yitterbium (Yb), and lutetium (Lu).

"Actinides" include actinium (Ac), thorium (Th), protactinium (Pa), uranium (U), neptunium (Np), plutonium (Pu), americium (Am), curium (Cm), berklelium (Bk), californium (Cf), einsteinium (Es), fermium (Fm), mendelevium (Md), nobelium (No), and lawrencium (Lr).

"Metal element" or "metal" is any element, except hydrogen, selected from Groups 1 through 12, lanthanides, actinides, aluminum (Al), gallium (Ga), indium (In), tin (Sn), thallium (Tl), lead (Pb), and bismuth (Bi). Metal elements include metal elements in their elemental form as well as metal elements in an oxidized or reduced state, for example, when a metal element is combined with other elements in the form of compounds comprising metal elements. For example, metal elements can be in the form of hydrates, salts, oxides, as well as various polymorphs thereof, and the like.

"Semi-metal element" refers to an element selected from boron (B), silicon (Si), germanium (Ge), arsenic (As), antimony (Sb), tellurium (Te), and polonium (Po).

"Non-metal element" refers to an element selected from carbon (C), nitrogen (N), oxygen (O), fluorine (F), phosphorus (P), sulfur (S), chlorine (Cl), selenium (Se), bromine (Br), iodine (I), and astatine (At).

"C2" refers to a hydrocarbon (i.e., compound consisting of carbon and hydrogen atoms) having only two carbon atoms, for example ethane and ethylene. Similarly, "C3" refers to a hydrocarbon having only 3 carbon atoms, for example propane and propylene.

"Conversion" means the mole fraction (i.e., percent) of a reactant converted to a product or products.

"Selectivity" refers to the percent of converted reactant that went to a specified product, e.g., C2 selectivity is the % of converted methane that formed ethane and ethylene, C3 selectivity is the % of converted methane that formed propane and propylene, CO selectivity is the % of converted methane that formed CO.

"Yield" is a measure of (e.g. percent) of product obtained relative to the theoretical maximum product obtainable. Yield is calculated by dividing the amount of the obtained product in moles by the theoretical yield in moles. Percent yield is calculated by multiplying this value by 100. C2 yield is defined as the sum of the ethane and ethylene molar flow at the reactor outlet multiplied by two and divided by the inlet methane molar flow. C3 yield is defined as the sum of propane and propylene molar flow at the reactor outlet multiplied by three and divided by the inlet methane molar flow. C2+ yield is the sum of the C2 yield and C3 yield. Yield is also calculable by multiplying the methane conversion by the relevant selectivity, e.g., C2 yield is equal to the methane conversion times the C2 selectivity.

"Bulk catalyst" or "bulk material" means a catalyst prepared by traditional techniques, for example by milling or grinding large catalyst particles to obtain smaller/higher surface area catalyst particles. Bulk materials are prepared with minimal or no control over the size and/or morphology of the material.

"Alkane" means a straight chain or branched, noncyclic or cyclic, saturated aliphatic hydrocarbon. Alkanes include linear, branched and cyclic structures. Representative straight chain alkanes include methane, ethane, n-propane, n-butane, n-pentane, n-hexane, and the like; while branched alkanes include isopropane, secbutane, isobutane, tertbutane, isopentane, and the like. Representative cyclic alkanes include cyclopropane, cyclobutane, cyclopentane, cyclohexane, and the like. "Alkene" means a straight chain or branched, noncyclic or cyclic, unsaturated aliphatic hydrocarbon having at least one carbon-carbon double bond. Alkenes include linear, branched and cyclic structures. Representative straight chain and branched alkenes include ethylene, propylene, 1-butene, 2-butene, isobutylene, 1-pentene, 2-pentene, 3-methyl-1-butene, 2-methyl-2-butene, 2,3-dimethyl-2-butene, and the like. Cyclic alkenes include cyclohexene and cyclopentene and the like.

"Alkyne" means a straight chain or branched, noncyclic or cyclic, unsaturated aliphatic hydrocarbon having at least one carbon-carbon triple bond. Alkynes include linear, branched and cyclic structures. Representative straight chain and branched alkynes include acetylene, propyne, 1-butyne, 2-butyne, 1-pentyne, 2-pentyne, 3-methyl-1-butyne, and the like. Representative cyclic alkynes include cycloheptyne and the like.

"Alkyl," "alkenyl" and "alkynyl" refers to an alkane, alkene or alkyne radical, respectively.

"Aromatic" means a carbocyclic moiety having a cyclic system of conjugated p orbitals forming a delocalized conjugated $\pi$ system and a number of $\pi$ electrons equal to 4n+2 with n=0, 1, 2, 3, etc. Representative examples of aromatics include benzene and naphthalene and toluene. "Aryl" refers to an aromatic radical. Exemplary aryl groups include, but are not limited to, phenyl, napthyl and the like.

"Carbon-containing compounds" are compounds that comprise carbon. Non-limiting examples of carbon-containing compounds include hydrocarbons, CO and $CO_2$.

As used throughout the specification, a catalyst composition represented by $E^1/E^2/E^3$, etc., wherein $E^1$, $E^2$ and $E^3$ are each independently an element or a compound comprising one or more elements, refers to a catalyst composition comprised of a mixture of $E^1$, $E^2$ and $E^3$. $E^1/E^2/E^3$, etc. are not necessarily present in equal amounts and need not form a bond with one another. For example, a catalyst comprising Li/MgO refers to a catalyst comprising Li and MgO, for example, Li/MgO may refer to a MgO catalyst doped with Li. By way of another example, a catalyst comprising $NaMnO_4$/MgO refers to a catalyst comprised of a mixture of $NaMnO_4$ and MgO. Dopants may be added in suitable form. For example in a lithium doped magnesium oxide catalyst (Li/MgO), the Li dopant can be incorporated in the form of $Li_2O$, $Li_2CO_3$, LiOH, or other suitable forms. Li may be fully incorporated in the MgO crystal lattice (e.g., (Li,Mg)O) as well. Dopants for other catalyst may be incorporated analogously.

"Mixed oxide" or "mixed metal oxide" refers to a compound comprising two or more oxidized metals and oxygen (i.e., $M1_xM2_yO_z$, wherein M1 and M2 are the same or different metal elements, O is oxygen and x, y and z are numbers from 1 to 100). A mixed oxide may comprise metal elements in various oxidation states and may comprise more than one type of metal element. For example, a mixed oxide of manganese and magnesium comprises oxidized forms of magnesium and manganese. Each individual manganese and magnesium atom may or may not have the same oxidation state. Mixed oxides comprising 2, 3, 4, 5, 6 or more metal elements can be represented in an analogous manner. Mixed oxides also include oxy-hydroxides (e.g., $M_xO_yOH_z$, wherein M is a metal element, O is oxygen, x, y and z are numbers from 1 to 100 and OH is hydroxy). Mixed oxides may be represented herein as M1-M2, wherein M1 and M2 are each independently a metal element.

"$O_2$-OCM catalyst" refers to a catalyst having activity in the OCM reaction and which predominately uses $O_2$ as an oxygen source.

"$CO_2$-OCM catalyst" refers to a catalyst having activity in the OCM reaction and which predominately uses $CO_2$ as an oxygen source.

"$O_2$-ODH catalyst" refers to a catalyst having activity in the ODH reaction and which predominately uses $O_2$ as an oxygen source.

"$CO_2$-ODH catalyst" refers to a catalyst having activity in the ODH reaction and which predominately uses $CO_2$ as an oxygen source.

1. Catalysts

The catalytic materials described herein generally comprise one or more catalysts in combination with a support, binder and/or diluent material. In some embodiments, diluents are selected from bulk materials (e.g. commercial grade), nano materials (nanowires, nanorods, nanoparticles, etc.) and combinations thereof. Catalysts useful in the disclosed catalytic forms and formulations include any heterogeneous catalyst. The catalysts can have various elemental components and activity in a variety of reactions. In certain embodiments the catalyst is an OCM active catalyst. The exact elemental components or morphological form of the catalysts is not critical, provided they may be used in combination with the supports, diluents and/or binders described herein. In this regard, catalysts useful for practice of various embodiments of the invention include any bulk and/or nanostructured catalyst in any combination. For example, in some embodiments the catalyst comprises a catalyst as described in co-pending U.S. application Ser. No. 13/115,082 (U.S. Pub. No. 2012/0041246); Ser. No. 13/479,767 (U.S. Pub. No. 2013/0023709); Ser. No. 13/689,611; and Ser. No. 13/689,514, the full disclosures of which are hereby incorporated by reference in their entirety for all purposes. In certain embodiments, the catalyst is a nanowire catalyst, for example a nanowire comprising a metal oxide, metal hydroxide, metal oxyhydroxide, metal oxycarbonate, metal carbonate or combinations thereof. In some other related embodiments, the catalyst is an inorganic nanowire comprising one or more metal elements from any of Groups 1 through 7, lanthanides, actinides or combinations thereof and a dopant comprising a metal element, a semi-metal element, a non-metal element or combinations thereof.

In some other embodiments, the catalyst is an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof. Such a nanowire may optionally include one or more dopants.

In some other embodiments, the catalyst is an inorganic catalytic nanowire, the nanowire having a ratio of effective length to actual length of one and an aspect ratio of greater than ten as measured by TEM in bright field mode at 5 keV, wherein the nanowire may optionally include one or more dopants.

In other embodiments, the present invention is directed to catalyst forms and formulations comprising a catalytic nanowire which comprises at least four different doping elements, wherein the doping elements are selected from a metal element, a semi-metal element and a non-metal element. In other embodiments, the catalyst is a catalytic nanowire comprising at least two different doping elements, wherein the doping elements are selected from a metal element, a semi-metal element and a non-metal element, and wherein at least one of the doping elements is K, Sc, Ti, V, Nb, Ru, Os, Ir, Cd, In, Tl, S, Se, Po, Pr, Tb, Dy, Ho, Er, Tm, Lu or an element selected from any of groups 6, 7, 10, 11, 14, 15 or 17.

Other embodiments include catalytic forms and formulations wherein the catalyst comprises at least one of the following dopant combinations: Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Sr/Hf/K, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Sr/Zr, Li/Sm/Cs, Ba/Sm/Yb/S, Ba/Tm/K/La, Ba/Tm/Zn/K, Sr/Zr/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Sr/Ce, Na/Pt/Bi, Rb/Hf, Ca/Cs, Ca/Mg/Na, Hf/Bi, Sr/Sn, Sr/W, Sr/Nb, Sr/Ce/K, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Sr/Tb, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tb/K, Sr/Tm, La/Dy, Sm/Li/Sr, Mg/K, Sr/Pr, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Sr/Pr/K, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Sr/Hf/Rb, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Sr/B, Zn/Bi, Gd/Ho, Zr/Bi, Ho/Sr, Gd/Ho/Sr, Ca/Sr, Ca/Sr/W, Sr/Ho/Tm/Na, Na/Zr/Eu/Tm, Sr/Ho/Tm/Na, Sr/Pb, Sr/W/Li, Ca/Sr/W or Sr/Hf. In various embodiments of the foregoing, the catalyst is a catalytic nanowire, for example a catalytic nanowire comprising a rare earth oxide and one or more of the foregoing dopant combinations.

In other embodiments, the catalyst comprises a lanthanide mixed oxide compound. For example, in certain embodiments the catalyst is a catalytic nanowire comprising $Ln1_{4-x}Ln2_xO_6$ and a dopant comprising a metal element, a semi-metal element, a non-metal element or combinations thereof, wherein Ln1 and Ln2 are each independently a lanthanide element, wherein Ln1 and Ln2 are not the same and x is a number ranging from greater than 0 to less than 4. In other embodiments, the catalyst is a catalytic nanowire comprising a mixed oxide of Y—La, Zr—La, Pr—La, Ce—La or combinations thereof and at least one dopant selected from a metal element, a semi-metal element and a non-metal element.

In some other embodiments, the catalyst comprises a mixed oxide of a rare earth element and a Group 13 element, wherein the catalytic nanowire further comprises one or more Group 2 elements. In some more specific embodiments, the foregoing catalyst is a nanowire catalyst.

In another embodiment the catalyst comprises a lanthanide oxide doped with an alkali metal, an alkaline earth metal or combinations thereof, and at least one other dopant from groups 3-16. In some more specific embodiments, the foregoing catalyst is a nanowire catalyst.

In still other embodiments, the catalyst comprises a single pass methane conversion in an OCM reaction of greater than 20%, for example in some such embodiments the catalyst is a catalytic nanowire. In other embodiments the catalyst comprises a C2 selectivity of greater than 10% in the OCM reaction when the OCM reaction is performed with an oxygen source other than air or $O_2$. In certain embodiments of the foregoing, the catalyst is a catalytic nanowire.

In yet other embodiments, the catalyst comprises a mixed oxide of magnesium and manganese, wherein the catalyst further comprises lithium and boron dopants and at least one doping element from groups 4, 9, 12, 13 or combinations thereof. In other examples, the catalyst comprises an oxide of a rare earth element, wherein the catalyst further comprises at least one doping element from groups 1-16, lanthanides, actinides or combinations thereof. In still other examples, the catalyst comprises a mixed oxide of manganese and tungsten, wherein the catalyst further comprises a sodium dopant and at least one doping element from groups 2, 4-6, 8-15, lanthanides or combinations thereof. In yet other embodiments, the catalyst comprises a mixed oxide of a lanthanide and tungsten, wherein the catalyst further comprises a sodium dopant and at least one doping element from groups 2, 4-15, lanthanides or combinations thereof, wherein the catalyst comprises a $C_2$ selectivity of greater than 50% and a methane conversion of greater than 20% when the catalyst is employed as a heterogeneous catalyst in the oxidative coupling of methane at a temperature of 750° C. or less.

In other aspects, the catalytic forms and formulations comprise a catalyst comprising a mixed oxide of manganese and tungsten, wherein the catalyst further comprises a sodium dopant and at least one doping element from groups 2, 16 or combinations thereof.

In various embodiments, the catalysts employed in the catalytic materials herein have a C2 selectivity of greater than 50%, greater than 55%, greater than 60%, greater than 65%, greater than 70% or even greater than 75% when the catalyst is employed as a heterogeneous catalyst in the oxidative coupling of methane at a temperature of 750° C. or less, 700° C. or less, 650° C. or less or even 600° C. or less.

In other embodiments, the catalysts have a methane conversion in the OCM reaction of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less.

In various embodiments of the foregoing catalysts, the catalyst comprises a $C_2$ selectivity of greater than 50% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less.

In various embodiments of the foregoing catalysts, the catalyst comprises a $C_2$ selectivity of greater than 55% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less.

In various embodiments of the foregoing catalysts, the catalyst comprises a $C_2$ selectivity of greater than 60% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less.

In various embodiments of the foregoing catalysts, the catalyst comprises a $C_2$ selectivity of greater than 65% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less.

In various embodiments of the foregoing catalysts, the catalyst comprises a $C_2$ selectivity of greater than 70% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less.

In various embodiments of the foregoing catalysts, the catalyst comprises a $C_2$ selectivity of greater than 75% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less.

Other catalysts useful in the context of the catalytic forms and formulations described herein will be readily apparent to one of ordinary skill in the art.

2. Catalytic Formulations

As noted above, the present disclosure provides a catalytic material comprising a plurality of catalysts and optionally one or more binder, support, diluent and/or carrier materials. In some embodiments, the catalytic material comprises a plurality of bulk catalysts. In some embodiments, the catalytic material comprises a plurality of catalytic nanowires. In other embodiments, the catalytic materials comprise a plurality of inorganic catalytic polycrystalline nanowires, the plurality of nanowires having a ratio of average effective length to average actual length of less than one and an average aspect ratio of greater than ten as measured by TEM in bright field mode at 5 keV, wherein the plurality of nanowires comprises one or more elements from any of Groups 1 through 7, lanthanides, actinides or combinations thereof. In still other embodiments, the catalytic materials comprise a bulk catalyst. Mixtures of bulk and nanostructured catalysts (e.g., nanowires) are also contemplated.

Typically, heterogeneous catalysts are used either in their pure form or blended with inert materials, such as silica, alumina, etc. The blending with inert materials may be used in order to reduce and/or control large temperature non-uniformities within the reactor bed often observed in the case of strongly exothermic (or endothermic) reactions. In the case of complex multistep reactions, such as the reaction to convert methane into ethane and/or ethylene (OCM), typical blending materials can selectively slow down or quench one or more of the reactions of the system and promote unwanted side reactions. For example, in the case of the oxidative coupling of methane, silica and alumina can quench the methyl radicals and thus prevent the formation of ethane. Accordingly, certain embodiments are directed to catalytic materials comprising a catalyst (e.g., catalytic nanowire) and a blending material which enhances, rather than reduces, the catalytic activity of the catalyst.

In certain aspects, the present disclosure provides a catalytic material which solves problems typically associated with typical catalyst support material. Accordingly, in certain embodiments the catalytic activity of the catalytic material can be tuned by blending two or more catalysts and/or catalyst support materials. The blended catalytic material may comprise catalytic nanowires, bulk catalysts, or both and/or inert support material.

In certain embodiments, the catalytic material comprises a support, diluent and/or carrier. In some embodiments, the diluent is porous and has a high surface area. In some embodiments the support is active (i.e. has catalytic activity). In other embodiments, the diluent is inactive (i.e. non-catalytic). In some embodiments, the diluent comprises an inorganic material such as an inorganic oxide. In other embodiments the diluents comprises $Al_2O_3$, $SiO_2$, $TiO_2$, MgO, CaO, SrO, BaO, $ZrO_2$, ZnO, $LiAlO_2$, $MgAl_2O_4$, MnO, $MnO_2$, $Mn_3O_4$, $La_2O_3$, $AlPO_4$, $SiO_2/Al_2O_3$, $B_2O_3$, $Ga_2O_3$, $In_2O_3$, $SrAl_2O_4$, $B_4SrO_7$, $CaCO_3$, $SrCO_3$, activated carbon, silica gel, zeolites, activated clays, activated $Al_2O_3$, SiC, diatomaceous earth, aluminosilicates, calcium aluminate, barium aluminate, $CeO_2$, sulfates (e.g., $SrSO_4$, $BaSO_4$, etc.), support nanowires or combinations thereof. In still other embodiments, the diluent comprises a carbide (e.g., boron-carbide, silicon carbide and the like), a nitride, a carbonate (e.g., ammonium carbonate), a silicate or an aluminate.

In various embodiments of the above, the catalyst is a catalytic nanowire and the diluent comprises SrO, BaO, $B_2O_3$, $Ga_2O_3$, $In_2O_3$, $SrAl_2O_4$, $B_4SrO_7$, $CaCO_3$, $SrCO_3$, SiC, barium aluminate, $CeO_2$, sulfates (e.g., $SrSO_4$, $BaSO_4$, etc.), or combinations thereof.

In some more specific embodiments the diluent comprises silicon, for example $SiO_2$. In other embodiments the diluent comprises magnesium, for example MgO. In other embodiments the diluent comprises zirconium, for example $ZrO_2$. In yet other embodiments, the diluent comprises lanthanum, for example $La_2O_3$. In yet other embodiments, the diluent comprises yttrium, for example $Y_2O_3$. In yet other embodiments, the diluent comprises hafnium, for example $HfO_2$. In yet other embodiments, the diluent comprises aluminum, for example $Al_2O_3$. In yet other embodiments, the diluent comprises gallium, for example $Ga_2O_3$.

In still other embodiments, the diluent material comprises an inorganic oxide, $Al_2O_3$, $SiO_2$, $TiO_2$, MgO, $ZrO_2$, HfO2, CaO, SrO, ZnO, $LiAlO_2$, $MgAl_2O_4$, MnO, $MnO_2$, $Mn_2O_4$, $Mn_3O_4$, $La_2O_3$, activated carbon, silica gel, zeolites, activated clays, activated $Al_2O_3$, diatomaceous earth, aluminosilicates, calcium aluminate, barium aluminate, $CeO_2$, sulfates (e.g., $SrSO_4$, $BaSO_4$, etc.), diluent nanowires or combinations thereof. For example, the diluent material may comprise $SiO_2$, $ZrO_2$, CaO, $La_2O_3$ or MgO.

In still other embodiments, the diluent material comprises an SrO, ZnO, $LiAlO_2$, barium aluminate, $CeO_2$, sulfates (e.g., $SrSO_4$, $BaSO_4$, etc.) or combinations thereof.

In still other embodiments, the diluent material comprises a carbonate. For example, in some embodiments the diluent material comprises $MgCO_3$, $CaCO_3$, $SrCO_3$, $BaCO_3$, $Y_2(CO_3)_3$, $La_2(CO_3)_3$ or combination thereof.

When blending the catalyst with the diluent, the following exemplary procedure may be used: x (usually 10-50) mg of the catalyst (either bulk or test nanowire catalyst) is blended with (100-x) mg of diluent. Thereafter, about 2 ml of ethanol or water is added to form a slurry mixture, which is then sonicated for about 10 minutes. The slurry is then dried in an oven at about 100-140° C. for 2 hours to remove solvent. The resulting solid mixture is then scraped out and loaded into the reactor between the plugs of quartz wool.

In yet other embodiments of the catalytic materials, the catalytic materials comprise a nanowire and a different nanowire (catalytic or otherwise) may serve as a support for the catalytic nanowire. For example, a support nanowire may be non-catalytic, where a catalytic nanowire is adhered to or incorporated within the support nanowire. For example, in some embodiments, the support nanowires comprise $SiO_2$, MgO, CaO, SrO, $TiO_2$, $ZrO_2$, $Al_2O_3$, ZnO $MgCO_3$, $CaCO_3$, $SrCO_3$ or combinations thereof. Preparation of nanowire supported nanowire catalysts (e.g., core/shell nanowires) is discussed in more detail below.

The optimum amount of nanowire present on the support depends, inter alia, on the catalytic activity of the nanowire. In some embodiments, the amount of nanowire present on the support ranges from 0.1 to 100 parts by weight nanowires per 100 parts by weight of support. In some other embodiments, the amount of nanowire present on the support ranges from 1 to 100 parts by weight nanowires per 100 parts by weight of support or from 10 to 50 parts by weight nanowires per 100 parts by weight of support. In other embodiments, the amount of nanowire present on the support ranges from 100-200 parts by weight nanowires per 100 parts by weight of support, or 200-500 parts by weight of nanowires per 100 parts by weight of support, or 500-1000 parts by weight of nanowires per 100 parts by weight of support.

In some embodiments, the invention is directed to blended catalytic materials (i.e., containing two or more different catalysts) wherein the catalysts comprise metal oxides, hydroxides, oxy-hydroxides, carbonates, oxy-carbonates, or oxalates of the group 1-16 elements, lanthanides or actinides or combinations thereof. For example, the blended catalytic materials may comprise a plurality of inorganic catalytic polycrystalline nanowires, as described herein, and any one or more of straight nanowires, nanoparticles, bulk materials, inert support, diluent materials or binder materials. The catalytic materials may be undoped or may be doped with any of the dopants described herein.

Use of an inactive (or less active) diluent in order to minimize or otherwise adjust catalytic activity (for example in the OCM reaction) per unit volume of catalytic material may be desirable to avoid development of excessive hot spots (large temperature gradient through the catalyst bed resulting in local temperature in excess of the surrounding bed temperature). The overall selectivity of the reaction can be affected by localized high temperatures resulting in a portion of the catalyst operating outside of the range of desirable temperatures for high selectivity in the catalytic reaction of interest (e.g., OCM). Furthermore, localized hot spots can result in loss of catalyst activity through several mechanisms. For example loss of activity due to loss of catalyst surface area through sintering of the active material or loss of activity due to loss of dopant through vaporization or loss of activity due to active surface reconstruction or phase transition. Accordingly, it may be desirable to control, and particularly to reduce, minimize or avoid the formation of hot spots throughout the catalytic bed. Certain embodiments of the present invention provide catalytic materials which meet this goal by blending an active catalyst with an inactive (or less active) diluent. In this regard, any of the support or diluent materials described herein may be used.

In certain aspects, the diluent is selected to have little or no catalytic activity under the operating reaction conditions for the catalytic material. As will be appreciated, because catalytic activity is generally found at the surface of a catalyst material, in some embodiments, low surface area diluents of catalytic or non-catalytic material may be employed to ensure lower probability of reactive surface. For example, the diluent material may comprise a lower surface area structure than the active catalyst material. For example, a spherical diluent would have significantly lower surface area per unit weight than a high aspect ratio nanowire catalyst material or high surface area bulk catalyst. Accordingly, certain embodiments are directed to catalytic materials comprising an active catalyst and a diluent, wherein the diluent has a surface area per unit weight of at least 10% less than the active catalyst, at least 20% less than the active catalyst, at least 30% less than the active catalyst, at least 40% less than the active catalyst, or at least 50% less than the active catalyst.

In some examples, the catalytic materials serve to maintain a localized temperature within about 200° C. of the surrounding bed temperature, or within about 100° C. of the surrounding bed temperature or even within about 50° C. of the surrounding bed temperature. In this regard, the localized temperature is defined as the temperature within 1 mm, within 100 µm or within 10 µm radius of a certain point (X) within the catalyst bed, and the surrounding bed temperature refers to the average temperature over a radius (measured from point X) at least 50 times larger, 25 times larger or even 10 times larger than the radius of the localized temperature.

In certain embodiments, the catalytic materials comprise a first catalyst blended with a second catalyst, wherein the second catalyst has a higher temperature of activation in a catalytic reaction (e.g., OCM) than the first catalyst. For example, some catalytic materials of the present invention comprise a first catalyst and second catalyst, wherein the second catalyst has a temperature of activation in the OCM reaction of at least 200 degrees, at least 100 degrees, at least 50 degrees or at least 25 degrees higher than the temperature of activation in the OCM reaction than the first catalyst. In certain embodiments, both the first and second catalysts are nanowires. In other embodiments, both the first and second catalysts are bulk catalysts. In other embodiments, the first catalyst is a nanowire catalyst and the second catalyst is a bulk catalyst. In still other embodiments, the first catalyst is a bulk catalyst and the second catalyst is a nanowire catalyst.

The foregoing blended catalytic material embodiment is thought to provide certain advantages since large temperature gradients across the form or across the catalytic bed are generally obtained under the operating conditions of OCM, and the second catalyst may contribute to the conversion of methane to ethane and ethylene at higher temperatures. For example, in some embodiments an OCM catalyst (e.g., bulk catalyst) with high selectivity (e.g., >50% or >60% at >20% methane conversion) at elevated temperature (e.g., above 700° C., 750° C. or 800° C.) is blended with an OCM catalyst with high selectivity (e.g., >50% or >60% at >20% methane conversion) at low temperature (e.g., below 700° C., 650° C., 600° C., 550° C.) OCM catalyst (e.g., catalytic nanowires) to increase selectivity towards OCM when the local bed temperature gets high enough for the second catalyst to have significant OCM activity relative to the first catalyst. In this case non-uniform loading of the reactor or non-uniform distribution of the second (e.g., bulk) catalyst throughout the reactor may be desirable to enable the high temperature catalyst to compete with the very active OCM catalyst in some hotter areas of the reactor. For example, in some embodiments using different compositions throughout the reactor length with increasing second catalyst fraction toward the adiabatic reactor back end results in a more efficient OCM process. Further, blending a catalyst with lower surface area (e.g., a bulk catalyst) than the nanowire catalyst may be advantageous in providing increased OCM activity in the composite catalytic material.

In one embodiment, the invention is directed to a catalyst blend comprising at least one type 1 component and at least one type 2 component. In some embodiments, Type 1 components comprise catalysts having a high OCM activity at moderately low temperatures (e.g., 700° C. or lower) and type 2 components comprise catalysts having limited or no OCM activity at these moderately low temperatures, but have high selectivity in the OCM reaction at higher temperatures (e.g., above 700° C.). Such blended catalytic materials take advantage of the low light off temperature of the type 1 component while utilizing hotspots within the catalytic bed to increase the overall selectivity of the reaction due to the very high selectivity at high temperature of the type 2 component. Exemplary type 2 components in these embodiments include, but are not limited to, catalysts comprising LiMgMnB or Na/MnWO4. In some embodiments the type 2 catalyst is a bulk catalyst.

In certain other embodiments of the foregoing, the type 1 component comprises a catalyst having a high OCM activity at moderately low temperatures and the type 2 component comprise a catalyst having limited or no OCM activity at both low and high temperatures. In these embodiments, the type 2 component generally serves to control the temperature within the catalyst bed by decreasing the overall volumetric catalytic activity of the catalytic bed. An exemplary type 2 component in this regard is MgO.

For example, in some embodiments the type 1 component is a catalyst (e.g., nanowire) having high OCM activity at moderately low temperatures. For example, the type 1 component may comprise a C2 yield of greater than 5% or greater than 10% at temperatures less than 800° C., less than 700° C. or less than 600° C. The type 2 component may comprise a C2 yield less than 0.1%, less than 1% or less than 5% at temperatures less than 800° C., less than 700° C. or less than 600° C. The type 2 component may comprise a C2 yield of greater than 0.1%, greater than 1%, greater than 5% or greater than 10% at temperatures greater than 800° C., greater than 700° C. or greater than 600° C. Typical type 1 components include nanowires, for example polycrystalline nanowires as described herein, while typical type 2 components include bulk OCM catalysts and nanowire catalysts which only have good OCM activity at higher temperatures, for example greater than 800° C. The catalyst blend may further comprise inert support materials as described above (e.g., silica, alumina, silicon carbide, etc.).

In related embodiments of the foregoing, rather than mixing the type 1 and type 2 catalysts, each catalyst type is segregated into different locations within the catalyst bed. For example the catalyst bed may comprise two layers of catalysts, wherein one layer contains the type 1 catalyst and the other layer contains the type 2 catalyst. The type 1 catalyst may either be at the inlet end, or outlet end of the reactor. Other embodiments include various numbers of alternating layers (e.g., 1, 2, 3, 4, 5 or 6 or more layers) of type 1 catalysts and type 2 catalysts. Such stratified catalyst beds may serve to increase yield of desired C2 product while controlling the hot spots within the catalyst bed.

In certain embodiments, the type 2 component acts as diluent in the same way an inert material does and thus helps reduce and/or control hot spots in the catalyst bed caused by the exothermic nature of the OCM reaction. However, because the type 2 component is an OCM catalyst, albeit not a particularly active one, it may prevent the occurrence of undesired side reactions, e.g. methyl radical quenching. Additionally, controlling the hotspots has the beneficial effect of extending the lifetime of the catalyst.

For example, under certain conditions, it has been found that diluting active lanthanide oxide OCM catalysts (e.g., nanowires) with as much as a 10:1 ratio of MgO, which by itself is not an active OCM catalyst at the temperature which the lanthanide oxide operates, is a good way to minimize "hot spots" in the reactor catalyst bed, while maintaining the selectivity and yield performance of the catalyst. On the other hand, doing the same dilution with quartz $SiO_2$ was found not to be effective under certain reaction conditions, as it appears to quench the methyl radicals which serves to lower the selectivity to C2s.

In yet another embodiment, the type 2 components may be selected from good oxidative dehydrogenation (ODH) catalysts that demonstrate good catalytic activity (e.g., greater than 50% ethylene selectivity) at the same temperature where the type 1 components provide good OCM catalytic activity. In this embodiment, the ethylene/ethane ratio of the resulting gas mixture can be tuned in favor of higher ethylene. In another embodiment, the type 2 components may be selected from catalysts that are not only good ODH catalysts at the same temperature which the type 1 components are good OCM catalysts, but also such that they have limited to moderate OCM activity at these temperatures.

In related embodiments, the catalytic performance of the catalytic material is tuned by selecting specific type 1 and type 2 components of a catalyst blend. In another embodiment, the catalytic performance is tuned by adjusting the ratio of the type 1 and type 2 components in the catalytic material. For example, the type 1 catalyst may be a catalyst for a specific step in the catalytic reaction, while the type 2 catalyst may be specific for a different step in the catalytic reaction. For example, the type 1 catalyst may be optimized for formation of methyl radicals and the type 2 catalyst may be optimized for formation of ethane or ethylene.

In other embodiments, the catalyst material comprises at least two different components (component 1, component 2, component 3, etc.). The different components may comprise different morphologies, e.g., nanowires, nanoparticles, bulk, etc. The different components in the catalyst material can be, but not necessarily, of the same chemical composition and the only difference is in the morphology and/or the size of the particles. This difference in morphology and particle size may result in a difference in reactivity at a specific temperature. Additionally, the difference in morphology and particle size of the catalytic material components is advantageous for creating a very intimate blending, e.g., very dense packing of the catalysts particles, which can have a beneficial effect on catalyst performance. Also, the difference in morphology and particle size of the blend components would allow for control and tuning of the macro-pore distribution in the reactor bed and thus its catalytic efficiency. An additional level of micro-pore tuning can be attained by blending catalysts with different chemical composition and different morphology and/or particle size. The proximity effect would be advantageous for the reaction selectivity.

Accordingly, in one embodiment the present disclosure provides the use of a catalytic material comprising a first catalytic nanowire and a bulk catalyst and/or a second catalytic nanowire in a catalytic reaction, for example the catalytic reaction may be OCM or ODH. In other embodiments, the first catalytic nanowire and the bulk catalyst and/or second catalytic nanowire are each catalytic with respect to the same reaction, and in other examples the first catalytic nanowire and the bulk catalyst and/or second catalytic nanowire have the same chemical composition, but different morphologies.

In some specific embodiments of the foregoing, the catalytic material comprises a first catalytic nanowire and a second catalytic nanowire. Each nanowire can have completely different chemical compositions or they may have the same base composition and differ only by the doping elements. In other embodiments, each nanowire can have the same or a different morphology. For example, each nanowire can differ by the nanowire size (length and/or aspect ratio), by ratio of actual/effective length, by chemical composition or any combination thereof. Furthermore, the first and second nanowires may each be catalytic with respect to the same reaction but may have different activity. Alternatively, each nanowire may catalyze different reactions (e.g., OCM and ODH).

In a related embodiment, the catalytic material comprises a first catalytic nanowire and a bulk catalyst. The first nanowire and the bulk catalyst can have completely different chemical compositions or they may have the same base composition and differ only by the doping elements. Furthermore, the first nanowire and the bulk catalyst may each be catalytic with respect to the same reaction but may have different activity. Alternatively, the first nanowire and the bulk catalyst may catalyze different reactions.

In other related embodiments, the catalytic material comprises a nanowire containing composite in which the nanowire is the active OCM component and the diluent (e.g., any of the diluents described herein) is catalytically inert. Catalytically active nanowires and/or bulk catalysts can also be mixed with inactive nanowires. Since nanowires have been found to serve as good binding material in catalytic materials (see below), such embodiments serve to improve binding performance and mechanical strength of the composite at reduced active catalyst loading.

In yet other embodiments of the foregoing, the catalytic nanowire has a catalytic activity in the catalytic reaction, which is greater than a catalytic activity of the bulk catalyst in the catalytic reaction at the same temperature. In still other embodiments, the catalytic activity of the bulk catalyst in the catalytic reaction increases with increasing temperature.

OCM catalysts may be prone to hotspots due to the very exothermic nature of the OCM reaction. Diluting such catalysts helps to manage the hotspots. However, the diluent needs to be carefully chosen so that the overall performance of the catalyst is not degraded. Silicon carbide for example can be used as a diluent with little impact on the OCM selectivity of the blended catalytic material whereas using silica as a diluent can significantly reduce OCM selectivity. The good heat conductivity of SiC is also beneficial in minimizing hot spots. As noted above, use of a catalyst diluents or support material that is itself OCM active has significant advantages over more traditional diluents such as silica and alumina, which can quench methyl radicals and thus reduce the OCM performance of the catalyst. An OCM active diluent is not expected to have any adverse impact on the generation and lifetime of methyl radicals and thus the dilution should not have any adverse impact on the catalyst performance. Thus embodiments of the invention include catalyst compositions comprising an OCM catalyst (e.g., any of the disclosed nanowire catalysts) in combination with a diluent or support material that is also OCM active. Methods for use of the same in an OCM reaction are also provided.

In certain embodiments, the catalytic material comprises a plurality of catalytic nanowires in combination with a diluent, wherein the diluent comprises an alkaline earth metal compound, silicon carbide, cordierite, $B_2O_3$, $In_2O_3$, $SrAl_2O_4$, $B_4SrO_7$ or combinations thereof. In some embodiments, the above diluent comprises alkaline earth metal compounds, for example alkaline earth metal oxides, carbonates, sulfates, aluminates, silicates, aluminosilicates, or phosphates. In certain embodiments of the above, the alkaline earth metal compound is not MgO, CaO, $MgAl_2O_4$ or calcium aluminate.

Examples of diluents useful in various embodiments include, but are not limited to, $MgCO_3$, $MgSO_4$, $Mg_3(PO_4)_2$, $CaCO_3$, $CaSO_4$, $Ca_3(PO_4)_2$, SrO, $SrCO_3$, $SrSO_4$, $Sr_3(PO_4)_2$, $SrAl_2O_4$, BaO, $BaCO_3$, $BaSO_4$, $Ba_3(PO_4)_2$, $BaAl_2O_4$ and the like. Most of these compounds are very cheap, especially $MgCO_3$, $CaCO_3$, SrO, $SrCO_3$ and thus very attractive for use as diluents from an economic point of view. Additionally, the magnesium and calcium compounds are also environmentally friendly. Accordingly, an embodiment of the invention provides a catalytic material comprising a catalytic nanowire in combination with a diluent selected from one or more of $MgCO_3$, $MgSO_4$, $Mg_3(PO_4)_2$, $CaCO_3$, $CaSO_4$, $Ca_3(PO_4)_2$, SrO, $SrCO_3$, $SrSO_4$, $Sr_3(PO_4)_2$, BaO, $BaCO_3$, $BaSO_4$, $Ba_3(PO_4)_2$. In some specific embodiments the diluent is SrO, $MgCO_3$, $CaCO_3$, $SrCO_3$ or a combination thereof. In other embodiments, the catalytic material comprises a catalytic nanowire in combination with a diluent selected from one or more of MgO, CaO, $MgAl_2O_4$ and $CaAl_2O_4$, $MgCO_3$, $MgSO_4$, $Mg_3(PO_4)_2$, $CaCO_3$, $CaSO_4$, $Ca_3(PO_4)_2$, SrO, $SrCO_3$, $SrSO_4$, $Sr_3(PO_4)_2$, BaO, $BaCO_3$, $BaSO_4$, $Ba_3(PO_4)_2$. In some specific embodiments the diluent is SrO, $MgCO_3$, $CaCO_3$, $SrCO_3$ or a combination thereof. In some embodiments, the diluent is selected from magnesium aluminates and calcium aluminates. Methods for use of the foregoing catalytic materials in an OCM reaction are also provided. The methods comprise converting methane to ethane and or ethylene in the presence of the catalytic materials.

In some embodiments, the diluent is selected to have substantially no catalytic activity (i.e., non-catalytic) for the formation of side product; thus increasing the yield of desired product. For example, various embodiments include catalytic materials comprising an active catalyst and a diluent which has little or no catalytic activity in a reaction selected from the OCM reaction, carbon dioxide reforming reaction, combustion of hydrocarbons (e.g., C2 hydrocarbons) and any other reaction which would lead to side products and diminish the yield of desired product.

In some embodiments, the diluent's catalytic activity ranges from none to moderate at the temperature the OCM catalyst is operated. In some other embodiments, the diluent has moderate to high catalytic activity at a temperature higher than the temperature the OCM catalyst is operated. In yet some other embodiments, the diluent has none to moderate catalytic activity at the temperature the OCM catalyst is operated and moderate to high catalytic activity at temperatures higher than the temperature the OCM catalyst is operated. Typical temperatures for operating an OCM reaction according to the present disclosure are 800° C. or lower, 750° C. or lower, 700° C. or lower, 650° C. or lower, 600° C. or lower and 550° C. or lower. As used herein, the operation temperatures presented typically refer to the temperature immediately adjacent to the reactor inlet. As will be appreciated, with no integrated temperature control system, the exothermic nature of the OCM reaction can result in a temperature gradient across the reactor indicative of the progress of the reaction, where the inlet temperature can range from about 400° C. to about 600° C., while the outlet temperature ranges from about 700° C. to about 900° C. Typically, such temperature gradients can range from about 100° C. to about 500° C. By staging adiabatic reactors, with interstage cooling systems, one can step through a more complete catalytic reaction without generating extreme temperatures, e.g., in excess of 900° C.

For example, $CaCO_3$ is a relatively good OCM catalyst at T>750° C. (50% C2 selectivity, >20% methane conversion) but has essentially no activity below 700° C. Experiments performed in support of the present invention showed that dilution of $Nd_2O_3$ nanowires with $CaCO_3$ or $SrCO_3$ (bulk) showed no degradation of OCM performance and, in some cases, even better performance than the neat catalyst.

In some embodiments, the diluent portion in the catalyst/diluent mixture is 0.01%, 10%, 30%, 50%, 70%, 90% or 99.99% (weight percent) or any other value between 0.01% and 99.9%. In some embodiments, the dilution is performed with the OCM catalyst ready to go, e.g. after calcination. In some other embodiments, the dilution is performed prior to the final calcination of the catalyst, i.e. the catalyst and the diluent are calcined together. In yet some other embodiments, the dilution can be done during the synthesis as well, so that, for example, a mixed oxide is formed.

In certain embodiments, active catalyst to inert diluent ratio ranges from 5:95 to 95:5 (mass basis) in order to fulfill the desired performance criteria of managing localized temperature, catalyst activity and mechanical properties of the catalytic material. These criteria can vary within the catalyst packed bed as a function of location within the bed. For example for an adiabatic reactor with a large temperature rise through the reactor bed from inlet to outlet, a larger active catalyst to inert diluent ratio can be applied at the reactor inlet than the ratio used at the reactor outlet. If the selected requirement is keeping the local temperature under 900° C. for example, when the inlet gas temperature is 500° C. the allowed temperature differential within the pellet is 400° C. whereas at the outlet the product stream being at for example 750° C. the allowed temperature differential would only be 150° C.

In some embodiments, the ratio of active catalyst to diluent ranges from about 1:99 to 99:1 (mass basis), for example from about 5:95 to 95:5, from about 10:90 to about 90:10, from about 25:75 to about 75:25 or is about 50:50. The ratio of active catalyst to diluent will vary depending on the particular catalytic reaction, reaction conditions, upon mechanical strength needs, thermal control needs, catalyst activity, and other factors as described elsewhere herein. One of ordinary skill in the art will recognize how to determine the appropriate ratio.

Further dilution of the active catalyst loading can then easily be obtained by blending forms with no catalyst with forms containing active catalyst. The forms containing no active catalyst can be bonded at much higher temperature than the forms with active catalyst and can be typically made much more mechanically stronger than the active composite forms.

In some embodiments, the catalyst/diluent mixture comprises more than one catalyst and/or more than one diluent. In some other embodiments, the catalyst/diluent mixture is pelletized and sized, or made into shaped extrudates or deposited on a monolith or foam, or is used as it is. Such catalytic forms are described in more detail below. Methods of the invention include taking advantage of the very exothermic nature of OCM by diluting the catalyst with another catalyst that is completely or substantially inactive, or less active in the OCM reaction at the operating temperature of the first catalyst but active at higher temperature. In these methods, the heat generated by the hotspots of the first catalyst will provide the necessary heat for the second catalyst to become active.

In certain embodiments, the carrier or diluents are carefully selected to avoid negative interactions between the dopant and the carrier or diluents. For example, at high temperature when the doping element may have some mobility on the support, the dopant can migrate from the catalyst to the diluents or carrier when the diluent can form a stable doped material. For example, in some embodiments, Li doped catalysts have the potential to negatively interact with Silica or the silica layer on top of SiC above 800° C. since silica has a high affinity for the lithium ion. Accordingly, one embodiment includes a catalytic material comprising a lithium-doped catalyst and a non-silica based carrier or diluent.

In other examples, the diluent can be used as a dopant source to replenish dopant lost by vaporization or slow segregation (e.g., $BaSO_4$ used to stabilize gamma alumina by slowing leaching Ba into the $Al_2O_3$ framework as the sulfate decomposes over time). Accordingly, some embodiments are directed to a catalytic material comprising a doped catalyst and a diluent, wherein the diluent comprises a dopant or dopant source. In further embodiments, the doped catalyst and the diluent comprise the same dopant. In other embodiments, the diluent\ provides a dopant that is different than the dopant in the doped catalyst. In still other embodiments, the catalyst is substantially devoid of dopant and the diluents comprises a dopant that improves the catalytic performance of the catalyst.

In any of the above embodiments, the catalysts may comprise a $SiO_2$ support. Alternatively, the use of different supports such as $ZrO_2$, $HfO_2$ and $In_2O_3$ in any of the above embodiments has been shown to promote OCM activity at reduced temperature compared to the same catalyst supported on silica with limited reduction in selectivity.

A. Nanowire Formulations

Certain embodiments of the disclosed catalytic materials are directed to catalytic materials comprising nanowires as the catalytic component. The nanowires may have any elemental composition or morphological form (e.g., bent or straight, etc.). Catalytic materials comprising nanowires have certain benefits compared to non-nanostructured catalytic materials. For example, the present inventors have discovered that the intrinsic properties of nanowires allows for preparation of catalytic forms comprising nanowires without the need for traditional binders. Accordingly, one embodiment of the present invention is a catalytic material comprising a plurality of catalytic nanowires and substantially no binder. Such catalytic materials may have any of the extrudate shapes discussed below or known in the art. Additionally, such catalysts are advantageous for preparation of pressed pellets comprising nanowire catalysts.

While not wishing to be bound by theory, the binding ability of nanowires is thought to be due to the large aspect ratio of the nanowires providing an easily accessible and large surface area per unit volume of solid. A nanowire mesh presents very good cohesion since there is a large number of contact points between separate solid particles. This nanowire mesh is able to encapsulate any foreign component, such as the diluents described herein, and hold it within the nanowire mesh provided that the nanowire fraction is large enough (preferably around 10% per volume excluding void fraction—40% of volume including inter-nanowire void fraction).

If effective binding of the nanowires to the other composite components is obtained (material compatibility—diluent selection criteria), then the morphology of the nanowire mesh is advantageous again by providing a large number of contact points between the binder and the foreign composite component. The large number of contact point translates into better binding and mechanical strength. The composite mechanical strength is also improved toward thermal shock resistance because of a low level of plasticity afforded by the nanowire mesh and the difficulty in creating and propagating cracks through the nanowire mesh (as in bullet proof vests composites or acicular mullite high temperature ceramics).

The intrinsic binding properties of nanowires also makes them desirable binding material (i.e., non-active material) for binding other types of catalysts (i.e., non-nanowire catalysts). For example, certain embodiments of the present disclosure are directed to a catalytic material comprising an active catalyst and a nanowire binder. Non-limiting examples of this type of catalytic material include a catalytic material comprising zeolites as the active component and a nanowire binder.

Use of nanowires as binder in catalytic materials provides certain advantages over traditional inorganic binders. For example, in some embodiments of extruded catalytic materials, the large thixotropic properties of wet composites containing a nanowire gel improve the ability to extrude the catalytic materials and make various extrudate shapes.

Another advantage of using nanowires as binding material in a catalytic material is their pore forming ability. Because of the low solid fraction within the nanowire mesh filling the space between larger secondary composite components and the interconnected nature of these voids, the space filled by the binder is also a space providing easy diffusion of species throughout the form (e.g., a molecular highway with large interconnected pores). Similar large pore networks are typically obtained by using sacrificial forming agents which are removed after or during catalyst form calcination, however these strategies are at the expense of mechanical strength and may not result in very homogeneously distributed system of pores.

This property of providing easy transport of reactant and products molecules through the catalyst forms becomes very important in the case of mass transport limited reactions (in liquids with large molecules or in gas at high space velocities) and can enable use of larger forms when using nanowire binder in contrast to traditional binders. In the case of OCM catalysis at temperature 100 or 200° C. above light off temperature (defined as temperature at which significant activity is measured) the heterogeneous OCM reaction rates become transport limited, therefore this property is important for OCM in the case of adiabatic type reactor with large temperature gradient between bed inlet and outlet.

3. Catalytic Forms

The catalytic materials may also be employed in any number of forms. In this regard, the physical form of the catalytic materials may contribute to their performance in various catalytic reactions. In particular, the performance of a number of operating parameters for a catalytic reactor that impact its performance are significantly impacted by the form in which the catalyst is disposed within the reactor. As noted elsewhere herein, the catalyst may be provided in the form of discrete particles, e.g., pellets, extrudates or other formed aggregate particles, or it may be provided in one or more monolithic forms, e.g., blocks, honeycombs, foils, lattices, etc. These operating parameters include, for example, thermal transfer, flow rate and pressure drop through a reactor bed, catalyst accessibility, catalyst lifetime, aggregate strength, performance, and manageability.

In a certain embodiment, the form of the catalyst can directly impact the flow rate and pressure drop through a catalyst bed. In particular, the pressure drop across a catalyst bed, which can be estimated using the Ergun equation, is a function of the bed void volume, where increased void spaces, e.g., between catalyst particles, provides easier flow through the catalyst bed, and thus a smaller pressure drop across the catalyst bed. Pressure drop across the bed is also a function of size of the formed catalyst particles as defined by the effective particle diameter: $D_{p,eq}=6V_p/S_p$, where $V_p$ is the volume of formed catalyst and $S_p$ is the surface area of the catalyst. As the effective particle diameter increases the pressure drop decreases. With reference to previously described OCM reactions, the issue of pressure drop was of little importance since such reactions were carried out at relatively high pressures and small scales. In accordance with preferred low pressure OCM reactions described herein, however, it is desirable to maintain an entire reactor system at pressures and other operating conditions, that are more conventionally found in gas and other chemical processing systems. As such, it is desirable to provide rector systems that operate at inlet pressures of from about 15 psig to about 100 psig with relatively controlled pressure drops across the reactor bed. Thus, in accordance with certain embodiments, catalyst forms are selected to provide the reactors that have inlet pressures of between about 15 and 100 psig, with pressure drops that average between about 0.1 psig/linear foot of reactor bed depth to about 10 psig/linear foot of reactor bed depth. A variety of catalyst forms may be used to achieve these parameters as described herein. In particular, catalyst forms that provide void fractions within the reactor of from about 35% to about 70%, and preferably between about 45% and about 65%, will generally provide void fractions in an advantageous range. Notwithstanding the foregoing, a range of effective void fractions may be selected by selecting the appropriate particle size, to meet the desired pressure drop while still providing the requisite catalytic activity. In general, the catalyst particles will typically range from about 1 mm to about 20 mm in at least one cross sectional dimension, with preferred particle sizes for formed aggregates ranging from about 2 mm to about 10 mm in at least one cross sectional dimension. For example, in some embodiments the catalyst particles will typically be between about 1 mm and about 20 mm in at least one cross sectional dimension, with preferred particle sizes for formed aggregates being between about 2 mm and about 10 mm in at least one cross sectional dimension.

In accordance with certain embodiments, the foregoing parameters are adjusted in the context of maintaining other parameters in desired ranges. In particular, adjustment of void fraction and pressure drop is generally carried out in a manner that does not significantly adversely affect catalytic activity, or catalyst lifetime. In particular, preferred catalyst forms will provide desired pressure drops, while also providing desired performance activity. In general, catalyst forms that provide higher surface to volume ratios, while maintaining desired void fractions are preferred. Surface to volume ratios increase as the effective particle diameter decreases. Therefore, it is desirable to have as small an effective diameter as possible while still meeting the pressure drop requirements. Forms with smaller effective diameters can be used but the void fraction must increase to meet pressure drop requirements. In particular, catalyst forms that accomplish this include, e.g., rings, tubes, trilobes, trilobe rings, wagon wheels, monoliths, quadralobes, quadralobe rings and the like. In general, the surface area to volume ratio for the formed aggregate catalyst particles of the invention will range from about 0.1 $mm^{-1}$ to 10 $mm^{-1}$, and preferably from about 0.1 $mm^{-1}$ to about 5 $mm^{-1}$. In other embodiments, the surface area to volume ratio for the formed aggregate catalyst particles of the invention is between about 0.1 $mm^{-1}$ and 10 $mm^{-1}$, and preferably between about 0.1 $mm^{-1}$ and about 5 $mm^{-1}$.

In a further aspect, it is also desirable that the catalyst forms used will have crush strengths that meet the operating parameters of the reactor systems. In particular, a catalyst particle crush strength should generally support both the pressure applied to that particle from the operating conditions, e.g., gas inlet pressure, as well as the weight of the catalyst bed. In general, it is desirable that a catalyst particle have a crush strength that is greater than about 1 $N/mm^2$, and preferably greater than about 10 $N/mm^2$, for example greater than 1 $N/mm^2$, and preferably greater than 10 $N/mm^2$. As will be appreciated, crush strength may generally be increased through the use of catalyst forms that are more compact, e.g., having lower surface to volume ratios. However, adopting such forms may adversely impact performance. Accordingly, forms are chosen that provide the above described crush strengths within the desired activity ranges, pressure drops, etc. Crush strength is also impacted though use of binder and preparation methods (e.g., extrusion or pelleting).

In addition, in particularly preferred embodiments, the use of catalytic nanowire materials can enhance crush strength, as they can operate as binders themselves, and thus impart greater structural integrity and crush strength to the catalyst particle.

Another catalyst form characteristic that can impact overall reactor performance is the accessibility of the catalyst material within a catalyst particle. This is generally a function of the surface to volume ratio of the catalytic portion of a given catalyst particle. For a homogeneously dispersed catalyst, this relates to the surface:volume ratio of the entire particle, while for catalyst coated particles or forms, this would relate to the surface:volume ratio of the coating porosity of the catalyst particle. While this ratio is a function of the catalyst particle shape, e.g., spherical particles will have lower surface:volume ratios than other shapes, it can also be substantially impacted by the porosity of the catalyst particle. In particular, highly porous catalyst particles have larger effective diffusivities allowing for greater utilization of the formed catalyst in the reactor. Again, while highly porous catalyst particles may provide greater accessibility, they should generally do so while maintaining desired crush strengths, etc., which can be adversely impacted by increasing porosity. In particularly preferred aspects, catalyst particles or other forms will include a porosity of between about 10% and about 80% while maintaining the desired crush strengths above. In more preferred aspects, the porosity will be between about 40% and about 60%.

For example, in some embodiments the catalytic materials are in the form of an extrudate or pellet. Extrudates may be prepared by passing a semi-solid composition comprising the catalytic materials through an appropriate orifice or using molding or other appropriate techniques. Other catalytic forms include catalysts supported or impregnated on a support material or structure. In general, any support material or structure may be used to support the active catalyst. The support material or structure may be inert or have catalytic activity in the reaction of interest (e.g., OCM). For example, catalysts may be supported or impregnated on a monolith support. In some particular embodiments, the active catalyst is actually supported on the walls of the reactor itself, which may serve to minimize oxygen concentration at the inner wall or to promote heat exchange by generating heat of reaction at the reactor wall exclusively (e.g., an annular reactor in this case and higher space velocities). Exemplary catalytic forms useful in the practice of the present invention are described in more detail below.

The surface area to volume ratio of the catalytic form is an important parameter in determining the maximal flux of reagents and product molecules entering or leaving the catalytic form. This parameter also affects the temperature gradient throughout the form since increase in relative surface area tends to favor heat removal and minimize thickness of the form, hence limiting peak temperatures at the core of the particle. In the particular case of OCM active catalytic forms, the catalytic form envelope surface area to catalytic form envelope volume ratio ranges from about 0.5 to about 4 $mm^{-1}$ when the space velocities range from about 10,000 to about 200,000 h-1. At ratios larger than 4 $mm^{-1}$, the same catalytic forms may become mechanically weak, and in this case a coated substrate might be preferable. At ratios lower than 0.5 only a fraction of the catalyst is accessible to the reagent as the form gets too thick and transport limitations can become a limiting factor.

In some cases, it will be particularly desirable to provide a catalytic materials in which the active catalyst material is substantially homogeneously dispersed. As used herein, homogeneously dispersed means that across a given catalyst particle, the concentration of active catalyst does not vary by more than 25%, preferably not greater than 10%. For particularly preferred materials, this is advantageously achieved through the use of catalytic nanowire materials, which provide a more uniform dispersion profile within catalyst formulations, e.g., including diluents, binders etc.

For catalysts which are heterogeneously dispersed within the catalytic form (e.g., catalysts disposed on the surface of a support), the above mentioned ratio can become quite small (e.g., from about 0.1 to about 0.5) as effective catalyst used can be maintained by preferentially concentrating the active catalyst component at the surface of the form (e.g., adhered to surface of a support).

In certain preferred embodiments, the catalytic materials will satisfy one, two, three, four, five or more of the foregoing parameters. For example, the catalyst particles (or catalytic materials made therefrom, e.g., formed aggregate) may include one or more of a particle size that yields a bed void volume fraction of 35% to 70%, a crush strength of greater than 1 N/mm$^2$, a porosity ranging from 10% to 80% and a surface area to volume ratio ranging from 0.1 mm$^{-1}$ to 10 mm$^{-1}$. In other embodiments, the catalyst particles (or catalytic materials made therefrom, e.g., formed aggregate) may include one or more of a particle size that yields a bed void volume fraction of 45% to 65%, a crush strength of greater than 10 N/mm$^2$, a porosity ranging from 40% to 60% and a surface area to volume ratio ranging from 0.1 mm$^{-1}$ to 5 mm$^{-1}$.

In still more embodiments, the catalyst particles (or catalytic materials made therefrom, e.g., formed aggregate) may include one or more of a particle size that yields a bed void volume fraction of 40% to 60%, a crush strength of greater than 1 N/mm$^2$, a porosity ranging from 10% to 80% and a surface area to volume ratio ranging from 0.1 mm$^{-1}$ to 10 mm$^{-1}$. In some embodiments, the catalyst particles (or catalytic materials made therefrom, e.g., formed aggregate) may include one or more of a particle size that yields a bed void volume fraction of 35% to 70%, a crush strength of greater than 10 N/mm$^2$, a porosity ranging from 10% to 80% and a surface area to volume ratio ranging from 0.1 mm$^{-1}$ to 10 mm$^{-1}$. In other embodiments, the catalyst particles (or catalytic materials made therefrom, e.g., formed aggregate) may include one or more of a particle size that yields a bed void volume fraction of 35% to 70%, a crush strength of greater than 1 N/mm$^2$, a porosity ranging from 40% to 60% and a surface area to volume ratio ranging from 0.1 mm$^{-1}$ to 10 mm$^{-1}$. In still other embodiments, the catalyst particles (or catalytic materials made therefrom, e.g., formed aggregate) may include one or more of a particle size that yields a bed void volume fraction of 35% to 70%, a crush strength of greater than 1 N/mm$^2$, a porosity ranging from 10% to 80% and a surface area to volume ratio ranging from 0.1 mm$^{-1}$ to 5 mm$^{-1}$.

In some of the foregoing embodiments, wherein the catalytic materials satisfy one, two, three, four, five or more of the foregoing parameters, the catalyst particles (or catalytic materials made therefrom, e.g., formed aggregate) additionally comprise a particle size ranging from 1 mm to 20 mm. In other embodiments, the particle size ranges from 2 mm to 10 mm. Any of the foregoing catalytic materials may also comprise a surface area ranging from about 1 m$^2$/g to about 50 m$^2$/g.

The total surface area (including pores) by weight of the catalytic form is primarily determined by the composition (i.e., catalyst, binder, diluent, etc.) of the form. When low surface area diluent is used then most of the surface area of the solid comes from the OCM active catalyst. In certain embodiments, the surface area of the catalytic materials ranges from about 1 m$^2$/g to about 50 m$^2$/g depending on catalyst dilution when using low surface area diluent material.

One of the advantages of catalytic materials employing nanowire structured catalysts is that they can form aggregates with large pore volume presenting interconnected large pores. Typically pore volume fraction in catalytic materials containing a nanowire catalyst ranges from 20 to 90% (vol/vol) and can be modified by adjusting the ratio of diluent (typically lower porosity and lower surface area) to nanowire aggregates. When the pore structure is mostly dominated by the nanowire aggregates pores above 100 nm are the main source of pore volume within the composite form. Some embodiments include catalytic forms which have highly interconnected and large openings relative to reagent and product molecules, thus promoting diffusion through the form. This property can also be used when reactant flow is forced through the composite as for example in wall through flow monoliths for diesel soot removal.

In some examples, the catalytic forms are chosen in order to mitigate potential hot spots resulting from highly exothermic reactions. For example, in some embodiments the heat conductivity of the form is increased including material with high heat conductivity in the form. Examples of materials used to increase the heat conductivity include, but are not limited to, SiC. In other embodiments, the rate of heat generation per unit volume of form can be decreased, for example by dilution of the form with an inactive material, thus adjusting the catalyst surface area per form volume. At the same time the selection of the diluent to promote heat transfer through the form can be beneficial in reducing temperature gradient through the form. In this regard, any of the diluents described herein can be employed in the catalytic form for the purpose of promoting heat transfer and reducing the temperature gradient through the form.

In another embodiment, the thermal transfer properties of the catalytic form are controlled by heterogeneous loading of active catalyst throughout the form. For example, in some embodiments OCM catalyst can be coated upon a catalytically inert support resulting in an overall low catalyst loading per form and limited temperature gradient through the form (since there is no heat generation in the core of the particle). Again, the thickness of such coating layers will depend upon the desired ratio of catalyst to inert support and/or catalyst loading. In other embodiments, it may be desirable to increase the temperature gradient through the form in some locations of the pack-bed reactor. In this case active catalyst may be preferentially loaded in the core of the form with an outer shell containing low active catalyst amounts. Such strategies are discussed in more detail below.

In some embodiments a support (e.g., MgO, CaO, B$_2$O$_3$, Ga$_2$O$_3$, A$_{l2}$O$_3$, In$_2$O$_3$, SrAl$_2$O$_4$, B$_4$SrO$_7$, CaCO$_3$, SrCO$_3$, inorganic oxides, SiO$_2$, TiO$_2$, SrO, BaO, ZrO$_2$, ZnO, LiAlO$_2$, MgAl$_2$O$_4$, MnO, MnO$_2$, Mn$_3$O$_4$., La$_2$O$_3$, AlPO$_4$, SiO$_2$/Al$_2$O$_3$, activated carbon, silica gel, zeolites, activated clays, activated Al$_2$O$_3$, SiC, diatomaceous earth, magnesia, aluminosilicates, calcium aluminate, support nanowires or combinations thereof) may be used in the form of a pellet or extrudate or monolith (e.g., honeycomb) structure, and the catalysts may be impregnated or supported thereon. In other embodiments, a core/shell arrangement is provided and the support material may form part of the core or shell. For example, a core of MgO, CaO, $CaCO_3$ or $SrCO_3$ may be coated with a shell of catalyst.

In certain embodiments, the catalyst materials are provided as a formed aggregate that comprises the underlying catalyst material, and in many cases, one or more additional materials, including dopants, diluents, binders, supports, or other different catalyst materials, as described elsewhere herein. These formed aggregates may be prepared by a large number of different forming processes, including for example, extrusion processes, casting processes, press forming processes, e.g., tablet processes, free form aggregation processes (e.g., spray aggregation), immersion, spray, pan or other coating or impregnation processes. These formed aggregates may range in size from small particles, e.g., less than 1 mm in cross sectional dimension, to moderate size particles ranging from 1 mm to 2 cm in cross sectional dimension, e.g., for typical pellet or extrudate sized particles, to much larger forms, ranging from 2 cm to 1 or more meters in cross sectional dimension, e.g., for larger formed aggregates and monolithic forms.

In some embodiments, diluents or binders used for the purpose of forming composite formed aggregates containing a heterogeneous catalyst (e.g., an OCM active catalyst) are selected from Silicon Carbide, Magnesium Oxide, Calcium Oxide, Alumina, aluminosilicates, carbonates, sulfates, low acidity refractory oxides such as cordierite ($Mg_2Al_4Si_5O_{18}$) and calcium aluminates (e.g., CaAl2O4, $Ca_3Al_2O_6$). The diluents are preferentially of low surface area and low porosity in order to minimize potential negative interaction between the diluent surface and the reaction product intermediates.

Additional binders can also be used in order to improve the mechanical strength (in particular crush strength) of the formed aggregates. In some embodiments, such binders are inorganic precursors or inorganic clusters capable of forming bridges between the particles in the aggregate, for example, colloidal silica, alumina or zirconia may be used. In the particular case of an OCM catalyst however, inertness of the binder toward reaction intermediates is generally desired. Since standard colloidal silica and standard colloidal Zirconia have been found to interfere with the OCM reaction, certain embodiments include catalytic materials which do not comprise these types of binders, and in certain embodiments the catalytic materials comprise a catalytic nanowire and substantially no binder (i.e., the nanowires act as binder material). In some embodiments, the binder may comprise low concentration of $CeO_2$ provided the red-ox activity of the binder is much smaller than the overall catalyst activity for OCM of the composite form.

Apart from the above mentioned components, further components and auxiliaries are typically added to the mixture to be formed (e.g., extruded). Water and, if appropriate, acids or bases may be employed. In addition, organic and inorganic substances which contribute to improved processing during formation of the catalytic form and/or to a further increase in the mechanical strength and/or the desired porosity of the extruded catalytic material can additionally be employed as auxiliaries. Such auxiliaries are known to those skilled in the art, and examples include graphite, stearic acid, methylstearate, silica gel, siloxanes, cellulose compounds, starch, polyolefins, carbohydrates (sugars), waxes, alginates, and polyethylene glycols (PEGs).

The ratios of active catalyst to binder to be used in the formed aggregate varies depending upon the desired final catalyst form, the desired catalytic activity and/or mechanical strength of the catalytic form and the identity of the catalyst. With regard to extrudates, the rheology of the paste to extrude can be varied to obtain the desired catalytic material. One of ordinary skill in the art will be able to arrive at the appropriate catalyst to binder ratio.

In some embodiments, the catalytic materials of the invention can be produced in various shapes. In this regard, extrudates find particular utility. Examples which may be mentioned include cylindrical extrudates, rods, star or ribbed extrudates, trilobes, hollow extrudates, donut or ring-shaped extrudates, pellets, tubed, spherical, honeycombs and irregular shapes. The typical diameters of these extrudates are from 0.5 to 20 mm, preferably from 1 to 6 mm, particularly preferably from 1.5 to 3 mm. The mean ratio of length to diameter is from 0.2:1 to 20:1, preferably from 0.7:1 to 10:1, particularly preferably from 1:1 to 5:1.

The shape of the catalytic materials may be selected to either increase or decrease the active catalyst volumetric loading since the shape of the form may have a significant impact on the void fraction between formed particles. For example, one embodiment is directed to donut shaped particles which have larger inter packbed void fraction because of the added void contributed by the donut hole in this form when compared to a plain cylindrical shape of the same diameter.

Other aspects are directed to hollow catalytic forms (which are typically prepared by extrusion or casting, but may be press formed as well). Such embodiments allow separation of different gas domains by a porous and catalytically active material. One implementation of such design is in hollow tubes with walls made of nanowire catalyst with diluent material. The tubes may be used to introduce reagents in separate streams. Another implementation of such complex form can be wall flow through monoliths where feed gases and product gases are on separate sides of the catalytic walls.

In certain preferred aspects, tube or ring shaped catalyst particles are used. In such cases, it has been found that the wall or ring thickness can have a significant impact on performance. In particular, a larger wall or ring thickness can promote lower light-off temperatures for OCM reactions. Restated, ring or tube shaped catalyst forms or particles having a higher ratio of the outer diameter to the inner diameter show lower light-off temperatures for OCM reactions. In particularly preferred aspects, the wall or ring thickness of an OCM catalyst particle, e.g., a nanowire OCM catalyst containing particle as described elsewhere herein, is selected so that the ratio of inner diameter to outer diameter is between about 0.3 and 0.7. For example, in some cases, the wall thickness of the catalyst particle may be between about 1 mm and about 3 mm, with particularly preferred catalyst particles being between about 2 mm and about 1.2 mm, and more preferably between about 2 mm and about 1.4 mm, with even more preferred wall thicknesses being between about 1.5 and 1.9 mm for catalyst rings or tubes that have an overall diameter of between about 1 mm and about 25 mm, preferably between about 1 mm and about 5 mm.

In some embodiments, the catalytic material is in the form of a straight long shape (i.e., rod or cylinder), which may be formed in a manner similar to other extrudates or cast, molded or pressed particles. In some embodiments, these catalytic materials are assembled as a stack of parallel cylinders to create an area of channels similar to the area of channels through a monolith with a larger solid to void ratio. Reducing the void ratio can be advantageous in increasing the gas linear velocity through these channels and potentially provide a better reactor volume utilization.

Benefits of the foregoing embodiments include promoting heat conduction through the solid form in a counter flow direction. In certain embodiments, the form in this case is designed to have an increased heat of conduction by having a core/shell structure or by using a high concentration of SiC within the form.

Other forms that have a much longer length than their other dimensions can also be used to form self-assembled monolith like structures. In some embodiments, catalytic materials in the shape of straight non-nesting helicoidal ribbons are used to form a monolith type structure with hybrid properties between a monolith and a foam (interconnected void and radial mixing, but lower pressure drop and preferential heat flux direction).

In a variant of certain embodiments of the invention, shaped catalytic materials having a defined porosity in the range of large mesopores or small macropores are used. These catalytic materials have a pore volume of >0.15 ml/g, preferably >0.20 ml/g, particularly preferably >0.30 ml/g, >0.50 ml/g, >0.75 ml/g or even >1.0 ml/g for pore diameters greater than 5 nm.

In some embodiments, the formed aggregate, such as an extrudate, comprises an inactive core (e.g., formed from binder, and/or diluents/carriers) and the active catalyst is disposed on the surface of the formed aggregate. Such embodiments provide advantages related to thermal management since the overall catalyst loading is typically lower and the inactive core provides a heat sink.

In these embodiments, the coated inactive core can be porous or non-porous with a catalyst containing outer layer of few microns (e.g., 1-10 or even up to 100) to a few hundreds of micron thick (e.g., 100-1000). In certain embodiments, the outer layer is composed of the active catalyst component exclusively or is formed from a composite with an additional diluent. The additional diluent and/or binder in the outer coat is selected to provide mechanical or heat management benefits to the form.

Alternatively, the core of the form may contain active catalyst while the shell surrounding the active core contains substantially inactive material. In this case the outer shell may be selected to provide mechanical benefits (attrition resistance for example) or diffusion resistance benefits.

The foregoing embodiment is thought to promote a local environment within the core of the active form leading to improved OCM reaction selectivity by decreasing the local $O_2$ concentration, increasing local temperature and/or creating a sharp gradient of concentration of intermediate radicals when the ratio of these radicals becomes unfavorable. In the case of diffusion resistance tuning on the boundary layer between flowing gas between a formed particle and active catalyst located in the core of the particle, certain desirable effects include:

1—tuning of temperature gradient within the particle (typically larger than if no inactive coating present);
2—creation of oxygen gradient in non-catalytically active zone (as O2 is the sub-stoichiometric specie large O2 concentration gradient could be form within the particles without any differential permeation between fuel and oxygen); and
3—quenching of radicals leading to undesirable products (oxygenated radicals having a longer life time than methyl radical), capture of these radical between their place of origin (active catalyst surface) and the void space between forms may improve selectivity of the reaction without depressing overall activity.

In other related embodiments, the inactive shell of the catalytic form is prepared from a substance in which transport of solid oxygen O* becomes competitive with transport of $O_2$, thus further decreasing local $O_2$ concentration around the active catalyst. Examples of such materials include, but are not limited to, yttria stabilized zirconia, non-stoichiometric cerium zirconates and the like.

In certain other embodiments, the catalytic materials are provided in the form of a powder comprising an active catalyst and substantially no binder or diluents material. Rather than forming a formed aggregate as described above, such catalytic powders are contained within a monolith structure, such as a ceramic monolith. The catalytic powder may be encased within an inner void of a monolith, and the monolith is provided with an inlet for feed gas and an outlet. In certain embodiments, the inner void in which the catalytic powder is encased comprises porous walls through which a gas (feed gas and/or product gas, etc.) can flow.

In some embodiments the monolith comprises first and second volumes and a third volume comprising catalytic powder interposed therebetween, wherein the monolith is configured such that feed gas is directed into the first volume, and through the catalytic powder, and reaction product is directed out through the third volume. In some embodiments of the above, the monolith comprises a plurality of first, second and third volumes connected in series such that feed gas is directed sequentially through each first, second and third volume in serially. In other embodiments, the monolith comprises a plurality of first, second and third volumes connected in parallel such that feed gas is directed through each first, second and third volume substantially simultaneously. Other embodiments include a plurality of first, second and third volumes connected in a combination of serial and parallel fashions.

The above described embodiment provides numerous advantages. For example, the immediately foregoing embodiment provides for use of powdered catalyst without the need for dilution with diluents and/or binders, but still allows for adequate flow of gas though the active catalyst. Providing the catalyst in powdered form as described also enables an increased surface area of active catalyst in contact with the feed gas and reduces the linear velocity of the gas through the active catalyst bed. Finally, such embodiments provide for an increased light off temperature/extinction hysteresis, thus increasing feed inlet temperature range of operation at low temperature.

In certain embodiments, the catalytic forms are monoliths, and the catalysts are impregnated within the monolith and/or disposed on the surface of the monolith. In some embodiments, a flow through monolith structure made of nanowire and diluent is provided. Such a monolith is beneficial in an OCM application as it provides a combination of high overall space velocity with reduced local linear velocities as well as forcing contact of the feed gas with the catalyst within the form (regardless of thickness). The low linear velocity of this form can promote a steep temperature gradient that enables reduced extinction temperatures.

As noted above, some embodiments are directed to catalysts (e.g., nanowires) adhered to the surface of a monolith support. In certain embodiments where the active catalyst includes nanowires, the nanowires may be adhered to the surface of the monolith in the absence of a binder due to their unique morphology and packing properties. Monoliths include honeycomb-type structures, foams and other catalytic support structures derivable by one skilled in the art. Monoliths include ceramic and/or metal structures. In one embodiment, the support is a honeycomb matrix formed from silicon carbide, and the support further comprises catalytic nanowires disposed on the surface. In other embodiments, the support comprises cordierite or calcium aluminates.

As the OCM reaction is very exothermic, it can be desirable to reduce the rate of conversion per unit volume of reactor in order to avoid run away temperature rise in the catalyst bed that can result in hot spots affecting performance and catalyst life. One way to reduce the OCM reaction rate per unit volume of reactor is to spread the active catalyst onto an inert support with interconnected large pores as in ceramic or metallic foams (including metal alloys having reduced reactivity with hydrocarbons under OCM reaction conditions) or having arrays of channel as in honeycomb structured ceramic or metal assembly.

In one embodiment, a catalytic material comprising a catalytic nanowire as disclosed herein supported on a structured support is provided. Examples of such structure supports include, but are not limited to, metal foams, Silicon Carbide or Alumina foams, corrugated metal foil arranged to form channel arrays, extruded ceramic honeycomb, for example Cordierite (available from Corning or NGK ceramics, USA), Silicon Carbide or Alumina.

In some embodiments, monoliths having an open channel structure are employed. Such monoliths may provide low flow resistance (or backpressure) comprised to other catalytic forms. In the case of OCM catalysis, at the high space velocity used 10,000 to 200,000 h-1 monoliths may have a backpressure advantage over extrudates.

In some embodiments, the monolith comprises a set of parallel void channels, and coated monolith can have a low overall catalyst loading to reactor volume ratio. This property can be used to minimize local hot spots at the millimeter scale and spread out the reaction volume.

At larger length scales, (e.g., in a tubular reactor), because the radial heat transfer is poor within the parallel void channel network, a homogeneously coated monolith would have very large radial gradient. To minimize this large radial gradient issue, some embodiments employ short pieces of catalyst coated monolith combined with inert diluent.

In one embodiment, the catalytic material is in the form of a monolith and the catalytic reaction is performed in an adiabatic reactor. In these embodiments, the temperature gradient across the flow direction is dictated by the catalyst activity and mass transport limitation and can be controlled based on flow and feed conditions as well as catalyst loading.

Because the weight to volume ratio of the support is very low in a monolith supported catalytic material, it also has relatively low thermal inertia that could speed up startup. Accordingly, certain embodiments provide catalytic materials which allow for faster startup of chemical processes than on other known process. In other embodiments, the monolith is thermally treated prior to coating and has very good mechanical properties, thus decoupling the need to optimize catalytic performance from the need to optimize mechanical durability.

Figure 1A:
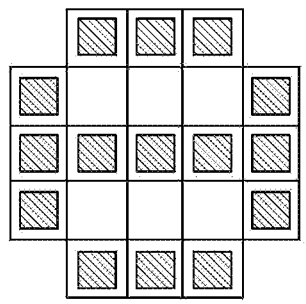
Figure 1D:
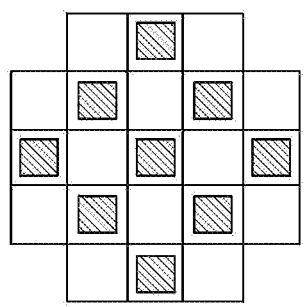

FIGS. 1A-1E depict an embodiment of the invention wherein the catalytic material is in the form of a monolith comprising void channels, wherein the void channels contain little or no active catalysts (dark squares indicate channels containing active catalyst). As illustrated in FIG. 1, the monolith can contain varying numbers of void channels and active channels. FIG. 1A depicts a monolith having no active catalyst, while FIGS. 1B-1E depict monoliths wherein 33%, 71%, 43% or 62%, respectively, of the channels contain active catalyst. In some embodiments every alternate channel in a checker pattern is coated with catalyst and the remaining channels are left uncoated. In such embodiments, only about half of the feed gas will be converted into products while all the gas will be heated up by the exothermic reaction since there is some heat exchange between adjacent channels. In other embodiments, about 10%, about 25%, about 50% to about 75% of the channels contain active catalyst and the other channels are void (i.e., contain substantially no active catalyst). In some cases, these void channels may be used to assist in temperature control throughout a given reactor. In particular, the void channels may be provided with recycled product gas that is at elevated temperature, in order to heat the reactor to a desired temperature, or they may be provided with unreacted feed gases, in order to keep the overall reactor temperature lower, as well as impart heat to the feed gases, without requiring the use of an external heat source. Advantageously, some embodiments include monoliths in which there is sufficient porosity through the wall of the monolith, and some of the oxygen from the uncoated channel may diffuse into the active channel and also be used in the OCM reaction.

In alternate embodiments, monoliths with significant fraction of catalyst within the monolith wall are configured to force the feed gas to flow across the catalytically active walls. This is achieved by plugging alternate channels on each monolith face blocking direct flow through the length of the channel. A "flow through wall" monolith advantageously separates the void volume containing products and feed gases. This minimizes the risk of product destruction thanks to very sharp oxygen concentrations gradients across the monolith walls. At the same time, very sharp T gradients across the monolith walls are obtained with a relatively low gas linear velocity across the wall. This combination of low local flow rate and large T gradient enables running the inlet gas at much reduced temperatures compared to light off temperature potentially reducing the number of catalyst stage needed in a multistage adiabatic reactor.

Other embodiments are directed to catalytic materials comprising an active catalyst supported on a foil. For example, in some embodiments a metal foil is coated with active catalysts in a manner described above with respect to monoliths. The metal foil is selected to be compatible with the particular reaction of interest (e.g., does not destroy reaction intermediates or products, etc.).

In some embodiments, the foil is a FeCrAlY foil. Such foils comprise good corrosion resistance under both rich and lean conditions. A benefit of the metal foil over certain ceramic substrates for coating with catalyst is the fact that foil geometry can easily be changed and coating of selected area can be obtained prior to assembly of the foil packs. In some embodiments, a multilayer coating can also be easily engineered on a metal foil. For example a barrier coat on top of an OCM active coat can be used to promote increase local temperature or a layer can be included to protect the active catalyst against trace elements in the feed gas.

In certain other embodiments, metal foils are employed to increase the heat exchange rate through the catalytic material. This feature may be used to integrate gas to gas heat exchange within the active reactor volume. In other embodiments, catalyst coating on only one side of the foil can be used to assemble alternating active and inactive channels with no exchange between the two sides. This can enable partial conversion of the feed in multiple stages without oxygen injection staging.

In still other embodiments, a catalytic material comprising an active catalyst disposed upon and/or impregnated in a ceramic or metal foam are provided. Foams provide good mixing through the interconnected nature of the foam pore structure and turbulent flow the tortuous pore network. Thus, these embodiments provide rapid mixing of reactant gases.

Some embodiments of the monoliths, (e.g., ceramic foams) of the invention comprise a layer of the active catalyst of average thickness ranging from about 1 to 200 microns, for example from about 100 to 200 microns or about 120 microns. The thickness of the layer may be determined by choice of catalyst content of the impregnating phase. In general, the greater the layer thickness the greater the increase in surface area of the foam, and the greater the tortuosity and pressure drop presented by the foam.

Suitable ceramic foams to be employed in the present invention are for example those having at least 30 pores per inch. Commercially available foams are generally in the range of up to 150 pores per inch. The choice of foam will generally depend on the intended use, whereby increase in pores per inch rating generally corresponds to an increase in tortuosity and pressure drop of a fluid (e.g., reactant gas) passed through the foam. In specific applications there is a need for a high tortuosity foam. The term "tortuosity" is a common term which, when referring to a fixed catalyst bed, can be defined as the ratio of the length of the path taken by a gas flowing through the bed to the length of the shortest straight line path through the bed. Thus a non-tortuous bed, such as a honeycomb monolith structure, has a tortuosity of 1.0. Suitably ceramic foams of the present invention have a tortuosity of at least 1.0, at least 1.1, for example of 1.1 to 10.0, more preferably of 1.1 to 5.0, most preferably of 1.3 to 4.0.

In some embodiments, the ceramic foam comprises a network of irregular passages extending therethrough, said passages having an average minimum dimension in the range 20 to 300 microns, said foam having a total porosity in the range 40 to 85% and an apparent density of at least 0.7 g/cm$^3$. The foam may be made by forming a negative replica of an open cell plastics foam by impregnation of the latter with a dispersion of the ceramic material, followed by drying and calcining the impregnated foam to remove the plastics material and to cause the ceramic material to sinter.

The apparent density of the ceramic foam, i.e., the density as determined by measurement of the external dimensions and the weight, is preferably below 5 g/cm$^3$, and in particular is in the range 0.1 to 2.5 g/cm$^3$, for example 0.1 to 0.3 g/cm$^3$ or about 0.2 g/cm$^3$. Where the pieces of the ceramic foam are of an irregular shape, e.g. granules obtained by fragmentation, so that their volume is not readily determined by measuring the external dimensions of the pieces, the apparent density may be determined from the weight of the pieces and the bulk density of a bed of the pieces assuming a packing fraction appropriate to pieces of that shape and size distribution. Alternatively it may be appropriate to assume that the pieces approximate to a geometric shape whose volume can be calculated from the dimensions. Alternatively the volume may be determined by filling at least the outer pores of the ceramic foam with a suitable material, e.g., wax, and determining the volume by displacement of a suitable fluid.

The porosity of the ceramic foams can be expressed in terms of the pore volume fraction, that is the fraction of the volume which is occupied by the pores. Pore volume fraction is determined by dividing the volume of ceramic material by the total volume of the foam and multiplying by 100. The pore volume fraction of the ceramic foams is generally greater than 50%, for example from about 75% to about 95%.

The porosity of the ceramic foams may also be characterized in terms of the total pore volume. The ceramic foams employed in the present invention preferably have a total pore volume of less than 2 cm$^3$/g, and particularly in the range 0.2 to 1.5 cm$^3$/g, and most preferably in the range 0.2 to 0.8 cm$^3$/g. By the term total pore volume it is meant the volume of the foam as determined by its external dimensions less the volume occupied by the ceramic material itself. The latter may be determined by measuring the helium density. The total pore volume is the difference between the reciprocal of the helium density and the reciprocal of the apparent density. In the ceramic foams of the present invention, part of the total pore volume is in the form of relatively large pores, herein termed megapores, whereas the remainder is in the form of pores of sizes normally encountered in ceramic catalyst supports. Conventionally, the pore volume of a ceramic catalyst support is determined from measurement of the density in mercury and the density in helium (both measured at atmospheric pressure). In the foams employed in the present invention the pore volume determined in this way, i.e., the difference between the reciprocal of the mercury density and the reciprocal of the helium density, is termed the micropore volume, and is typically in the range 0.02 to 0.3 cm$^3$/g. It will be appreciated that the apparent density, total pore volume and micropore volume, will of course depend to some extent on the nature of the ceramic material.

The total porosity, which is the product of the total pore volume and the apparent density, and is expressed as a percentage, of the ceramic foams employed in the present invention is in the range 40 to 85%, preferably 50 to 80%, and is generally less than materials made by the aforesaid methods involving removal of ceramic dispersion from the impregnated foam by squeezing or by means of an air blast. Foams made by that method generally have a total porosity above about 85%, a total pore volume above about 1.6 cm$^3$/g and an apparent density below 0.6 g/cm$^3$. From measurement of the mercury density as aforesaid, it is also possible to determine a megaporosity, i.e. the proportion of the overall volume that is in the form of the megapores and hence the ratio of the megaporosity to the total porosity. The megaporosity is the ratio of the difference between the mercury density and the apparent density to the mercury density. The ratio (expressed as a percentage) of the megaporosity to the total porosity is typically in the range 60 to 90%, whereas the materials made as aforesaid by methods involving removal of ceramic material from the impregnated foam by squeezing or by means of an air blast, typically have a megaporosity/total porosity ratio of well above 90%, often about 95% or more.

The surface area of the ceramic foam, as measured by the BET method using nitrogen, is preferably in the range 0.1 to 10 m$^2$/g.

In some other embodiments, the catalytic materials comprise and active catalyst disposed on or impregnated in a gauze (i.e., mesh) structure, for example a wire gauze.

The gauze structure has between $100^2$ to $600^2$ openings per inch$^2$; hence the gauze structure has 1550 to 55800 openings per cm$^2$. Preferably the wire gauze structure has 2000 to 40000, more preferably 2500 to 30000, even more preferably 3000 to 20000 openings per cm$^2$. The size of these openings preferably is in the range of from 280 μm$^2$ to 24000 μm$^2$, more preferably 600 μm$^2$ to 20000 μm$^2$, even more preferably 1400 μm$^2$ to 10000 μm$^2$, most preferably 1400 μm$^2$ to 5500 μm$^2$.

The wires of the gauze have a thickness of 20 micrometer to 110 micrometer. Where the wires cross over each other, the support structure has a total thickness in the range of 40 micrometer to 330 micrometer. After weaving, the thickness of the support structure at the place where the wires cross over each other may be up to 3 times as thick as the wire thickness. In one embodiment the gauze is woven and then pressed before it is used as a support structure in the present invention. In such a case the thickness of the support structure at the place where the wires cross over each other may be up to 2 times as thick as the wire thickness.

The thickness of a wire gauze structure at the place where the wires cross over each other may be determined using a caliper, for example a vernier caliper. The thickness of a wire gauze structure may alternatively or additionally be determined using a microscope or one or more photographs. The thickness of a wire may be determined using a micrometer or a caliper.

In some embodiments, the wires of the wire gauze structure comprise a metal. Preferably the wire structure comprises stainless steel, such as stainless steel 310 or 316, iron, copper and/or aluminum, more preferably stainless steel.

The pattern of the gauze may be chosen from any number of patterns. Examples of suitable patterns are "plain weave" (each wire passes in turn under and over another wire, the wire diameters are usually the same in both directions and the mesh apertures are either square or rectangular), "plain Dutch weave" and a "Dutch twill weave". Preferably the wire gauze has a "plain weave" structure. Bended or twisted wire gauze structures are also included. The gauze structures may be implemented in a reactor system as a stack, roll, pleated or folded sheet, or in any number of a variety of specific configurations.

Active catalyst loading on the above supports ranges from 1 to 500 mg per cm$^3$ of support component, for example from 5 to 100 mg per cm$^3$ of structure support. Cell densities on honeycomb structured support materials may range from 100 to 900 CPSI (cell per square inch), for example 200 to 600 CPSI or about 400 CPSI. Foam densities may range from 10 to 100 PPI (pore per inch), for example 20 to 60 PPI.

In other embodiments, the exotherm of the OCM reaction may be at least partially controlled by blending the active catalytic material with catalytically inert material, and forming (e.g., by pressing or extruding) the mixture into the desired shape, for example shaped pellets or extrudates as discussed above. In some embodiments, these mixed particles may then be loaded into a pack-bed reactor. The formed aggregates comprise between 30% to 70% pore volume and from about 1% (or lower) to 99% active catalyst (by weight). In some embodiments, the formed aggregates comprise from about 5-95% active catalyst, from about 5-90% active catalyst, from about 5-75% active catalyst or from about 5-50% active catalyst. Useful inert materials in this regard include, but are not limited to those described herein above. In certain specific embodiments the inert materials are selected from SiC and cordierite.

In addition to reducing the potential for hot spots within the catalytic reactor, another advantage of using a structured ceramic with large pore volume as a catalytic support is reduced flow resistance at the same gas hourly space velocity versus a pack-bed containing the same amount of catalyst.

Yet another advantage of using such supports is that the structured support can be used to provide features difficult to obtain in a pack-bed reactor. For example the support structure can improve mixing or enabling patterning of the active catalyst depositions through the reactor volume. Such patterning can comprise depositing multiple layers of catalytic materials on the support in addition to the OCM active component in order to affect transport to the catalyst or combining catalytic functions as adding O2-ODH activity, CO2-OCM activity or CO2-ODH activity to the system in addition to O2-OCM active material. Another patterning strategy can be to create bypass within the structure catalyst essentially free of active catalyst to limit the overall conversion within a given supported catalyst volume.

Yet another advantage is reduced heat capacity of the bed of the structured catalyst over a pack bed a similar active catalyst loading therefore reducing startup time.

Nanowire shaped catalysts are particularly well suited for incorporation into formed aggregates, such as pellets or extrudates, or deposition onto structured supports. Nanowire aggregates forming a mesh type structure can have good adhesion onto rough surfaces.

The mesh like structure can also provide improved cohesion in composite ceramic improving the mechanical properties of pellets or extrudates containing the nanowire shaped catalyst particles.

Alternatively, such nanowire on support or in pellet form approaches can be used for other reactions besides OCM, such as ODH, dry methane reforming, FT, and all other catalytic reactions.

In yet another embodiment, the catalysts are packed in bands forming a layered reactor bed. Each layer is composed by either a catalyst of a particular type, morphology or size or a particular blend of catalysts. In one embodiment, the catalysts blend may have better sintering properties, i.e. lower tendency to sinter, then a material in its pure form. Better sintering resistance is expected to increase the catalyst's lifetime and improve the mechanical properties of the reactor bed.

In yet other embodiments, the disclosure provides a catalytic material comprising one or more different catalysts. The catalysts may be a nanowire as disclosed herein and a different catalyst for example a bulk catalysts. Mixtures of two or more nanowire catalysts are also contemplated. The catalytic material may comprise a catalyst, for example a nanowire catalyst, having good OCM activity and a catalyst having good activity in the ODH reaction. Either one or both of these catalysts may be nanowires as disclosed herein.

4. Preparation of Catalytic Materials

The catalytic materials can be prepared according to any number of methods known in the art. For example, the catalytic materials can be prepared after preparation of the individual components (i.e., catalyst, diluent, binder, support, etc.) by mixing the individual components in their dry form, e.g. blend of powders, and optionally, milling, such as ball milling, grinding, granulating, or other similar size reduction processes can be used to reduce particle size and/or increase mixing. Each component can be added together or one after the other to form layered particles. The individual components can be mixed prior to calcination, after calcination or by mixing already calcined components with uncalcined components. The catalytic materials may also be prepared by mixing the individual components in their dry form and optionally pressing them together into a "pressed pellet" or extrudate followed by calcination to above 400° C.

In other examples, the catalytic materials are prepared by mixing the individual components with one or more solvents into a suspension or slurry, and optional mixing and/or milling can be used to maximize uniformity and reduce particle size. Examples of slurry solvents useful in this context include, but are not limited to: water, alcohols, ethers, carboxylic acids, ketones, esters, amides, aldehydes, amines, alkanes, alkenes, alkynes, aromatics, etc. In other embodiments, the individual components are deposited on a supporting material such as silica, alumina, magnesia, activated carbon, and the like, or by mixing the individual components using a fluidized bed granulator. Combinations of any of the above methods may also be used.

Other methods for preparation of catalytic materials include use of a wet filter cake isolated via the method described in U.S. Provisional App. No. 61/594,883, which application is hereby incorporated by reference in its entirety for all purposes. For example, a wet filter cake (i.e., still containing some solvent and/or wash solution) can be extruded to form extrudates directly. An optional binder may be included in the wet cake prior to extrusion. Further, the wet cake may also optionally be washed with a solution containing a dopant or a solid dopant may be added to the wet cake, and the resulting wet cake can be extruded to prepare doped catalytic materials. The solvent content of the wet cake can be controlled to control the rheology of the wet cake to obtain desirable extrudate properties.

The catalytic materials may optionally comprise a dopant. In this respect, doping material(s) may be added during preparation of the individual components, after preparation of the individual components but before drying of the same, after the drying step but before calcinations or after calcination. Dopants may also be impregnated into, or adhered onto formed aggregates, or as layers applied upon supports for formed aggregates, prior to addition of one or more different materials, e.g., catalyst materials, diluents, binders, other dopants, etc. If more than one doping material is used, each dopant can be added together or one after the other to form layers of dopants.

Doping material(s) may also be added as dry components and optionally ball milling can be used to increase mixing. In other embodiments, doping material(s) are added as a liquid (e.g. solution, suspension, slurry, etc.) to the dry individual catalyst components or to the blended catalytic material. The amount of liquid may optionally be adjusted for optimum wetting of the catalyst, which can result in optimum coverage of catalyst particles by doping material. Mixing, grinding and/or milling can also be used to maximize doping coverage and uniform distribution. Alternatively, doping material(s) are added as a liquid (e.g. solution, suspension, slurry, etc.) to a suspension or slurry of the catalyst in a solvent. Mixing and/or milling can be used to maximize doping coverage and uniform distribution. Incorporation of dopants can also be achieved using any of the methods described elsewhere herein.

An optional calcination step may follow an optional drying step at T<200° C. (typically 60-120° C.) in a regular oven or in a vacuum oven. Calcination may be performed on the individual components of the catalytic material or on the blended catalytic material. Calcination is generally performed in an oven/furnace at a temperature higher than the minimum temperature at which at least one of the components decomposes or undergoes a phase transformation and can be performed in inert atmosphere (e.g. $N_2$, Ar, He, etc.), oxidizing atmosphere (air, $O_2$, etc.) or reducing atmosphere ($H_2$, $H_2/N_2$, $H_2/Ar$, etc.). The atmosphere may be a static atmosphere or a gas flow and may be performed at ambient pressure, at p<1 atm, in vacuum or at p>1 atm. High pressure treatment (at any temperature) may also be used to induce phase transformation including amorphous to crystalline. Calcinations may also be performed using microwave heating.

Calcination is generally performed in any combination of steps comprising ramp up, dwell and ramp down. For example, ramp to 500° C., dwell at 500° C. for 5h, ramp down to RT. Another example includes ramp to 100° C., dwell at 100° C. for 2h, ramp to 300° C., dwell at 300° C. for 4h, ramp to 550° C., dwell at 550° C. for 4h, ramp down to RT. Calcination conditions (pressure, atmosphere type, etc.) can be changed during the calcination. In some embodiments, calcination is performed before preparation of the blended catalytic material (i.e., individual components are calcined), after preparation of the blended catalytic material but before doping, after doping of the individual components or blended catalytic material. Calcination may also be performed multiple times, e.g. after catalyst preparation, after aggregate formation, and/or after doping, as well as upon any or all of the individual components that are added to the formed aggregate, e.g., dopants, catalysts, diluents, supports, etc.

The catalytic materials may be incorporated into a reactor bed for performing any number of catalytic reactions (e.g., OCM, ODH and the like). Accordingly, in one embodiment the present disclosure provides a catalytic material as disclosed herein in contact with a reactor and/or in a reactor bed. For example, the reactor may be for performing an OCM reaction (i.e., an OCM reactor), may be a fixed bed reactor and may have a diameter greater than 1 inch. In this regard, the catalytic material may be packed neat (without diluents) or diluted with an inert material (e.g., sand, silica, alumina, etc.) The catalyst components may be packed uniformly forming a homogeneous reactor bed.

The particle size of the individual components within a catalytic material may also alter the catalytic activity, and other properties, of the same. Accordingly, in one embodiment, the catalyst is milled to a target average particle size and may be optionally sieved to select a particular particle size range. In some aspects, the catalyst powder is further processed into extrudates or pellets and the extrudates or pellets are optionally milled and/or sieved to obtain the desired particle size distribution.

In some embodiments, the catalyst materials, alone or with binders and/or diluents, can be configured into larger aggregate forms, such as pellets, extrudates, or other aggregations of catalyst particles. Such larger aggregate forms may optionally include a binder and/or support material; however, the present inventors have surprisingly found that certain nanowire catalysts are particularly suited to use in the form of a pellet without a binder and/or support material. Accordingly, one embodiment of the disclosure provides a catalytic material in the absence of a binder. In this regard, the morphology of certain catalytic nanowires (either bent or straight, etc.) is believed to contribute to the nanowires' ability to be pressed into extrudates without the need for a binder. Catalytic materials without binders are simpler, less complex and may be cheaper than corresponding materials with binders and thus offer certain advantages such as the ability to load the catalyst in pack-beds with a low pressure drop under operating conditions.

In some instances, catalytic materials may be prepared using a binder or support to maintain the catalyst formulation as a cohesive structure. A variety of materials may be employed as a binder. For example, in some embodiments catalytic materials in the form of extrudates comprising catalytic nanowires can be prepared without the use of a separate binder. In other words, because of their unique properties, nanowire materials, including the nanowire catalysts described elsewhere herein, can function to provide the requisite structural cohesion of a binder material. Certain bulk catalysts are also useful in this regard.

In some cases, a sacrificial binder may be used. A "sacrificial" binder can be used in order to create unique microporosity in formed aggregates (e.g., pellets or extrudates). After removing the sacrificial binder, the structural integrity of the catalyst is ensured by the special binding properties of the catalyst (e.g., nanowires). For example, in some embodiments a catalytic material may be prepared with a binder and then the binder removed by any number of techniques (e.g., combustion, calcinations, acid erosion, etc.). This method allows for design and preparation of catalytic materials having unique microporosity (i.e., the microporosity is a function of size, etc. of the sacrificial binder). The ability to prepare different form aggregates (e.g., pellets) of catalysts, such as nanowires, without the use of a binder is not only useful for preparation of catalytic materials from nanowires, but also allows the nanowires to be used as support materials (or both catalytic and support material). Sacrificial binders and techniques useful in this regard include sacrificial cellulosic fibers or other organic polymers that can be easily removed by calcination, non-sacrificial binders and techniques useful in this regard include, colloidal oxide binders such as Ludox Silica or Nyacol colloidal zirconia that can also be added to strengthen the formed aggregate when needed. Sacrificial binders are added to increase macro-porosity (pores larger than 20 nm diameter) of the catalytic materials. Accordingly, in some embodiments the catalytic materials comprise pores greater than 20 nm in diameter, greater than 50 nm in diameter, greater than 75 nm in diameter, greater than 100 nm in diameter or greater than 150 nm in diameter.

The catalytic forms in the form of formed aggregates can be obtained, for example, by kneading or pan-milling of the starting compounds with the binder, for example any of the binders described herein, forming (e.g., extruding, casting, molding and the like) and subsequently calcining. The binder can be pretreated prior to extrusion. This is preferably carried out by means of acid, for example formic acid or nitric acid. Other auxiliaries, for example pore formers such as carboxymethylcellulose, potato starch or stearic acid, can be additionally added prior to or during extrusion.

Other processes for preparing catalytic forms include drying a composite wet "cake" obtained by filtration or centrifugation before fragmenting such dry cake into mm size pieces, e.g., through grinding, milling or the like. The composite wet cake generally comprises the active catalyst and a binder and/or diluents/carrier material. Casting of a catalyst containing paste is also be used to create complex forms prior to drying and calcination. The catalytic materials may also be isolated and/or doped according to the procedures described in U.S. Provisional App. No. 61/594,883, which application is hereby incorporated by reference in its entirety for all purposes.

In another embodiment, formed aggregates are prepared by sequential addition of the components of the final catalytic form. In this case forming or pelletizing the diluent or carrier component with inactive binders as needed is performed first. The inactive form is then calcined at elevated temperature to provide a mechanically strong object. The active catalyst is then contacted with the form. In certain embodiments, soluble salt precursors of the catalyst are used in this step with a high surface area carrier (or diluent or support) to promote the formation of dispersed catalyst on the support.

In embodiments wherein the catalyst is a nanowire, the catalyst is typically synthesized separately through controlled precipitation or crystallization, and in some further embodiments the support does not need to have a high surface area. However, if a homogeneous distribution of the catalytic solids is to be obtained, large pores within the form are needed to enable diffusion of the nanowire shape solid into the form. Pores on the order a few microns (e.g., about 1-10, or 1-100 microns) are desirable in this case. Dispersed nanowire suspensions in a liquid that easily wets the diluent (or carrier) are used to deposit the active component into the pores of the pre-calcined form. For example, the nanowire catalyst is coated on the inactive form by conventional methods such as dip-coating, spray-coating, and related methods. In certain embodiments, nanowire or nano-colloids may be advantageous compared to traditional bulk catalyst in this post impregnation process by enabling the addition of a large amount of catalyst by impregnation iteration onto a form with micron size pores.

In other embodiments, catalytic materials comprising nanowire catalysts can also be formed within a porous form by adding the selected form to the nanowire synthesis solution.

In yet other embodiments, separate calcinations of the catalytic material can be used at different stage of the synthesis. In this manner, strong bonds between carrier grains and/or carrier grains and binder can be formed in a first calcination step without degrading the active catalyst component.

In other examples, wet impregnation of the form containing an active catalyst (e.g., OCM catalyst) component can also be used to further promote activity or selectivity of the formed material. For example, in some embodiments the catalyst form is impregnated with a soluble salt comprising a dopant, thus producing a doped catalytic material. Methods for impregnating or coating a dopant on or in a catalytic form include dip-coating or immersion coating, and/or spray coating as described above. In certain embodiments, a low surface area carrier (or diluent) is used and most of the surface area within the catalytic form comes from the active catalyst itself. This high surface area ratio between catalytic and non-catalytic components within the form favors interaction between the active catalyst component and the doping element added to the form.

After shaping, the formed aggregates are dried and if appropriate calcined. The usual calcination temperatures for the catalytic materials are from 300 to 1000° C., from 400 to 800 C, from 500 to 700° C. or from 550 to 650° C., at calcination times of from 5 minutes to 5 hours, preferably from 10 minutes to 2 hours.

Deposition of the catalyst on a support, such as a monolith, can be performed by wash-coating which is contacting a slurry containing the catalyst with the monolith walls and removing the excess slurry prior to drying and calcination of the monolith.

Deposition of the catalyst on supports can also be performed by growing the nanowire within the monolith channel by immersing the monolith into the solution used to grow the catalyst (e.g., nanowires). In this case the wire mesh is likely to be filling all the volume of the channel with low density mesh prior to drying. During drying the gel can contract leaving mostly open channels or dry without pulling the solid mesh toward the walls (depending on surface tension of liquid and adhesion to the walls) leaving an inorganic aerogel in the channel.

In some other embodiments, the catalytic material is in the form of a monolith and the active catalyst comprises a nanowire. In such embodiments, the monoliths may be prepared from a nanowire containing composite mixture by extrusion or casting.

For ease of illustration, the above description of catalytic materials often refers to OCM; however, such catalytic materials find utility in other catalytic reactions including but not limited to: oxidative dehydrogenation (ODH) of alkanes to their corresponding alkenes, selective oxidation of alkanes and alkenes and alkynes, oxidation of co, dry reforming of methane, selective oxidation of aromatics, Fischer-Tropsch, combustion of hydrocarbons, etc. as discussed in more detail below.

One skilled in the art will recognize that various combinations or alternatives of the above methods are possible, and such variations are also included within the scope of the present disclosure.

Catalytic Reactions

The present disclosure provides for the use of the disclosed catalytic materials in catalytic reactions and related methods. In some embodiments, the catalytic reaction is any of the reactions described herein. The morphology and composition of the catalysts in the catalytic materials is not limited. For example the catalysts may be a nanowire having a bent morphology or a straight morphology and may have any molecular composition or the catalyst may be a bulk catalyst, or any combination thereof.

The disclosed catalytic materials may be useful in any number of reactions catalyzed by a heterogeneous catalyst. Examples of reactions wherein the disclosed catalytic materials may be employed are disclosed in Farrauto and Bartholomew, "Fundamentals of Industrial Catalytic Processes" Blackie Academic and Professional, first edition, 1997, which is hereby incorporated in its entirety. Other non-limiting examples of reactions wherein the disclosed catalytic materials may be employed include: the oxidative coupling of methane (OCM) to ethane and ethylene; oxidative dehydrogenation (ODH) of alkanes to the corresponding alkenes, for example oxidative dehydrogenation of ethane or propane to ethylene or propylene, respectively; selective oxidation of alkanes, alkenes, and alkynes; oxidation of CO, dry reforming of methane, selective oxidation of aromatics; Fischer-Tropsch, hydrocarbon cracking; combustion of hydrocarbons and the like. Reactions catalyzed by the disclosed catalytic materials are discussed in more detail below.

The disclosed catalytic materials are generally useful in methods for converting a first carbon-containing compound (e.g., a hydrocarbon, CO or $CO_2$) to a second carbon-containing compound. In some embodiments the methods comprise contacting a catalytic material disclosed herein with a gas comprising a first carbon-containing compound and an oxidant to produce a carbon-containing compound. In some embodiments, the first carbon-containing compound is a hydrocarbon, CO, $CO_2$, methane, ethane, propane, hexane, cyclohexane, octane or combinations thereof. In other embodiments, the second carbon-containing compound is a hydrocarbon, CO, $CO_2$, ethane, ethylene, propane, propylene, hexane, hexene, cyclohexane, cyclohexene, bicyclohexane, octane, octene or hexadecane. In some embodiments, the oxidant is oxygen, ozone, nitrous oxide, nitric oxide, carbon dioxide, water or combinations thereof.

In other embodiments of the foregoing, the method for conversion of a first carbon-containing compound to a second carbon-containing compound is performed at a temperature below 100° C., below 200° C., below 300° C., below 400° C., below 500° C., below 550° C., below 600° C., below 700° C., below 800° C., below 900° C. or below 1000° C. In other embodiments, the method for conversion of a first carbon-containing compound to a second carbon-containing compound is performed at a pressure above 0.5 ATM, above 1 ATM, above 2 ATM, above 5 ATM, above 10 ATM, above 25 ATM or above 50 ATM.

In certain embodiments of the foregoing method, the catalytic materials comprise a catalytic nanowire. In other embodiments, the catalytic materials comprise a bulk catalyst.

The catalytic reactions described herein can be performed using standard laboratory equipment known to those of skill in the art, for example as described in U.S. Pat. No. 6,350,716, which is incorporated herein by reference in its entirety.

1. Oxidative Coupling of Methane (OCM)

The present disclosure provides catalytic materials for improving the yield, selectivity and/or conversion of any number of catalyzed reactions, including the OCM reaction. Reactors useful in practice of the OCM methods described herein are known in the art and are described in U.S. Provisional App. entitled "Oxidative Coupling of Methane Systems and Methods" and filed May 24, 2012, which application is hereby incorporated by reference in its entirety. As mentioned above, there exists a tremendous need for catalyst technology capable of addressing the conversion of methane into high value chemicals (e.g., ethylene and products prepared therefrom) using a direct route that does not go through syngas. Accomplishing this task will dramatically impact and redefine a non-petroleum based pathway for feedstock manufacturing and liquid fuel production yielding reductions in GHG emissions, as well as providing new fuel sources.

Ethylene has the largest carbon footprint compared to all industrial chemical products in part due to the large total volume consumed into a wide range of downstream important industrial products including plastics, surfactants and pharmaceuticals. In 2008, worldwide ethylene production exceeded 120 M metric tons while growing at a robust rate of 4% per year. The United States represents the largest single producer at 28% of the world capacity. Ethylene is primarily manufactured from high temperature cracking of naphtha (e.g., oil) or ethane that is separated from natural gas. The true measurement of the carbon footprint can be difficult as it depends on factors such as the feedstock and the allocation as several products are made and separated during the same process. However, some general estimates can be made based on published data.

Cracking consumes a significant portion (about 65%) of the total energy used in ethylene production and the remainder is for separations using low temperature distillation and compression. The total tons of $CO_2$ emission per ton of ethylene are estimated at between 0.9 to 1.2 from ethane cracking and 1 to 2 from naphtha cracking. Roughly, 60% of ethylene produced is from naphtha, 35% from ethane and 5% from others sources (Ren, T.; Patel, M. *Res. Conserv. Recycl.* 53:513, 2009). Therefore, based on median averages, an estimated amount of $CO_2$ emissions from the cracking process is 114M tons per year (based on 120M tons produced). Separations would then account for an additional 61M tons $CO_2$ per year.

The disclosed catalytic materials provide an alternative to the need for the energy intensive cracking step. Additionally, because of the high selectivity of the catalytic materials, downstream separations are dramatically simplified, as compared to cracking which yields a wide range of hydrocarbon products. The reaction is also exothermic so it can proceed via an autothermal process mechanism. Overall, it is estimated that up to a potential 75% reduction in $CO_2$ emission compared to conventional methods could be achieved. This would equate to a reduction of one billion tons of $CO_2$ over a ten-year period and would save over 1M barrels of oil per day.

The catalytic materials also permit converting ethylene into liquid fuels such as gasoline or diesel, given ethylene's high reactivity and numerous publications demonstrating high yield reactions, in the lab setting, from ethylene to gasoline and diesel. On a life cycle basis from well to wheel, recent analysis of methane to liquid (MTL) using F-T process derived gasoline and diesel fuels has shown an emission profile approximately 20% greater to that of petroleum based production (based on a worst case scenario) (Jaramillo, P., Griffin, M., Matthews, S., *Env. Sci. Tech* 42:7559, 2008). In the model, the $CO_2$ contribution from plant energy was a dominating factor at 60%. Thus, replacement of the cracking and F-T process would be expected to provide a notable reduction in net emissions, and could be produced at lower $CO_2$ emissions than petroleum based production.

Furthermore, a considerable portion of natural gas is found in regions that are remote from markets or pipelines. Most of this gas is flared, re-circulated back into oil reservoirs, or vented given its low economic value. The World Bank estimates flaring adds 400M metric tons of $CO_2$ to the atmosphere each year as well as contributing to methane emissions. The nanowires of this disclosure also provide economic and environmental incentive to stop flaring. Also, the conversion of methane to fuel has several environmental advantages over petroleum-derived fuel. Natural gas is the cleanest of all fossil fuels, and it does not contain a number of impurities such as mercury and other heavy metals found in oil. Additionally, contaminants including sulfur are also easily separated from the initial natural gas stream. The resulting fuels burn much cleaner with no measurable toxic pollutants and provide lower emissions than conventional diesel and gasoline in use today.

In view of its wide range of applications, the catalytic materials of this disclosure can be used to not only selectively activate alkanes, but also to activate other classes of inert unreactive bonds, such as C—F, C—Cl or C—O bonds. This has importance, for example, in the destruction of man-made environmental toxins such as CFCs, PCBs, dioxins and other pollutants. Accordingly, while the invention is described in greater detail below in the context of the OCM reaction and other the other reactions described herein, the catalytic materials are not in any way limited to these particular reactions.

The selective, catalytic oxidative coupling of methane to ethylene (i.e. the OCM reaction) is shown by the following reaction (1):

$$2CH_4 + O_2 \rightarrow CH_2CH_2 + 2H_2O \quad (1)$$

Figure 2:
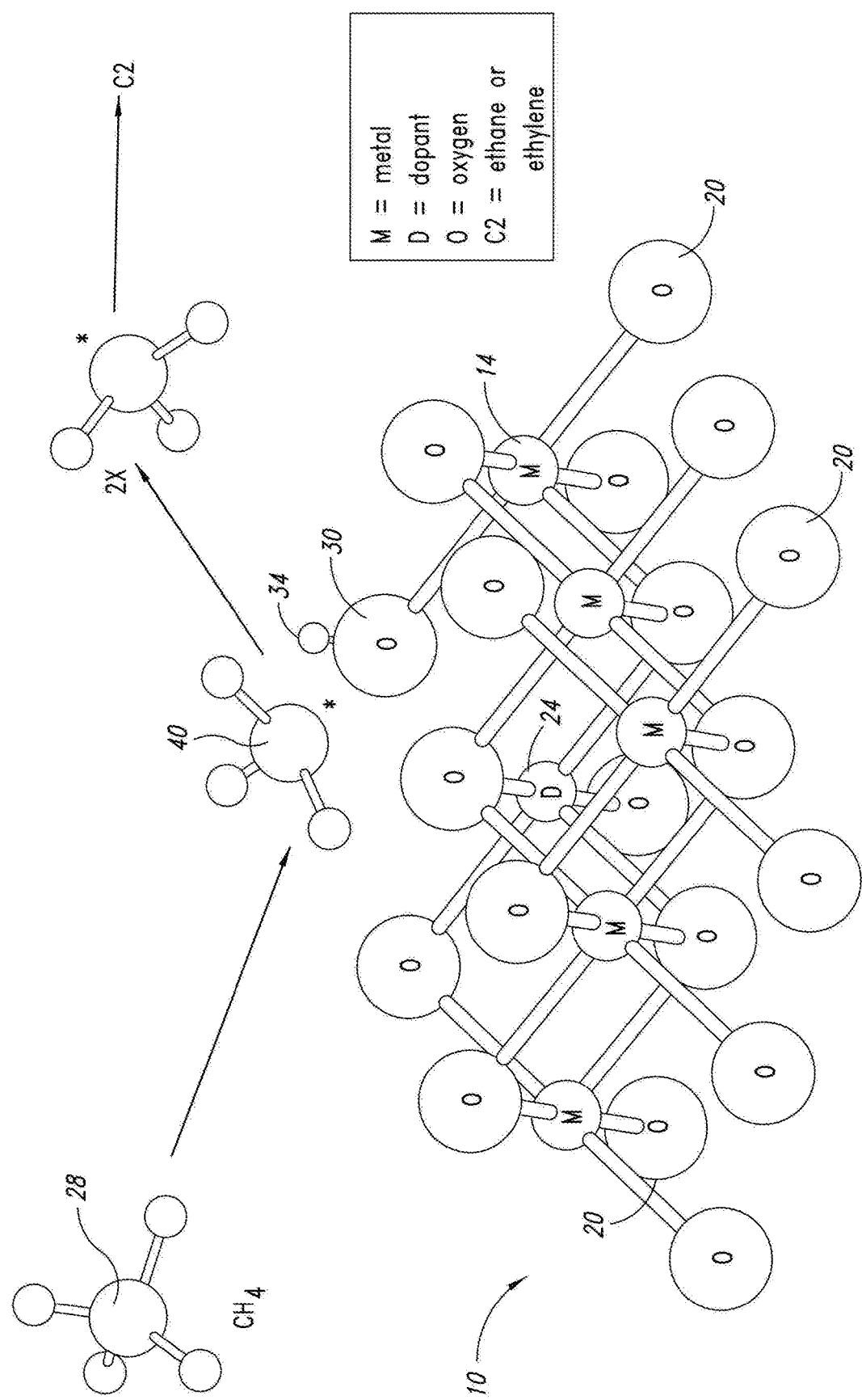
FIG. 2 schematically depicts the oxidative coupling of methane (OCM) reaction.

The OCM reaction on the surface of a heterogeneous catalyst is schematically depicted in FIG. 2. This reaction is exothermic (Heat of Reaction −67 kcals/mole) and usually occurs at very high temperatures (>700° C.). During this reaction, it is believed that the methane ($CH_4$) is first oxidatively coupled into ethane ($C_2H_6$), and subsequently the ethane ($C_2H_6$) is oxidatively dehydrogenated into ethylene ($C_2H_4$). Because of the high temperatures used in the reaction, it has been suggested that the ethane is produced mainly by the coupling in the gas phase of the surface-generated methyl ($CH_3$) radicals. Reactive metal oxides (oxygen type ions) are apparently required for the activation of $CH_4$ to produce the $CH_3$ radicals. The yield of $C_2H_4$ and $C_2H_6$ is limited by further reactions in the gas phase and to some extent on the catalyst surface. A few of the possible reactions that occur during the oxidation of methane are shown below as reactions (2) through (8):

$$CH_4 \rightarrow CH_3 \text{ radical} \quad (2)$$

$$CH_3 \text{ radical} \rightarrow C_2H_6 \quad (3)$$

$$CH_3 \text{ radical} + 2.5O_2 \rightarrow CO_2 + 1.5 H_2O \quad (4)$$

$$C_2H_6 \rightarrow C_2H_4 + H_2 \quad (5)$$

$$C_2H_6 + 0.5O_2 \rightarrow C_2H_4 + H_2O \quad (6)$$

$$C_2H_4 + 3O_2 \rightarrow 2CO_2 + 2H_2O \quad (7)$$

$$CH_3 \text{ radical} + C_xH_y + O_2 \rightarrow \text{Higher HC's-Oxidation/} CO_2 + H_2O \quad (8)$$

With conventional heterogeneous catalysts and reactor systems, the reported performance is generally limited to <25% $CH_4$ conversion at <80% combined $C_2$ selectivity, with the performance characteristics of high selectivity at low conversion, or the low selectivity at high conversion. In contrast, the catalytic materials of this disclosure are highly active and can optionally operate at a much lower temperature. In one embodiment, the catalytic materials disclosed herein enable efficient conversion (i.e., high yield, conversion, and/or selectivity) of methane to ethylene at temperatures of less than 900° C., less than 800° C., less than 700° C., less than 600° C., less than 550° C., or less than 500° C. In other embodiments, the use of staged oxygen addition, designed heat management, rapid quench and/or advanced separations may also be employed.

Accordingly, one embodiment of the present disclosure is a method for the preparation of ethane and/or ethylene, the method comprising converting methane to ethane and/or ethylene in the presence of a catalytic material as disclosed herein. In certain embodiments of the foregoing method, the catalytic materials comprise a catalytic nanowire. In other embodiments, the catalytic materials comprise a bulk catalyst.

The exothermic heats of reaction (free energy) follow the order of reactions depicted above and, because of the proximity of the active sites, will mechanistically favor ethylene formation while minimizing complete oxidation reactions that form CO and $CO_2$. Representative catalyst compositions useful for the OCM reaction include, but are not limited to: highly basic oxides selected from the early members of the Lanthanide oxide series; Group 1 or 2 ions supported on basic oxides, such as Li/MgO, Ba/MgO and Sr/$La_2O_3$; and single or mixed transition metal oxides, such as $VO_x$ and Re/Ru that may also contain Group 1 ions. Other nanowire compositions useful for the OCM reaction comprise any of the compositions disclosed herein, for example MgO, $La_2O_3$, $Na_2WO_4$, $Mn_2O_3$, $Mn_3O_4$, $Mg_6MnO_8$, $Zr_2Mo_2O_8$, $NaMnO_4$, $Mn_2O_3/Na_2WO_4$, $Mn_3O_4/Na_2WO_4$ or Na/$MnO_4$/MgO, Mn/WO4, $Nd_2O_3$, $Sm_2O_3$, $Eu_2O_3$ or combinations thereof. Activating promoters (i.e., dopants), such as chlorides, nitrates and sulfates, or any of the dopants described above may also be employed.

Important performance parameters used to measure the catalytic materials' performance in the OCM reaction are selected from single pass methane conversion percentage (i.e., the percent of methane converted on a single pass over the catalyst or catalytic bed, etc.), reaction inlet gas temperature, reaction operating temperature, total reaction pressure, methane partial pressure, gas-hour space velocity (GHSV), $O_2$ source, catalyst stability and ethylene to ethane ratio.

In certain embodiments, the inlet gas temperature in an OCM reaction catalyzed by the disclosed catalytic materials is <700° C., <675° C., <650° C., <625° C., <600° C., <593° C., <580° C., <570° C., <560° C., <550° C., <540° C., <530° C., <520° C., <510° C., <500° C., <490° C., <480° C. or even <470° C. In certain embodiments, the reaction operating temperature (i.e., outlet temperature) in an OCM reaction catalyzed by the disclosed catalytic materials is <950° C., <925° C., <900° C., <875° C., <850° C., <825° C., <800° C., <775° C., <750° C., <725° C., <700° C., <675° C., <650° C., <625° C., <600° C., <593° C., <580° C., <570° C., <560° C., <550° C., <540° C., <530° C., <520° C., <510° C., <500° C., <490° C., <480° C., <470° C.

The single pass methane conversion in an OCM reaction catalyzed by the catalytic materials is generally >5%, >10%, >15%, >20%, >25%, >30%, >35%, >40%, >45%, >50%, >55%, >60%, >65%, >70%, >75% or even >80%.

In certain embodiments, the inlet reaction pressure in an OCM reaction catalyzed by the catalytic materials is >1 atm, >1.1 atm, >1.2 atm, >1.3 atm, >1.4 atm, >1.5 atm, >1.6 atm, >1.7 atm, >1.8 atm, >1.9 atm, >2 atm, >2.1 atm, >2.1 atm, >2.2 atm, >2.3 atm, >2.4 atm, >2.5 atm, >2.6 atm, >2.7 atm, >2.8 atm, >2.9 atm, >3.0 atm, >3.5 atm, >4.0 atm, >4.5 atm, >5.0 atm, >5.5 atm, >6.0 atm, >6.5 atm, >7.0 atm, >7.5 atm, >8.0 atm, >8.5 atm, >9.0 atm, >10.0 atm, >11.0 atm, >12.0 atm, >13.0 atm, >14.0 atm, >15.0 atm, >16.0 atm, >17.0 atm, >18.0 atm, >19.0 atm or >20.0 atm.

In certain other embodiments, the total reaction pressure in an OCM reaction catalyzed by the catalysts ranges from about 1 atm to about 10 atm, from about 1 atm to about 7 atm, from about 1 atm to about 5 atm, from about 1 atm to about 3 atm or from about 1 atm to about 2 atm.

In some embodiments, the methane partial pressure in an OCM reaction catalyzed by the catalytic materials is >0.3 atm, >0.4 atm, >0.5 atm, >0.6 atm, >0.7 atm, >0.8 atm, >0.9 atm, >1 atm, >1.1 atm, >1.2 atm, >1.3 atm, >1.4 atm, >1.5 atm, >1.6 atm, >1.7 atm, >1.8 atm, >1.9 atm, >2.0 atm, >2.1 atm, >2.2 atm, >2.3 atm, >2.4 atm, >2.5 atm, >2.6 atm, >2.7 atm, >2.8 atm, >2.9 atm, >3.0 atm, >3.5 atm, >4.0 atm, >4.5 atm, >5.0 atm, >5.5 atm, >6.0 atm, >6.5 atm, >7.0 atm, >7.5 atm, >8.0 atm, >8.5 atm, >9.0 atm, >10.0 atm, >11.0 atm, >12.0 atm, >13.0 atm, >14.0 atm, >15.0 atm, >16.0 atm, >17.0 atm, >18.0 atm, >19.0 atm or >20.0 atm.

In some embodiments, the GSHV in an OCM reaction catalyzed by the catalytic materials is >10,000/hr, >15,000/hr, >20,000/hr, >50,000/hr, >75,000/hr, >100,000/hr, >120,000/hr, >130,000/hr, >150,000/hr, >200,000/hr, >250,000/hr, >300,000/hr, >350,000/hr, >400,000/hr, >450,000/hr, >500,000/hr, >750,000/hr, >1,000,000/hr, >2,000,000/hr, >3,000,000/hr, >4,000,000/hr.

The present inventors have discovered that OCM reactions catalyzed by the disclosed catalytic materials can be performed (and still maintain high C2 yield, C2 selectivity, conversion, etc.) using $O_2$ sources other than pure $O_2$. For example, in some embodiments the $O_2$ source in an OCM reaction catalyzed by the disclosed catalytic materials is air, oxygen enriched air, pure oxygen, oxygen diluted with nitrogen (or another inert gas) or oxygen diluted with $CO_2$. In certain embodiments, the $O_2$ source is $O_2$ diluted by >99%, >98%, >97%, >96%, >95%, >94%, >93%, >92%, >91%, >90%, >85%, >80%, >75%, >70%, >65%, >60%, >55%, >50%, >45%, >40%, >35%, >30%, >25%, >20%, >15%, >10%, >9%, >8%, >7%, >6%, >5%, >4%, >3%, >2% or >1% with $CO_2$ or an inert gas, for example nitrogen.

The disclosed catalytic materials are also very stable under conditions required to perform any number of catalytic reactions, for example the OCM reaction. The stability of the catalytic materials is defined as the length of time a catalyst will maintain its catalytic performance without a significant decrease in performance (e.g., a decrease >20%, >15%, >10%, >5%, or greater than 1% in C2 yield, C2 selectivity or conversion, etc.). In some embodiments, the catalytic materials have stability under conditions required for the OCM reaction of >1 hr, >5 hrs, >10 hrs, >20 hrs, >50 hrs, >80 hrs, >90 hrs, >100 hrs, >150 hrs, >200 hrs, >250 hrs, >300 hrs, >350 hrs, >400 hrs, >450 hrs, >500 hrs, >550 hrs, >600 hrs, >650 hrs, >700 hrs, >750 hrs, >800 hrs, >850 hrs, >900 hrs, >950 hrs, >1,000 hrs, >2,000 hrs, >3,000 hrs, >4,000 hrs, >5,000 hrs, >6,000 hrs, >7,000 hrs, >8,000 hrs, >9,000 hrs, >10,000 hrs, >11,000 hrs, >12,000 hrs, >13,000 hrs, >14,000 hrs, >15,000 hrs, >16,000 hrs, >17,000 hrs, >18,000 hrs, >19,000 hrs, >20,000 hrs, >1 yrs, >2 yrs, >3 yrs, >4 yrs or >5 yrs.

In some embodiments, the ratio of ethylene to ethane in an OCM reaction catalyzed by the catalytic materials is >0.3, >0.4, >0.5, >0.6, >0.7, >0.8, >0.9, >1, >1.1, >1.2, >1.3, >1.4, >1.5, >1.6, >1.7, >1.8, >1.9, >2.0, >2.1, >2.2, >2.3, >2.4, >2.5, >2.6, >2.7, >2.8, >2.9, >3.0, >3.5, >4.0, >4.5, >5.0, >5.5, >6.0, >6.5, >7.0, >7.5, >8.0, >8.5, >9.0, >9.5, >10.0.

In other embodiments, the conversion of methane in an OCM reaction catalyzed by the catalytic materials is greater than 10%, greater than 20%, greater than 30%, greater than 50%, greater than 75%, or greater than 90%. In other embodiments, the conversion of methane to ethylene in an OCM reaction catalyzed by the catalytic materials is greater than 10%, greater than 20%, greater than 30%, greater than 50%, greater than 75%, or greater than 90%. In some other embodiments the yield of ethylene in an OCM reaction catalyzed by the catalytic materials is greater than 10%, greater than 20%, greater than 30%, greater than 50%, greater than 75%, or greater than 90%. In some other embodiments the C2 yield in an OCM reaction catalyzed by the catalytic materials is greater than 10%, greater than 20%, greater than 30%, greater than 50%, greater than 75%, or greater than 90%.

In some other embodiments, a method for converting methane into ethane and/or ethylene comprising use of catalytic material comprising two or more catalysts is provided. For example, the catalyst mixture may be a mixture of a catalyst having good OCM activity and a catalyst having good ODH activity. Such catalyst mixtures are described in more detail above.

Typically, the OCM reaction is run in a mixture of oxygen and nitrogen or other inert gas. Such gasses are expensive and increase the overall production costs associated with preparation of ethylene or ethane from methane. However, the present inventors have now discovered that such expensive gases are not required and high yield, conversion, selectivity, etc. can be obtained when air is used as the gas mixture instead of pre-packaged and purified sources of oxygen and other gases. Accordingly, in one embodiment the disclosure provides a method for performing the OCM reaction in air by contacting the disclosed catalytic materials with methane and air.

In addition to air or $O_2$ gas, the presently disclosed catalytic materials and associated methods provide for use of other sources of oxygen in the OCM reaction. In this respect, an alternate source of oxygen such a $CO_2$, $H_2O$, $SO_2$ or $SO_3$ may be used either in place of, or in addition to, air or oxygen as the oxygen source. Such methods have the potential to increase the efficiency of the OCM reaction, for example by consuming a reaction byproduct (e.g., $CO_2$ or $H_2O$) and controlling the OCM exotherm as described below.

As noted above, in the OCM reaction, methane is oxidatively converted to methyl radicals, which are then coupled to form ethane, which is subsequently oxidized to ethylene. In traditional OCM reactions, the oxidation agent for both the methyl radical formation and the ethane oxidation to ethylene is oxygen. In order to minimize full oxidation of methane or ethane to carbon dioxide, i.e. maximize C2 selectivity, the methane to oxygen ratio is generally kept at 4 (i.e., full conversion of methane into methyl radicals) or above. As a result, the OCM reaction is typically oxygen limited and thus the oxygen concentration in the effluent is zero.

Accordingly, in one embodiment the present disclosure provides a method for increasing the methane conversion and increasing, or in some embodiments, not reducing, the C2 selectivity in an OCM reaction. The disclosed methods include performing the OCM reaction with a catalytic material comprising a traditional OCM catalyst and another OCM catalyst that uses an oxygen source other than molecular oxygen. In some embodiments, the alternate oxygen source is $CO_2$, $H_2O$, $SO_2$, $SO_3$ or combinations thereof. For example in some embodiments, the alternate oxygen source is $CO_2$. In other embodiments the alternate oxygen source is $H_2O$.

Because C2 selectivity is typically between 50% and 80% in the OCM reaction, OCM typically produces significant amounts of $CO_2$ as a byproduct ($CO_2$ selectivity can typically range from 20-50%). Additionally, $H_2O$ is produced in copious amounts, regardless of the C2 selectivity. Therefore both $CO_2$ and $H_2O$ are attractive oxygen sources for OCM in an $O_2$ depleted environment.

Accordingly, one embodiment of the present disclosure provides a catalytic material which is catalytic in the OCM reaction and which uses $CO_2$, $H_2O$, $SO_2$, $SO_3$ or another alternative oxygen source or combinations thereof as a source of oxygen. Other embodiments, provide a catalytic material comprising two or more catalysts, wherein the catalytic material comprises at least one catalyst which is catalytic in the OCM reaction and uses $O_2$ for at least one oxygen source and at least one catalysts which is catalytic in the OCM reaction and uses at least of $CO_2$, $H_2O$, $SO_2$, $SO_3$, NO, $NO_2$, $NO_3$ or another alternative oxygen source. Methods for performing the OCM reaction with such catalytic materials are also provided. Such methods include using an alternative oxygen source at temperatures of 900° C. or lower, 850° C. or lower, 800° C. or lower, 750° C. or lower, 700° C. or lower or even 650° C. or lower. In some embodiments of the above, the catalyst is a nanowire catalyst.

Examples of OCM catalysts that use $CO_2$ or other oxygen sources rather than $O_2$ include, but are not limited to, catalysts comprising $La_2O_3$/ZnO, $CeO_2$/ZnO, CaO/ZnO, $CaO/CeO_2$, $CaO/Cr_2O_3$, $CaO/MnO_2$, SrO/ZnO, $SrO/CeO_2$, $SrO/Cr_2O_3$, $SrO/MnO_2$, $SrCO_3/MnO_2$, BaO/ZnO, $BaO/CeO_2$, $BaO/Cr_2O_3$, $BaO/MnO_2$, $CaO/MnO/CeO_2$, $Na_2WO_4$/Mn/$SiO_2$, $Pr_2O_3$, $Tb_2O_3$.

Some embodiments provide a method for performing OCM, wherein a mixture of an OCM catalyst which use $O_2$ as an oxygen source (referred to herein as an $O_2$-OCM catalyst) and an OCM catalyst which use $CO_2$ as an oxygen source (referred to herein as a $CO_2$-OCM catalyst) is employed as the catalytic material, for example in a catalyst bed. Such methods have certain advantages. For example, the $CO_2$-OCM reaction is endothermic and the $O_2$-OCM reaction is exothermic, and thus if the right mixture and/or arrangement of $CO_2$-OCM and $O_2$-OCM catalysts is used, the methods are particularly useful for controlling the exotherm of the OCM reaction. In some embodiments, the catalyst bed comprises a mixture of $O_2$-OCM catalyst and $CO_2$-OCM catalysts. The mixture may be in a ratio of 1:99 to 99:1. The two catalysts work synergistically as the $O_2$-OCM catalyst supplies the $CO_2$-OCM catalyst with the necessary carbon dioxide and the endothermic nature of the $C_2$-OCM reaction serves to control the exotherm of the overall reaction. Alternatively, the $CO_2$ source may be external to the reaction (e.g., fed in from a $CO_2$ tank, or other source) and/or the heat required for the $CO_2$-OCM reaction is supplied from an external source (e.g., heating the reactor).

Since the gas composition will tend to become enriched in $CO_2$ as it flows through the catalyst bed (i.e., as the OCM reaction proceeds, more $CO_2$ is produced), some embodiments of the present invention provide an OCM method wherein the catalyst bed comprises a gradient of catalysts or catalytic materials which changes from a high concentration of $O_2$-OCM catalysts at the front of the bed to a high concentration of $CO_2$-OCM catalysts at the end of the catalyst bed.

The $O_2$-OCM catalyst and $CO_2$-OCM catalyst may have the same or different compositions. For example, in some embodiments the $O_2$-OCM catalyst and $CO_2$-OCM catalyst have the same composition but different morphologies (e.g., nanowire, bent nanowire, bulk, etc.). In other embodiments the $O_2$-OCM and the $CO_2$-OCM catalyst have different compositions.

Furthermore, $CO_2$-OCM catalysts will typically have higher selectivity, but lower yields than an $O_2$-OCM catalyst. Accordingly, in one embodiment the methods comprise use of catalytic material comprising a mixture of an $O_2$-OCM catalyst and a $CO_2$-OCM catalyst and performing the reaction in $O_2$ deprived environment so that the $CO_2$-OCM reaction is favored and the selectivity is increased. Under appropriate conditions the yield and selectivity of the OCM reaction can thus be optimized.

In some other embodiments, the catalyst bed comprises a mixture of one or more low temperature $O_2$-OCM catalyst (i.e., a catalyst active at low temperatures, for example less than 700° C.) and one or more high temperature $CO_2$-OCM catalyst (i.e., a catalyst active at high temperatures, for example 800° C. or higher). Here, the required high temperature for the $CO_2$-OCM may be provided by the hotspots produced by the $O_2$-OCM catalyst. In such a scenario, the mixture may be sufficiently coarse such that the hotspots are not being excessively cooled down by excessive dilution effect.

In other embodiments, the catalyst bed comprises alternating layers of $O_2$-OCM and $CO_2$-OCM catalysts. The catalyst layer stack may begin with a layer of $O_2$-OCM catalyst, so that it can supply the next layer (e.g., a $CO_2$-OCM layer) with the necessary $CO_2$. The $O_2$-OCM layer thickness may be optimized to be the smallest at which 02 conversion is 100% and thus the $CH_4$ conversion of the layer is maximized. The catalyst bed may comprise any number of catalyst layers, for example the overall number of layers may be optimized to maximize the overall $CH_4$ conversion and C2 selectivity.

In some embodiments, the catalyst bed comprises alternating layers of low temperature $O_2$-OCM catalysts and high temperature $CO_2$-OCM catalysts. Since the $CO_2$-OCM reaction is endothermic, the layers of $CO_2$-OCM catalyst may be sufficiently thin such that in can be "warmed up" by the hotspots of the $O_2$-OCM layers. The endothermic nature of the $CO_2$-OCM reaction can be advantageous for the overall thermal management of an OCM reactor. In some embodiments, the $CO_2$-OCM catalyst layers act as "internal" cooling for the $O_2$-OCM layers, thus simplifying the requirements for the cooling, for example in a tubular reactor. Therefore, an interesting cycle takes place with the endothermic reaction providing the necessary heat for the endothermic reaction and the endothermic reaction providing the necessary cooling for the exothermic reaction.

Accordingly, one embodiment of the present invention is a method for the oxidative coupling of methane, wherein the method comprises conversion of methane to ethane and/or ethylene in the presence of a catalytic material, and wherein the catalytic material comprises a bed of alternating layers of $O_2$-OCM catalysts and $CO_2$-OCM catalysts. In other embodiments the bed comprises a mixture (i.e., not alternating layers) of $O_2$-OCM catalysts and $CO_2$-OCM catalysts.

In other embodiments, the OCM methods include use of a jacketed reactor with the exothermic $O_2$-OCM reaction in the core and the endothermic $CO_2$-OCM reaction in the mantel. In other embodiments, the unused $CO_2$ can be recycled and reinjected into the reactor, optionally with the recycled $CH_4$. Additional $CO_2$ can also be injected to increase the overall methane conversion and help reduce greenhouse gases.

In other embodiments, the reactor comprises alternating stages of $O_2$-OCM catalyst beds and $CO_2$-OCM catalyst beds. The $CO_2$ necessary for the $CO_2$-OCM stages is provided by the $O_2$-OCM stage upstream. Additional $CO_2$ may also be injected. The $O_2$ necessary for the subsequent $O_2$-OCM stages is injected downstream from the $CO_2$-OCM stages. The $CO_2$-OCM stages may provide the necessary cooling for the $O_2$-OCM stages. Alternatively, separate cooling may be provided. Likewise, if necessary the inlet gas of the $CO_2$-OCM stages can be additionally heated, the $CO_2$-OCM bed can be heated or both.

In related embodiments, the $CO_2$ naturally occurring in natural gas is not removed prior to performing the OCM, alternatively CO2 is added to the feed with the recycled methane. Instead the $CO_2$ containing natural gas is used as a feedstock for $CO_2$-OCM, thus potentially saving a separation step. The amount of naturally occurring $CO_2$ in natural gas depends on the well and the methods can be adjusted accordingly depending on the source of the natural gas.

The foregoing methods can be generalized as a method to control the temperature of very exothermic reactions by coupling them with an endothermic reaction that uses the same feedstock (or byproducts of the exothermic reaction) to make the same product (or a related product). This concept can be reversed, i.e. providing heat to an endothermic reaction by coupling it with an exothermic reaction. This will also allow a higher per pass yield in the OCM reactor.

For purpose of simplicity, the above description relating to the use of $O_2$-OCM and $CO_2$-OCM catalysts was described in reference to the oxidative coupling of methane (OCM); however, the same concept is applicable to other catalytic reactions including but not limited to: oxidative dehydrogenation (ODH) of alkanes to their corresponding alkenes, selective oxidation of alkanes and alkenes and alkynes, etc. For example, in a related embodiment, a catalyst capable of using an alternative oxygen source (e.g., $CO_2$, $H_2O$, $SO_2$, $SO_3$ or combinations thereof) to catalyze the oxidative dehydrogenation of ethane is provided. Such catalysts, and uses thereof are described in more detail below.

Furthermore, the above methods are applicable for creating novel catalytic materials by blending catalysts that use different reactants for the same catalytic reactions, for example different oxidants for an oxidation reaction and at least one oxidant is a byproduct of one of the catalytic reactions. In addition, the methods can also be generalized for internal temperature control of reactors by blending catalysts that catalyze reactions that share the same or similar products but are exothermic and endothermic, respectively. These two concepts can also be coupled together.

2. Oxidative Dehydrogenation

Worldwide demand for alkenes, especially ethylene and propylene, is high. The main sources for alkenes include steam cracking, fluid-catalytic-cracking and catalytic dehydrogenation. The current industrial processes for producing alkenes, including ethylene and propylene, suffer from some of the same disadvantages described above for the OCM reaction. Accordingly, a process for the preparation of alkenes, which is more energy efficient and has higher yield, selectivity, and conversion than current processes is needed. Applicants have now found that the presently disclosed catalytic materials fulfill this need and provide related advantages.

In one embodiment, the catalytic materials are useful for catalyzing the oxidative dehydrogenation (ODH) of hydrocarbons (e.g. alkanes, alkenes, and alkynes). For example, in one embodiment the catalytic materials are useful for catalysis of an ODH reaction for the conversion of ethane or propane to ethylene or propylene, respectively. Reaction scheme (9) depicts the oxidative dehydrogenation of hydrocarbons:

$$C_xH_y + \tfrac{1}{2}O_2 \rightarrow C_xH_{y-2} + H_2O \qquad (9)$$

Representative catalysts useful for the ODH reaction include, but are not limited to catalysts (e.g., nanowires) comprising Zr, V, Mo, Ba, Nd, Ce, Ti, Mg, Nb, La, Sr, Sm, Cr, W, Y or Ca or oxides or combinations thereof. Activating promoters (i.e. dopants) comprising P, K, Ca, Ni, Cr, Nb, Mg, Au, Zn, or Mo, or combinations thereof, may also be employed.

In some embodiments, the conversion of hydrocarbon to alkene in an ODH reaction catalyzed by the catalytic materials is greater than 10%, greater than 20%, greater than 30%, greater than 50%, greater than 75%, or greater than 90%. In some other embodiments the yield of alkene in an ODH reaction catalyzed by the catalytic materials is greater than 10%, greater than 20%, greater than 30%, greater than 50%, greater than 75%, or greater than 90%. In other embodiments, the selectivity for alkenes in an ODH reaction catalyzed by the catalytic materials is greater than 50%, greater than 60%, greater than 70%, greater than 80%, greater than 90%, or greater than 95%. In another embodiment, the catalytic materials disclosed herein enable efficient conversion (i.e. high yield, conversion, and/or selectivity) of hydrocarbon to alkene at temperatures of less than 800° C., less than 700° C., less than 600° C., less than 500° C., less than 400° C., or less than 300° C.

The stability of the catalytic materials is defined as the length of time the catalytic materials will maintain its catalytic performance without a significant decrease in performance (e.g., a decrease >20%, >15%, >10%, >5%, or greater than 1% in ODH activity or alkene selectivity, etc.). In some embodiments, the catalytic materials have stability under conditions required for the ODH reaction of >1 hr, >5 hrs, >10 hrs, >20 hrs, >50 hrs, >80 hrs, >90 hrs, >100 hrs, >150 hrs, >200 hrs, >250 hrs, >300 hrs, >350 hrs, >400 hrs, >450 hrs, >500 hrs, >550 hrs, >600 hrs, >650 hrs, >700 hrs, >750 hrs, >800 hrs, >850 hrs, >900 hrs, >950 hrs, >1,000 hrs, >2,000 hrs, >3,000 hrs, >4,000 hrs, >5,000 hrs, >6,000 hrs, >7,000 hrs, >8,000 hrs, >9,000 hrs, >10,000 hrs, >11, 000 hrs, >12,000 hrs, >13,000 hrs, >14,000 hrs, >15,000 hrs, >16,000 hrs, >17,000 hrs, >18,000 hrs, >19,000 hrs, >20, 000 hrs, >1 yrs, >2 yrs, >3 yrs, >4 yrs or >5 yrs.

One embodiment of the present disclosure is directed to catalytic materials capable of using an alternative oxygen source (e.g., $CO_2$, $H_2O$, $SO_2$, $SO_3$ or combinations thereof) to catalyze the oxidative dehydrogenation of ethane is provided. For example, the ODH reaction may proceed according to the following reaction (10):

$$CO_2 + C_xH_y \rightarrow C_xH_{y-2} + CO + H_2O \quad (10)$$

wherein x is an integer and Y is 2x+2. Non-limiting examples of catalytic materials useful in this regard include catalytic materials comprising catalysts which comprise $Fe_2O_3$, $Cr_2O_3$, $MnO_2$, $Ga_2O_3$, $Cr/SiO_2$, $Cr/SO_4$—$SiO_2$, Cr—$K/SO_4$—$SiO_2$, $Na_2WO_4$—$Mn/SiO_2$, Cr-HZSM-5, Cr/Si-MCM-41 (Cr-HZSM-5 and Cr/Si-MCM-41 refer to known zeolites) and/or $MoC/SiO_2$. In some embodiments, any of the foregoing catalytic materials may comprise $SiO_2$, $ZrO_2$, $Al_2O_3$, $TiO_2$ or combinations thereof. In certain embodiments, the catalyst may be a nanowire catalyst and in other embodiments the catalyst is a bulk catalyst.

The catalytic materials having ODH activity with alternative oxygen sources (e.g., $CO_2$, referred to herein as a $CO_2$-ODH catalyst) have a number of advantages. For example, in some embodiments a method for converting methane to ethylene comprising use of catalytic materials comprising at least one $O_2$-OCM catalyst and at least one $CO_2$-ODH catalyst are also provided. This combination of catalysts results in a higher yield of ethylene (and/or ratio of ethylene to ethane) since the $CO_2$ produced by the OCM reaction is consumed and used to convert ethane to ethylene.

In one embodiment, a method for preparation of ethylene comprises converting methane to ethylene in the presence of a catalytic material comprising at least one catalyst which is an $O_2$-OCM catalyst and at least one catalyst which is a $CO_2$-ODH catalyst. Such methods have certain advantages. For example, the $CO_2$-ODH reaction is endothermic and the $O_2$-OCM reaction is exothermic, and thus if the right mixture and/or arrangement of $CO_2$-ODH and $O_2$-OCM catalysts is used, the methods are particularly useful for controlling the exotherm of the OCM reaction. In some embodiments, the catalyst bed comprises a mixture of $O_2$-OCM catalyst and $CO_2$-ODH catalysts. The mixture may be in a ratio of 1:99 to 99:1. The two catalysts work synergistically as the $O_2$-OCM catalyst supplies the $CO_2$-ODH catalyst with the necessary carbon dioxide and the endothermic nature of the $C_2$-OCM reaction serves to control the exotherm of the overall reaction.

Since the gas composition will tend to become enriched in $CO_2$ as it flows through the catalyst bed (i.e., as the OCM reaction proceeds, more $CO_2$ is produced), some embodiments of the present invention provide an OCM method wherein the catalyst bed comprises a gradient of catalysts which changes from a high concentration of $O_2$-OCM catalysts at the front of the bed to a high concentration of $CO_2$-ODH catalysts at the end of the catalyst bed.

The $O_2$-ODH catalyst and $CO_2$-ODH catalyst may have the same or different compositions. For example, in some embodiments the $O_2$-ODH catalyst and $CO_2$-ODH catalyst have the same composition but different morphologies (e.g., nanowire, bent nanowire, bulk, etc.). In other embodiments the $O_2$-ODH and the $CO_2$-ODH catalyst have different compositions.

In other embodiments, the catalyst bed comprises alternating layers of $O_2$-OCM and $CO_2$-ODH catalysts. The catalyst layer stack may begin with a layer of $O_2$-OCM catalyst, so that it can supply the next layer (e.g., a CO2-ODH layer) with the necessary $CO_2$. The $O_2$-OCM layer thickness may be optimized to be the smallest at which O2 conversion is 100% and thus the $CH_4$ conversion of the layer is maximized. The catalyst bed may comprise any number of catalyst layers, for example the overall number of layers may be optimized to maximize the overall $CH_4$ conversion and C2 selectivity.

In some embodiments, the catalyst bed comprises alternating layers of low temperature $O_2$-OCM catalysts and high temperature $CO_2$-ODH catalysts. Since the $CO_2$-ODH reaction is endothermic, the layers of $CO_2$-ODH catalyst may be sufficiently thin such that in can be "warmed up" by the hotspots of the $O_2$-OCM layers. The endothermic nature of the $CO_2$-ODH reaction can be advantageous for the overall thermal management of an OCM reactor. In some embodiments, the $CO_2$-ODH catalyst layers act as "internal" cooling for the $O_2$-OCM layers, thus simplifying the requirements for the cooling, for example in a tubular reactor. Therefore, an interesting cycle takes place with the endothermic reaction providing the necessary heat for the endothermic reaction and the endothermic reaction providing the necessary cooling for the exothermic reaction.

Accordingly, one embodiment of the present invention is a method for the oxidative coupling of methane, wherein the method comprises conversion of methane to ethane and/or ethylene in the presence of a catalytic material, and wherein the catalytic material comprises a bed of alternating layers of $O_2$-OCM catalysts and $CO_2$-ODH catalysts. In other embodiments the bed comprises a mixture (i.e., not alternating layers) of $O_2$-OCM catalysts and $CO_2$-ODH catalysts. Such methods increase the ethylene yield and/or ratio of ethylene to ethane compared to other known methods.

In other embodiments, the OCM methods include use of a jacketed reactor with the exothermic $O_2$-OCM reaction in the core and the endothermic $CO_2$-ODH reaction in the mantel. In other embodiments, the unused $CO_2$ can be recycled and reinjected into the reactor, optionally with the recycled $CH_4$. Additional $CO_2$ can also be injected to increase the overall methane conversion and help reduce greenhouse gases.

In other embodiments, the reactor comprises alternating stages of $O_2$-OCM catalyst beds and $CO_2$-ODH catalyst beds. The $CO_2$ necessary for the $CO_2$-ODH stages is provided by the $O_2$-OCM stage upstream. Additional $CO_2$ may also be injected. The $O_2$ necessary for the subsequent O2-OCM stages is injected downstream from the $CO_2$-ODH stages. The $CO_2$-ODH stages may provide the necessary cooling for the $O_2$-OCM stages. Alternatively, separate cooling may be provided. Likewise, if necessary the inlet gas of the $CO_2$-ODH stages can be additionally heated, the $CO_2$-ODH bed can be heated or both.

In related embodiments, the $CO_2$ naturally occurring in natural gas is not removed prior to performing the OCM, alternatively $CO_2$ is added to the feed with the recycled methane. Instead, the $CO_2$ containing natural gas is used as a feedstock for $CO_2$-ODH, thus potentially saving a separation step. The amount of naturally occurring $CO_2$ in natural gas depends on the well and the methods can be adjusted accordingly depending on the source of the natural gas.

3. Carbon Dioxide Reforming of Methane

Carbon dioxide reforming (CDR) of methane is an attractive process for converting $CO_2$ in process streams or naturally occurring sources into the valuable chemical product, syngas (a mixture of hydrogen and carbon monoxide). Syngas can then be manufactured into a wide range of hydrocarbon products through processes such as the Fischer-Tropsch synthesis (discussed below) to form liquid fuels including methanol, ethanol, diesel, and gasoline. The result is a powerful technique to not only remove $CO_2$ emissions but also create a new alternative source for fuels that are not derived from petroleum crude oil. The CDR reaction with methane is exemplified in reaction scheme (11).

$$CO_2 + CH_4 \rightarrow 2CO + 2H_2 \quad (11)$$

Unfortunately, no established industrial technology for CDR exists today in spite of its tremendous potential value. While not wishing to be bound by theory, it is thought that the primary problem with CDR is due to side-reactions from catalyst deactivation induced by carbon deposition via the Boudouard reaction (reaction scheme (12)) and/or methane cracking (reaction scheme (13)) resulting from the high temperature reaction conditions. The occurrence of the coking effect is intimately related to the complex reaction mechanism, and the associated reaction kinetics of the catalysts employed in the reaction.

$$2CO \rightarrow C + CO_2 \quad (12)$$

$$CH_4 \rightarrow C + 2H_2 \quad (13)$$

Figure 3:
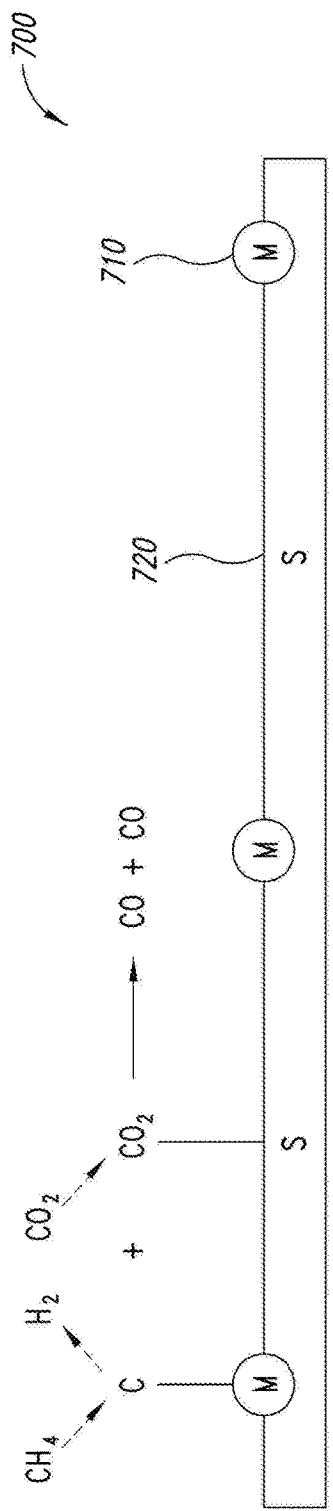
FIG. 3 schematically depicts the carbon dioxide reforming (CDR) of methane reaction.

While not wishing to be bound by theory, the CDR reaction is thought to proceed through a multistep surface reaction mechanism. FIG. 3 schematically depicts a CDR reaction 700, in which activation and dissociation of $CH_4$ occurs on the metal catalyst surface 710 to form intermediate "M-C". At the same time, absorption and activation of $CO_2$ takes place at the oxide support surface 720 to provide intermediate "S—$CO_2$", since the carbon in a $CO_2$ molecule as a Lewis acid tends to react with the Lewis base center of an oxide. The final step is the reaction between the M-C species and the activated S—$CO_2$ to form CO.

In one embodiment, the present disclosure provides catalytic materials which are useful as catalysts for the carbon dioxide reforming of methane. For example, in one embodiment the catalytic materials are useful as catalysts in a CDR reaction for the production of syn gas.

In some embodiments, the conversion of $CO_2$ to CO in a CDR reaction catalyzed by the catalytic materials is greater than 10%, greater than 20%, greater than 30%, greater than 50%, greater than 75%, or greater than 90%. In some embodiments the yield of CO in a CDR reaction catalyzed by the catalytic materials is greater than 10%, greater than 20%, greater than 30%, greater than 50%, greater than 75%, or greater than 90%. In other embodiments, the selectivity for CO in a CDR reaction catalyzed by the catalytic materials is greater than 10%, greater than 20%, greater than 30%, greater than 50%, greater than 75%, or greater than 90%. In other embodiments, the catalytic materials enable efficient conversion (i.e., high yield, conversion, and/or selectivity) of $CO_2$ to CO at temperatures of less than 900° C., less than 800° C., less than 700° C., less than 600° C., or less than 500° C.

4. Fischer-Tropsch Synthesis

Fischer-Tropsch synthesis (FTS) is a valuable process for converting synthesis gas (i.e., CO and $H_2$) into valuable hydrocarbon fuels, for example, light alkenes, gasoline, diesel fuel, etc. FTS has the potential to reduce the current reliance on the petroleum reserve and take advantage of the abundance of coal and natural gas reserves. Current FTS processes suffer from poor yield, selectivity, conversion, catalyst deactivation, poor thermal efficiency and other related disadvantages. Production of alkanes via FTS is shown in reaction scheme (14), wherein n is an integer.

$$CO + 2H_2 \rightarrow (1/n)(C_nH_{2n}) + H_2O \quad (14)$$

In one embodiment, catalytic materials are provided which are useful in FTS processes. For example, in one embodiment the catalytic materials are used in a FTS process for the production of alkanes.

In some embodiments, the conversion of CO to alkane in an FTS process catalyzed by the catalytic materials is greater than 10%, greater than 20%, greater than 30%, greater than 50%, greater than 75%, or greater than 90%. In some embodiments the yield of alkane in an FTS process catalyzed by the catalytic materials is greater than 10%, greater than 20%, greater than 30%, greater than 50%, greater than 75%, or greater than 90%. In other embodiments, the selectivity for alkanes in an FTS process catalyzed by the catalytic materials is greater than 10%, greater than 20%, greater than 30%, greater than 50%, greater than 75%, or greater than 90%. In still other embodiments, the nanowires enable efficient conversion (i.e., high yield, conversion, and/or selectivity) of CO to alkanes at temperatures of less than 400° C., less than 300° C., less than 250° C., less than 200° C., less the 150° C., less than 100° C. or less than 50° C.

5. Oxidation of CO

Carbon monoxide (CO) is a toxic gas and can convert hemoglobin to carboxyhemoglobin resulting in asphyxiation. Dangerous levels of CO can be reduced by oxidation of CO to $CO_2$ as shown in reaction scheme 15:

$$CO + \tfrac{1}{2}O_2 \rightarrow CO_2 \quad (15)$$

Catalysts for the conversion of CO into $CO_2$ have been developed but improvements to the known catalysts are needed. Accordingly in one embodiment, the present disclosure provides catalytic materials useful for the oxidation of CO to $CO_2$.

In some embodiments, the conversion of CO to $CO_2$ catalyzed by the catalytic materials is greater than 10%, greater than 20%, greater than 30%, greater than 50%, greater than 75%, or greater than 90%. In other embodiments the yield of $CO_2$ from the oxidation of CO catalyzed by the catalytic materials is greater than 10%, greater than 20%, greater than 30%, greater than 50%, greater than 75%, or greater than 90%. In still other embodiments, the selectivity for $CO_2$ in the oxidation of CO catalyzed by the catalytic materials is greater than 10%, greater than 20%, greater than 30%, greater than 50%, greater than 75%, or greater than 90%. In yet other embodiments, the nanowires enable efficient conversion (i.e., high yield, conversion, and/or selectivity) of CO to $CO_2$ at temperatures of less than 500° C., less than 400° C., less than 300° C., less than 200° C., less than 100° C., less than 50° C. or less than 20° C.

6. Combustion of Hydrocarbons

In another embodiment, the present disclosure provides catalytic materials for the catalyzed combustion of hydrocarbons. Such catalytic reactions find utility in any number of applications, including catalytic converters for automobiles by removal of unburned hydrocarbons in the exhaust by catalytic combustion or oxidation of soot captured on catalyzed particle filters resulting in reduction on diesel emissions from the engine. When running "cold", the exhausts temperature of a diesel engine is quite low, thus a low temperature catalyst is needed to efficiently eliminate all unburned hydrocarbons. In addition, in case of soot removal on catalyzed particulate filters, intimate contact between the soot and the catalyst is require; the disclosed catalytic materials provide these and other related advantages for the catalyzed combustion of hydrocarbons.

In some embodiments, the total combustion of hydrocarbons catalyzed by the catalytic materials is greater than 10%, greater than 20%, greater than 30%, greater than 50%, greater than 75%, or greater than 90%. In some other embodiments the yield of combusted hydrocarbon products in a reaction catalyzed by the catalytic materials is greater than 10%, greater than 20%, greater than 30%, greater than 50%, greater than 75%, or greater than 90%.

The stability of the catalytic materials is defined as the length of time a catalytic material will maintain its catalytic performance without a significant decrease in performance (e.g., a decrease >20%, >15%, >10%, >5%, or greater than 1% in hydrocarbon or soot combustion activity). In some embodiments, the catalytic materials have stability under conditions required for the hydrocarbon combustion reaction of >1 hr, >5 hrs, >10 hrs, >20 hrs, >50 hrs, >80 hrs, >90 hrs, >100 hrs, >150 hrs, >200 hrs, >250 hrs, >300 hrs, >350 hrs, >400 hrs, >450 hrs, >500 hrs, >550 hrs, >600 hrs, >650 hrs, >700 hrs, >750 hrs, >800 hrs, >850 hrs, >900 hrs, >950 hrs, >1,000 hrs, >2,000 hrs, >3,000 hrs, >4,000 hrs, >5,000 hrs, >6,000 hrs, >7,000 hrs, >8,000 hrs, >9,000 hrs, >10,000 hrs, >11,000 hrs, >12,000 hrs, >13,000 hrs, >14,000 hrs, >15,000 hrs, >16,000 hrs, >17,000 hrs, >18,000 hrs, >19,000 hrs, >20,000 hrs, >1 yrs, >2 yrs, >3 yrs, >4 yrs or >5 yrs.

Although various reactions have been described in detail, the disclosed catalytic materials are useful as catalysts in a variety of other reactions. In general, the disclosed catalytic materials find utility in any reaction utilizing a heterogeneous catalyst and use of the catalytic materials is not limited to the specifically described reactions.

7. Evaluation of Catalytic Properties

To evaluate the catalytic properties of the catalytic materials in a given reaction, for example those reactions discussed above, various methods can be employed to collect and process data including measurements of the kinetics and amounts of reactants consumed and the products formed. In addition to allowing for the evaluation of the catalytic performances, the data can also aid in designing large scale reactors, experimentally validating models and optimizing the catalytic process.

Figure 4:
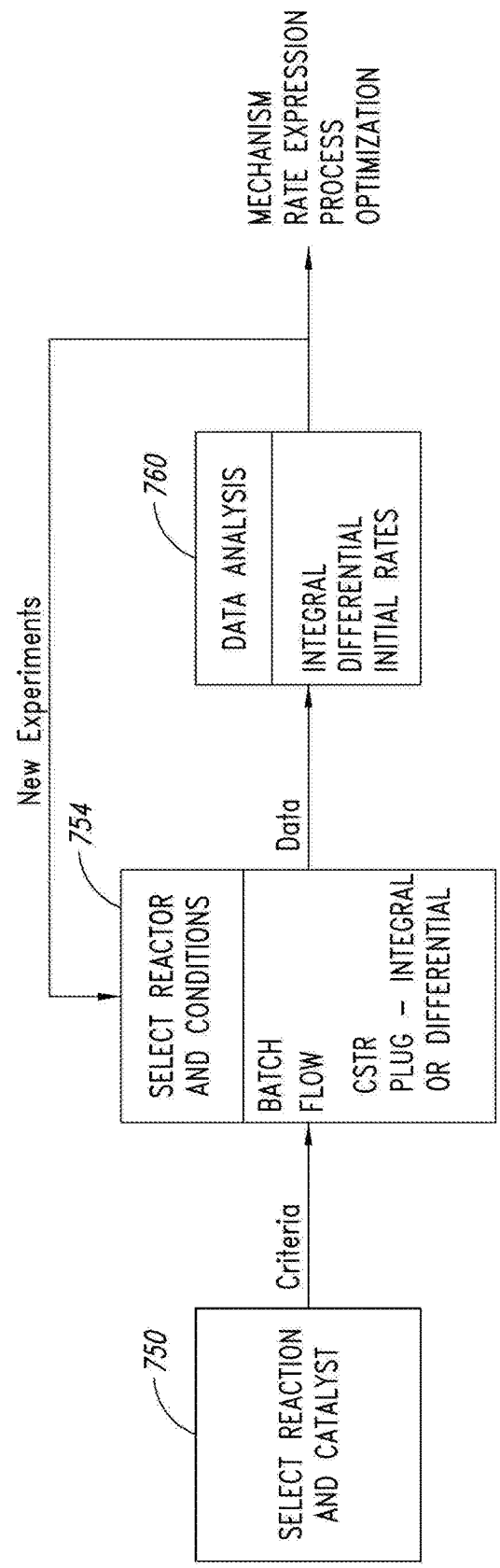
FIG. 4 illustrates an exemplary methodology for collecting and processing catalyst data.

One exemplary methodology for collecting and processing data is depicted in FIG. 4. Three main steps are involved. The first step (block 750) comprises the selection of a reaction and catalyst. This influences the choice of reactor and how it is operated, including batch, flow, etc. (block 754). Thereafter, the data of the reaction are compiled and analyzed (block 760) to provide insights to the mechanism, rates and process optimization of the catalytic reaction. In addition, the data provide useful feedbacks for further design modifications of the reaction conditions. Additional methods for evaluating catalytic performance in the laboratory and industrial settings are described in, for example, Bartholomew, C. H. et al. *Fundamentals of Industrial Catalytic Processes*, Wiley-AIChE; 2Ed (1998).

As an example, in a laboratory setting, an Altamira Benchcat 200 can be employed using a 4 mm ID diameter quartz tube with a 0.5 mm ID capillary downstream. Quartz tubes with 2 mm, 6 mm or 8 mm ID can also be used. Catalytic materials are tested under a number of different conditions.

In a typical procedure, 50 mg is the total charge of catalytic material. On either side of the catalytic materials, a small plug of glass wool is loaded to keep the catalytic materials in place. A thermocouple is placed on the inlet side of the catalytic materials bed into the glass wool to get the temperature in the reaction zone. Another thermocouple can be placed on the downstream end into the catalyst bed itself to measure the exotherms, if any.

Once loaded into the reactor, the reactor is inserted into the Altamira instrument and furnace and then a temperature and flow program is started. In some embodiments, the total flow is 50 to 100 sccm of gases but this can be varied and programmed with time. In one embodiment, the temperatures range from 450° C. to 900° C. The reactant gases comprise air or oxygen (diluted with nitrogen or argon) and methane in the case of the OCM reaction and gas mixtures comprising ethane and/or propane with oxygen for oxidative dehydrogenation (ODH) reactions. Other gas mixtures can be used for other reactions.

The primary analysis of these oxidation catalysis runs is the Gas Chromatography (GC) analysis of the feed and effluent gases. From these analyses, the conversion of the oxygen and alkane feed gases can easily be attained and estimates of yields and selectivities of the products and by-products can be determined.

The GC method developed for these experiments employs 4 columns and 2 detectors and a complex valve switching system to optimize the analysis. Specifically, a flame ionization detector (FID) is used for the analysis of the hydrocarbons only. It is a highly sensitive detector that produces accurate and repeatable analysis of methane, ethane, ethylene, propane, propylene and all other simple alkanes and alkenes up to five carbons in length and down to ppm levels.

There are two columns in series to perform this analysis, the first is a stripper column (alumina) which traps polar materials (including the water by-product and any oxygenates generated) until back-flushed later in the cycle. The second column associated with the FID is a capillary alumina column known as a PLOT column, which performs the actual separation of the light hydrocarbons. The water and oxygenates are not analyzed in this method.

For the analysis of the light non-hydrocarbon gases, a Thermal Conductivity Detector (TCD) may be employed which also employs two columns to accomplish its analysis. The target molecules for this analysis are $CO_2$, ethylene, ethane, hydrogen, oxygen, nitrogen, methane and CO. The two columns used here are a porous polymer column known as the Hayes Sep N, which performs some of the separation for the $CO_2$, ethylene and ethane. The second column is a molecular sieve column, which uses size differentiation to perform the separation. It is responsible for the separation of $H_2$, $O_2$, $N_2$, methane and CO.

There is a sophisticated and timing sensitive switching between these two columns in the method. In the first 2 minutes or so, the two columns are operating in series but at about 2 minutes, the molecular sieve column is by-passed and the separation of the first 3 components is completed. At about 5-7 minutes, the columns are then placed back in series and the light gases come off of the sieve according to their molecular size.

The end result is an accurate analysis of all of the aforementioned components from these fixed-bed, gas phase reactions. Analysis of other reactions and gases not specifically described above is performed in a similar manner.

8. Downstream Products

Figure 5:
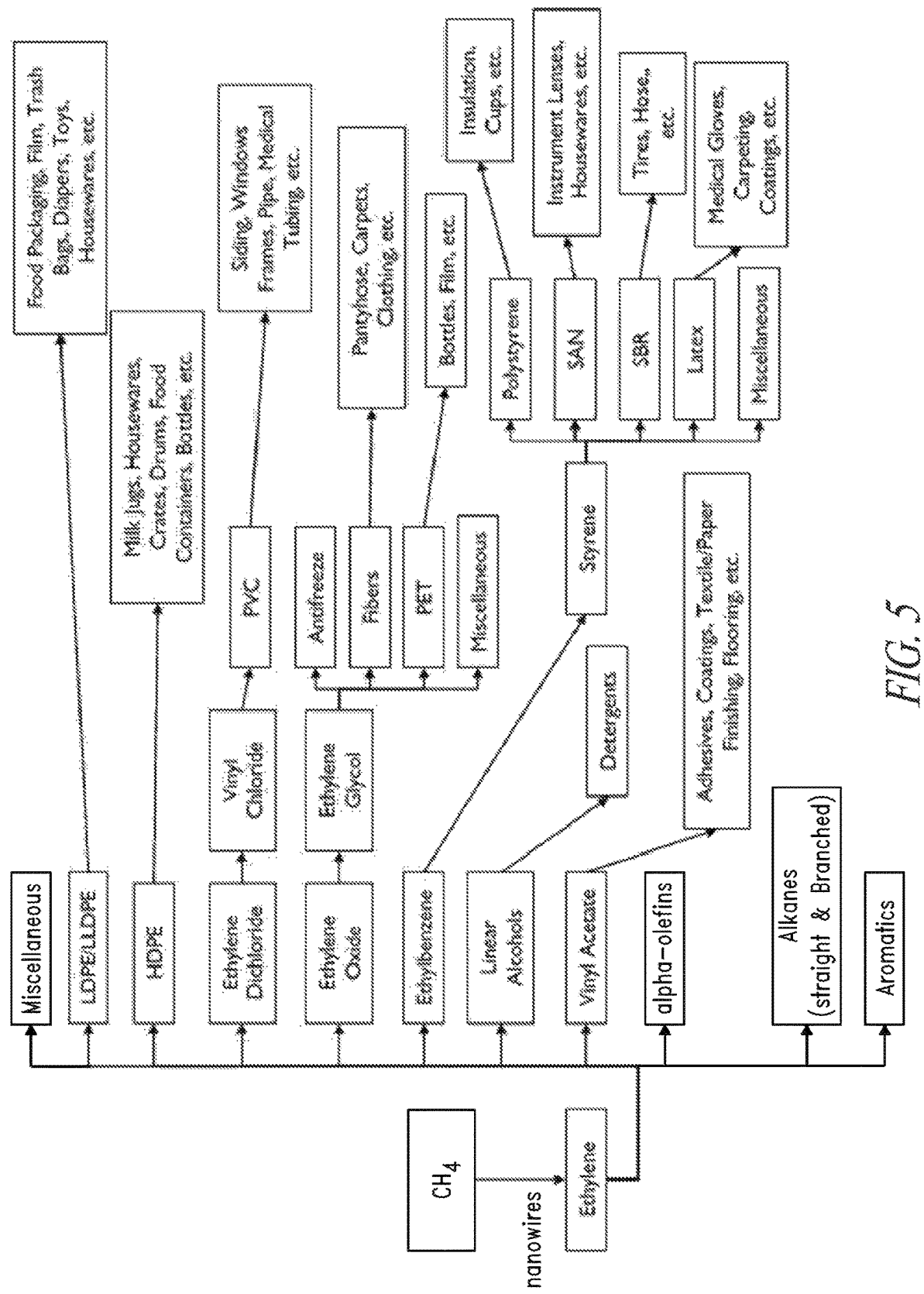
FIG. 5 shows representative downstream products of ethylene.

As noted above, in one embodiment the present disclosure is directed to catalytic materials useful in reactions for the preparation of a number of valuable hydrocarbon compounds. For example, in one embodiment the catalytic materials are useful for the preparation of ethylene from methane via the OCM reaction. In another embodiment, the catalytic materials are useful for the preparation of ethylene or propylene via oxidative dehydrogenation of ethane or propane, respectively. Ethylene and propylene are valuable compounds, which can be converted into a variety of consumer products. For example, as shown in FIG. 5, ethylene can be converted into many various compounds including low density polyethylene, high density polyethylene, ethylene dichloride, ethylene oxide, ethylbenzene, linear alcohols, vinyl acetate, alkanes, alpha olefins, various hydrocarbon-based fuels, ethanol and the like. These compounds can then be further processed using methods well known to one of ordinary skill in the art to obtain other valuable chemicals and consumer products (e.g. the downstream products shown in FIG. 5). Propylene can be analogously converted into various compounds and consumer goods including polypropylenes, propylene oxides, propanol, and the like.

Accordingly, in one embodiment the invention is directed to a method for the preparation of C2 hydrocarbons via the OCM reaction, the method comprises contacting a catalyst as described herein with a gas comprising methane. In some embodiments the C2 hydrocarbons are selected from ethane and ethylene. In other embodiments the disclosure provides a method of preparing downstream products of ethylene. The method comprises converting ethylene into a downstream product of ethylene, wherein the ethylene has been prepared via a catalytic reaction employing a catalyst disclosed herein (e.g., OCM). In some embodiments, the downstream product of ethylene is low density polyethylene, high density polyethylene, ethylene dichloride, ethylene oxide, ethylbenzene, ethanol or vinyl acetate. In other embodiments, the downstream product of ethylene is natural gasoline. In still other embodiments, the downstream product of ethylene comprises 1-hexene, 1-octene, hexane, octane, benzene, toluene, xylene or combinations thereof.

In another embodiment, a process for the preparation of ethylene from methane comprising contacting a mixture comprising oxygen and methane at a temperature below 900° C., below 850° C., below 800° C., below 750° C., below 700° C. or below 650° C. with a catalytic material as disclosed herein is provided.

In another embodiment, the disclosure provides a method of preparing a product comprising low density polyethylene, high density polyethylene, ethylene dichloride, ethylene oxide, ethylbenzene, ethanol or vinyl acetate, alkenes, alkanes, aromatics, alcohols, or mixtures thereof. The method comprises converting ethylene into low density polyethylene, high density polyethylene, ethylene dichloride, ethylene oxide, ethylbenzene, ethanol or vinyl acetate, wherein the ethylene has been prepared via a catalytic reaction employing the catalytic materials disclosed herein.

In more specific embodiments of any of the above methods, the ethylene is produced via an OCM or ODH reaction or combinations thereof.

In one particular embodiment, the disclosure provides a method of preparing a downstream product of ethylene and/or ethane. For example, the downstream product of ethylene may be a hydrocarbon fuel such as natural gasoline or a $C_4$-$C_{14}$ hydrocarbon, including alkanes, alkenes and aromatics. Some specific examples include 1-butene, 1-hexene, 1-octene, hexane, octane, benzene, toluene, xylenes and the like. The method comprises converting methane into ethylene, ethane or combinations thereof by use of a catalytic material disclosed herein, and further oligomerizing the ethylene and/or ethane to prepare a downstream product of ethylene and/or ethane. For example, the methane may be converted to ethylene, ethane or combinations thereof via the OCM reaction as discussed above. The catalytic materials may comprise any catalyst, and the catalyst is not limited with respect to morphology or composition. The catalyst may be an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof. Alternatively, the catalyst may be an inorganic nanowire comprising one or more metal elements from any of Groups 1 through 7, lanthanides, actinides or combinations thereof and a dopant comprising a metal element, a semi-metal element, a non-metal element or combinations thereof. In other embodiments, the catalytic materials comprise a bulk catalyst. The catalysts may additionally comprise any number of doping elements as discussed above.

Figure 6:
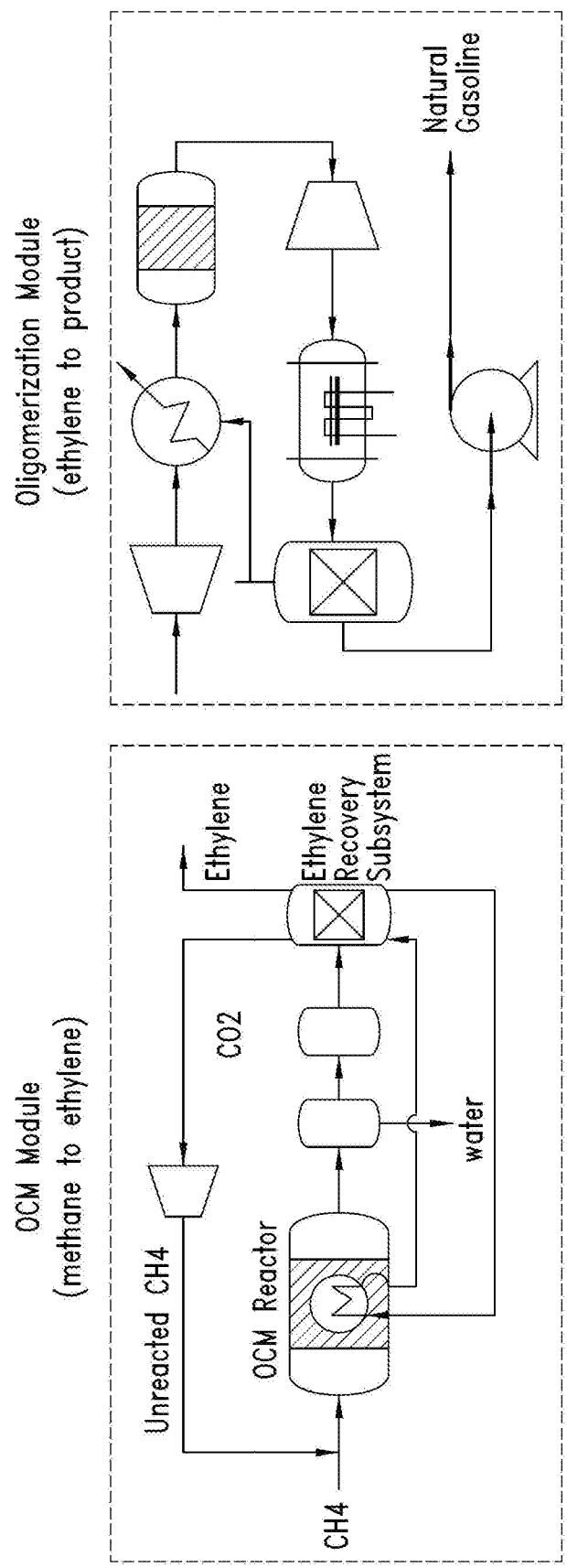
FIG. 6 is a flow chart showing preparation of ethylene-based products.

As depicted in FIG. 6, the method begins with charging methane (e.g., as a component in natural gas) into an OCM reactor. The OCM reaction may then be performed utilizing a catalytic material under any variety of conditions. Water and $CO_2$ are optionally removed from the effluent and unreacted methane is recirculated to the OCM reactor.

Ethylene is recovered and charged to an oligomerization reactor. Optionally the ethylene stream may contain $CO_2$, $H_2O$, $N_2$, ethane, C3's and/or higher hydrocarbons. Oligomerization to higher hydrocarbons (e.g., $C_4$-$C_{14}$) then proceeds under any number of conditions known to those of skill in the art. For example oligomerization may be effected by use of any number of catalysts known to those skilled in the art. Examples of such catalysts include catalytic zeolites, crystalline borosilicate molecular sieves, homogeneous metal halide catalysts, Cr catalysts with pyrrole ligands or other catalysts. Exemplary methods for the conversion of ethylene into higher hydrocarbon products are disclosed in the following references: Catalysis Science & Technology (2011), 1(1), 69-75; Coordination Chemistry Reviews (2011), 255(7-8), 861-880; Eur. Pat. Appl. (2011), EP 2287142 A1 20110223; Organometallics (2011), 30(5), 935-941; Designed Monomers and Polymers (2011), 14(1), 1-23; Journal of Organometallic Chemistry 689 (2004) 3641-3668; Chemistry—A European Journal (2010), 16(26), 7670-7676; Acc. Chem. Res. 2005, 38, 784-793; Journal of Organometallic Chemistry, 695 (10-11): 1541-1549 May 15 2010; Catalysis Today Volume 6, Issue 3, January 1990, Pages 329-349; U.S. Pat. Nos. 5,968,866; 6,800,702; 6,521,806; 7,829,749; 7,867,938; 7,910,670; 7,414,006 and Chem. Commun., 2002, 858-859, each of which are hereby incorporated in their entirety by reference.

In certain embodiments, the exemplary OCM and oligomerization modules depicted in FIG. 6 may be adapted to be at the site of natural gas production, for example a natural gas field. Thus the natural gas can be efficiently converted to more valuable and readily transportable hydrocarbon commodities without the need for transport of the natural gas to a processing facility.

Referring to FIG. 6, "natural gasoline" refers to a mixture of oligomerized ethylene products. In this regard, natural gasoline comprises hydrocarbons containing 5 or more carbon atoms. Exemplary components of natural gasoline include linear, branched or cyclic alkanes, alkenes and alkynes, as well as aromatic hydrocarbons. For example, in some embodiments the natural gasoline comprises 1-pentene, 1-hexene, cyclohexene, 1-octene, benzene, toluene, dimethyl benzene, xylenes, napthalene, or other oligomerized ethylene products or combinations thereof. In some embodiments, natural gasoline may also include C3 and C4 hydrocarbons dissolved within the liquid natural gasoline. This mixture finds particular utility in any number of industrial applications, for example natural gasoline is used as feedstock in oil refineries, as fuel blend stock by operators of fuel terminals, as diluents for heavy oils in oil pipelines and other applications. Other uses for natural gasoline are well-known to those of skill in the art.

EXAMPLES

Example 1

Preparation of Supported $MnWO_4$ Nanowire Catalysts

Supported $MnWO_4$ nanowire catalysts are prepared using the following general protocol. $MnWO_4$ nanowires are prepared using the method described in U.S. Pub. No. 2012/0041246. Manganese tungstate nanowires, support, and water are slurried for 6 h at room temperature. The manganese tungstate to support ratio ranges from 2-10 wt %. The mixture is dried in a 65° C. oven and then calcined in a muffle oven in air: load in the furnace at room temperature, ramp to 400° C. with 5° C./min rate, dwell for 2 h, ramp to 850° C. with 5° C./min rate, dwell for 8 h, cool to room temperature. The following is a list of exemplary supports that may be used: $SiO_2$, $Al_2O_3$, $SiO_2$—$Al_2O_3$, $ZrO_2$, $TiO_2$, $HfO_2$, Silica-Aluminum Phosphate, and Aluminum Phosphate.

Example 2

Preparation of Catalytic Material Comprising Cordierite Honeycomb Ceramic Supported $Nd_2O_3$ Nanowires $Nd_2O_3$ nanowires are prepared using the methods described in U.S. Pub. No. 2012/0041246.

A 400 mg aliquot of $Nd_2O_3$ nanowires is mixed with 2 g of DI water and placed into a 5 ml glass vial containing 2 mm Yttria Stabilized Zirconia milling balls. The vial is placed on a shaker at 2000 RPM and agitated for 30 minutes. A thick slurry is obtained.

A ⅜ inch diameter core is cut along the channel direction into a 400 CPSI (channel per square inch) cordierite honeycomb monolith and cut in length so the core volume is approximately 1 ml.

The core is placed into a ⅜ inch tube, and the catalyst slurry is fed on top of the ceramic core and pushed with compressed air through the monolith channel. The excess slurry is captured into a 20 ml vial. The coated core is removed from the ⅜ inch tube and placed into a drying oven at 200° C. for 1 hour.

The coating step is repeated two more times with the remaining slurry followed by drying at 200° C. and calcination at 500° C. for 4 hours. The catalyst amount deposited on the monolith channel walls is approximately 50 mg and comprises very good adhesion to the ceramic wall.

Example 3

Preparation of Catalytic Material Comprising Silicon Carbide Ceramic Foam Supported $Nd_2O_3$ Nanowires $Nd_2O_3$ nanowires were prepared using the methods described in U.S. Pub. No. 2012/0041246.

A 400 mg aliquot of $Nd_2O_3$ nanowires is mixed with 2 g of DI water and placed into a 5 ml glass vial containing 2 mm Yttria Stabilized Zirconia milling balls. The vial is placed on a shaker at 2000 RPM and agitated for 30 minutes. A thick slurry is obtained.

A ⅜ inch diameter core is cut from a 65 PPI (Pore Per Inch) SiC foam and cut in length so the core volume is approximately 1 ml.

The core is placed into a ⅜ inch tube and the catalyst slurry is fed on top of the ceramic core and pushed with compressed air through the monolith channel. The excess slurry is captured into a 20 ml vial. The coated core is removed from the ⅜ inch tube and placed into a drying oven at 200° C. for 1 hour.

The coating step is repeated two more times with the remaining slurry followed by drying at 200° C. and calcination at 500° C. for 4 hours. The catalyst amount deposited on the monolith channel walls is approximately 60 mg and comprises very good adhesion to the ceramic mesh.

Example 4

Preparation of Catalytic Material Comprising Silicon Carbide and $Nd_2O_3$ Nanowires $Nd_2O_3$ nanowires are prepared using the methods described in U.S. Pub. No. 2012/0041246.

A 400 mg aliquot of $Nd_2O_3$ nanowires is dry blend mixed with 400 mg of 200-250 mesh SiC particles for 10 minutes or until the mixture appears homogeneous and wire clusters are no longer visible. The mixture is then placed into a ¼ inch die and pressed in 200 mg batches. The pressed pellets are then placed into an oven and calcined at 600° C. for 2 hours. The crush strength of the pellet obtained is comparable to the crush strength of a pellet made with only $Nd_2O_3$ nanowires (i.e., no binders or diluents).

Example 5

Preparation of $La_2O_3$ Nanowires Pellets 200 g of dried $La(OH)_3$ nanowires, prepared using the methods described in U.S. patent application Ser. No. 13/115,082, were first crushed to a coarse powder using a Frewitt Oscillating Grinder and then ground to a finer powder using a Retch Ultra Centrifugal Mill ZM200 at 6000 rpm using a 1 mm screen. 1% by weight of Methyl Stearate was then blended into the $La(OH)_3$ powder. The material was pressed into pellets using a Capplus Technologies TDP 5.5 Pellet Press with a 13 mm punch and die set. The weight of the pellets was set at 0.5 g and tonnage of the pellet was adjusted so that the desired crush strength was obtained. The pellets were finally calcined in a high temperature furnace stepwise: 30 min at 100 C, 240 min at 400 C and 240 min at 550 C with all ramp rates at 2 C/min. Doped compositions were prepared by adding appropriate amounts of nitrate salts of the desired dopant(s).

Example 6

Preparation of Pellets of $La_2O_3$ Nanowires Blended with CaO

The solid content of wet $La(OH)_3$ nanowires, prepared using the methods described in U.S. patent application Ser. No. 13/115,082 without the drying step, was determined using a Mettler Toledo moisture analyzer. An amount of CaO powder, equal to the determined weight of $La(OH)_3$ nanowires, was added and the mixture was blended in a mixer and distilled water was added to bring the moisture content of the blend to 50%. The blended material was dried in a convection oven at 120 C. The dried material was first crushed to a coarse powder using a Frewitt Oscillating Grinder and then ground to a finer powder using a Retch Ultra Centrifugal Mill ZM200 at 6000 rpm using a 1 mm screen. 1% by weight of Methyl Stearate was then blended into the mixture of $La(OH)_3$ nanowires and CaO. The material was pressed into pellets using a Capplus Technologies TDP 5.5 Pellet Press with a 13 mm punch and die set. The weight of the pellets was set at 0.5 g and tonnage of the pellet was adjusted so that the desired crush strength was obtained. The pellets were finally calcined in a high temperature furnace stepwise: 30 min at 100 C, 240 min at 400 C and 240 min at 550 C with all ramp rates at 2 C/min.

Example 7

Preparation of $La_2O_3$ Nanowire Extrudates 200 g of dried La(OH)3 nanowires, prepared using the methods described in U.S. patent application Ser. No. 13/115,082, were first crushed to a coarse powder using a Frewitt Oscillating Grinder and then ground to a finer powder using a Retch Ultra Centrifugal Mill ZM200 at 6000 rpm using a 1 mm screen. 0.1 equivalents of Acetic Aid (6.02 mL) with respect to Lanthanum and distilled water were added to the $La(OH)_3$ nanowires powder. The amount of distilled water was selected depending on the target moisture content of the extrudate paste (30-50%). The mixture was blended in a mixer until a uniform paste was achieved. The moisture content of the paste was analyzed using a Mettler Toledo moisture analyzer. The paste was extruded using an American Diamond TT100 1" barrel jacketed extruder equipped with 3 mm multi-hole die plate at a feed rate of 26 rpm and jacket temperature of 10-15 C. The extrudates were dried at 65 C for 12 hours prior to calcination. The extrudates were then calcined in a high temperature furnace stepwise: 30 min at 100 C, 240 min at 400 C and 240 min at 550 C with all ramp rates at 2 C/min.

Example 8

Preparation of Extrudates of $La_2O_3$ Nanowires Blended with CaO

The solid content of wet $La(OH)_3$ nanowires, prepared using the methods described in U.S. patent application Ser. No. 13/115,082 without the drying step, was determined using a Mettler Toledo moisture analyzer. An amount of CaO powder, equal to the determined weight of $La(OH)_3$ nanowires, was added and the mixture was blended together in a mixer. 0.1 equivalents of Acetic Acid (6.02 mL) with respect to Lanthanum and distilled water were added to the $La(OH)_3$ nanowires CaO blend. The amount of distilled water was selected depending on the target moisture content of the extrudate paste (30-50%). The mixture was blended in a mixer until a uniform paste was achieved. The moisture content of the paste was analyzed using a Mettler Toledo moisture analyzer. The paste was extruded using an American Diamond TT100 1" barrel jacketed extruder equipped with 3 mm multi-hole die plate at a feed rate of 26 rpm and jacket temperature of 10-15 C. The extrudates were dried at 65 C for 12 hours prior to calcination. The extrudates were then calcined in a high temperature furnace stepwise: 30 min at 100 C, 240 min at 400 C and 240 min at 550 C with all ramp rates at 2 C/min.

Example 9

Preparation of Extrudates of $La_2O_3$ Nanowires Blended with CaO 100 g of dried $La(OH)_3$ nanowires, prepared using the methods described in U.S. patent application Ser. No. 13/115,082, were first crushed to a coarse powder using a Frewitt Oscillating Grinder and then ground to a finer powder using a Retch Ultra Centrifugal Mill ZM200 at 6000 rpm using a 1 mm screen. 100 g of CaO powder were added and the mixture was blended together in a mixer. 0.1 equivalents of Acetic Acid (6.02 mL) with respect to Lanthanum and distilled water were added to the La(OH)3 nanowires CaO blend. The amount of distilled water was selected depending on the target moisture content of the extrudate paste (30-50%). The mixture was blended in a mixer until a uniform paste was achieved. The moisture content of the paste was analyzed using a Mettler Toledo moisture analyzer. The paste was extruded using an American Diamond TT100 1" barrel jacketed extruder equipped with 3 mm multi-hole die plate at a feed rate of 26 rpm and jacket temperature of 10-15 C. The extrudates were dried at 65 C for 12 hours prior to calcination. The extrudates were then calcined in a high temperature furnace stepwise: 30 min at 100 C, 240 min at 400 C and 240 min at 550 C with all ramp rates at 2 C/min.

Example 10

Preparation of Pellets of $La_2O_3$ Nanowires Blended with Sic 100 g of dried $La(OH)_3$ nanowires, prepared using the methods described in U.S. patent application Ser. No. 13/115,082, were first crushed to a coarse powder using a Frewitt Oscillating Grinder and then ground to a finer powder using a Retch Ultra Centrifugal Mill ZM200 at 6000 rpm using a 1 mm screen. 100 g of SiC powder were added and the mixture was blended together. 1% by weight of Methyl Stearate was then blended into the $La(OH)_3$—SiC blend. The material was pressed into pellets using a Capplus Technologies TDP 5.5 Pellet Press with a 13 mm punch and die set. The weight of the pellets was set at 0.5 g and tonnage of the pellet was adjusted so that the desired crush strength was obtained. The pellets were finally calcined in a high temperature furnace stepwise: 30 min at 100 C, 240 min at 400 C and 240 min at 550 C with all ramp rates at 2 C/min.

Example 11

Evaluation of Various Formed Aggregates

Figure 7:
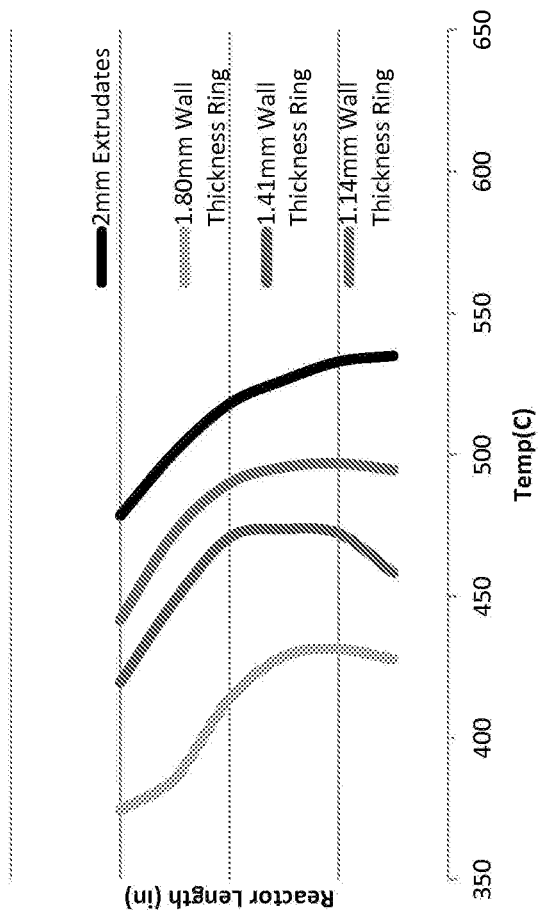
FIG. 7 shows a plot of light off temperature as a function of catalyst bed depth in an OCM reactor for four different catalyst forms.

Identical OCM catalyst material compositions were formed into tube shaped particles having cross sectional diameters of 5.3 mm and lengths of approximately 8 mm. Three different inside diameter extrudates were prepared so as to yield three different wall thicknesses for the tubes: 1.14 mm, 1.41 mm, and 1.8 mm. A control form of 2 mm extrudate pellets was also prepared. All of the extrudates were prepared by identical methods other than the resulting inside diameters. Each of the three forms and the control pellets was tested in an adiabatic pilot scale OCM reactor operating between 350° C. and 550° C. feed gas temperature, with feed gas of methane and air, and the light off temperatures were observed for the OCM reaction by measuring the outlet gas temperature. It was observed that each tube conformation performed at substantially lower light-off temperatures than the control 2 mm extrudate pellets. Further, it was observed that the thicker walls of the catalyst form (1.8 mm) provided even lower light-off temperatures than the other two tube forms. The light off temperature data is shown plotted in FIG. 7 as a function of reactor length.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A catalytic material comprising a first and second catalyst, wherein the first and second catalysts are independently selected from a mixed oxide of lanthanide elements, a mixed oxide of magnesium and manganese, a mixed oxide of manganese and tungsten, a mixed oxide of a lanthanide element and tungsten and a mixed oxide of a rare earth element and a group 13 element and are segregated into discrete layers, wherein the second catalyst has a temperature of activation in an oxidative coupling of methane (OCM) reaction at least 25 degrees higher than the first catalyst, and wherein the catalytic material comprises a C2 selectivity of greater than 50% and a methane conversion of greater than 20% when the catalytic material is employed as a heterogeneous catalyst in the oxidative coupling of methane at a temperature of 750° C. or less.

2. The catalytic material of claim 1, wherein the first catalyst is a nanowire catalyst.

3. The catalytic material of claim 1, wherein the second catalyst is a bulk catalyst.

4. The catalytic material of claim 1, wherein each of the first and second catalysts are nanowire catalysts.

5. The catalytic material of claim 1, wherein each of the first and second catalyst are bulk catalysts.

6. The catalytic material of claim 1, wherein the catalytic activity of the second catalyst increases with increasing temperature.

7. The catalytic material of claim 1, wherein the catalytic material comprises a void fraction volume of about 35% to about 70%.

8. The catalytic material of claim 7, wherein the catalytic material comprises a void fraction volume of about 45% to about 65%.

9. The catalytic material of claim 1, wherein the catalytic material comprises catalyst particles having a cross sectional dimension in at least one dimension between about 1 mm and about 20 mm.

10. The catalytic material of claim 9, wherein the cross sectional dimension is between about 2 mm and about 10 mm.

11. The catalytic material of claim 1, wherein the catalytic material comprises catalyst particles having a surface area to volume ratio between about 0.1 $mm^{-1}$ and about 10 $mm^{-1}$.

12. The catalytic material of claim 11, wherein the catalytic material comprises catalyst particles having a surface area to volume ratio between about 0.1 $mm^{-1}$ and about 5 $mm^{-1}$.

13. The catalytic material of claim 1, wherein the catalytic material comprises a crush strength greater than 1 $N/mm^2$.

14. The catalytic material of claim 13, wherein the catalytic material comprises a crush strength greater than 10 $N/mm^2$.

15. The catalytic material of claim 1, wherein the catalytic material comprises a porosity of between about 10% and about 80%.

16. The catalytic material of claim 15, wherein the porosity is between about 40% and about 60%.

17. The catalytic material of claim 1, wherein the ratio of the surface area of the catalytic form envelope to the volume of the catalytic form envelope ranges from about 0.5 $mm^{-1}$ to about 4 $mm^{-1}$.

18. The catalytic material of claim 1, wherein the catalytic material comprises a homogenously dispersed active catalyst.

19. The catalytic material of claim 1, wherein the catalytic material comprises a surface area ranging from about 1 $m^2/g$ to about 50 $m^2/g$.

20. The catalytic material of claim 1, wherein at least one of the first and second catalysts is an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof.

21. The catalytic material of claim 1 in combination with a diluent.

22. The catalytic material of claim 21, wherein the diluent comprises an alkaline earth metal compound, silicon carbide, cordierite, $B_2O_3$, $In_2O_3$, $SrAl_2O_4$, $B_4SrO_7$ or combinations thereof.

23. The catalytic material of claim 1, wherein the second catalyst has a higher temperature of activation in the OCM reaction than the first catalyst.

24. The catalytic material of claim 23, wherein the second catalyst has a temperature of activation in the OCM reaction of at least 50° C. higher than the first catalyst.

25. The catalytic material of claim 23, wherein the second catalyst has a temperature of activation in the OCM reaction of at least 100° C. higher than the first catalyst.

26. The catalytic material of claim 23, wherein the second catalyst has a temperature of activation in the OCM reaction of at least 200° C. higher than the first catalyst.

27. The catalytic material of claim 1, wherein the second catalyst has a C2 selectivity of greater than 50% at a temperature above 700° C., and the first catalyst has a C2 selectivity of greater than 50% at a temperature below 700° C.

28. The catalytic material of claim 1, wherein the second catalyst comprises LiMgMnB or Na/MnWO4.

29. A method for the oxidative coupling of methane, the method comprising contacting the catalytic material of claim 1 with a mixture comprising methane and oxygen.

30. A method for the preparation of ethane or ethylene, the method comprising contacting the catalytic material of claim 1 with a mixture comprising methane and oxygen.

31. A method for the preparation of a downstream product of ethylene, the method comprising oligomerizing ethylene, wherein the ethylene has been prepared by a method comprising contacting the catalytic material of claim 1 with a mixture comprising methane and oxygen.

* * * * *